(12) United States Patent
Shanler et al.

(10) Patent No.: US 8,883,838 B2
(45) Date of Patent: Nov. 11, 2014

(54) PHARMACEUTICAL CREAM COMPOSITIONS AND METHODS OF USE

(75) Inventors: Stuart D. Shanler, Pomona, NY (US); Christopher Powala, Radnor, PA (US); Luis Rios, Pembroke Pines, FL (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/309,403

(22) Filed: Dec. 1, 2011

(65) Prior Publication Data

US 2012/0149748 A1 Jun. 14, 2012

Related U.S. Application Data

(60) Provisional application No. 61/419,693, filed on Dec. 3, 2010, provisional application No. 61/419,697, filed on Dec. 3, 2010.

(51) Int. Cl.
*A61K 9/107* (2006.01)
*A61K 47/14* (2006.01)
*A61K 9/00* (2006.01)
*A61K 31/4174* (2006.01)
*A61K 47/10* (2006.01)

(52) U.S. Cl.
CPC ........... *A61K 31/4174* (2013.01); *A61K 9/0014* (2013.01); *A61K 47/14* (2013.01); *A61K 9/107* (2013.01); *A61K 47/10* (2013.01)
USPC ........................................ 514/401

(58) Field of Classification Search
USPC ........................................ 514/401
See application file for complete search history.

(56) References Cited

U.S. PATENT DOCUMENTS

| | | | |
|---|---|---|---|
| 3,670,087 A | 6/1972 | Lorenzetti | |
| 5,153,230 A * | 10/1992 | Jaffery | 514/458 |
| 5,407,958 A * | 4/1995 | Heath et al. | 514/546 |
| 6,136,328 A * | 10/2000 | Sebillotte-Arnaud et al. | 424/401 |
| 2002/0037314 A1* | 3/2002 | Meisner | 424/449 |
| 2004/0242588 A1* | 12/2004 | Dejovin et al. | 514/249 |
| 2005/0165079 A1* | 7/2005 | Shanler et al. | 514/401 |
| 2007/0065390 A1 | 3/2007 | Spengler | |
| 2008/0193551 A1* | 8/2008 | De Waard et al. | 424/535 |

FOREIGN PATENT DOCUMENTS

| | | |
|---|---|---|
| WO | 2009-065116 | 5/2009 |
| WO | 2012-047645 | 4/2012 |

* cited by examiner

*Primary Examiner* — Jeffrey S. Lundgren
*Assistant Examiner* — Zenab Olabowale
(74) *Attorney, Agent, or Firm* — Krishna Banerjee

(57) ABSTRACT

The present invention provides pharmaceutical cream compositions comprising oxymetazoline and methods for treating rosacea and other skin disorders as described herein using the above cream compositions.

15 Claims, 3 Drawing Sheets

PHARMACEUTICAL CREAM COMPOSITIONS AND METHODS OF USE

CROSS REFERENCE

This application claims the benefit of U.S. Provisional Patent Application Ser. No. 61/419,693 filed on Dec. 3, 2010, and U.S. Provisional Patent Application Ser. No. 61/419,697 filed on Dec. 3, 2010, the disclosures of which are incorporated herein by reference in their entirety.

FIELD OF THE INVENTION

The present invention is directed to cream compositions and methods in which these cream compositions are administered to patients for the treatment of one or more dermatological conditions.

BACKGROUND OF THE INVENTION

Rosacea is a chronic disease most commonly characterized by facial erythema (redness). There are at least four identified rosacea subtypes and patients may have more than one subtype present. The four most well recognized subtypes are erythematotelangiectatic rosacea (ETR); papulopustular rosacea; phymatous rosacea; and ocular rosacea. Other less common forms exist and the signs and symptoms of each subtype are not unique to that subtype and may overlap or coexist with any of the manifestations of any other subtype. ETR may be characterized by transient and/or permanent erythema with a tendency to flush and blush easily and telangiectasias, which in its milder form may resemble or present as erythema (redness) and in its more pronounced state may manifest as discrete visible blood vessels on the surface of the skin. Papulopustular rosacea may be characterized by transient and/or permanent erythema with papules (red bumps) and pustules (pus filled bumps). Without wishing to be bound by theory, though the papules and other inflammatory lesions (e.g. pustules) of papulopustular rosacea may be mistaken for acne, it is believed that the papules and pustules of rosacea are different from the papules and pustules of acne and arise from different underlying pathophysiologic processes. Phymatous rosacea may be characterized by thickening skin, irregular surface nodularities, enlargement of facial areas (e.g. nose and cheeks), erythema and telangiectasias. Ocular rosacea may be characterized by red, dry and irritated eyes and eyelids. In each subtype, erythema and telangiectasias of varying degree may be a feature.

Rosacea patients may need topical or oral (systemic) medication to alleviate their distress; however, a patient's skin may be so sensitive that many products are irritating and, in fact, may exacerbate the symptoms of rosacea and may cause more redness and discomfort than patients can tolerate. Thus, rosacea can be very difficult to effectively treat and thus may not only be physically distressing but also psychologically distressing. Accordingly, there is a need for a cosmetically and pharmaceutically acceptable therapeutic which addresses the myriad manifestations of rosacea including, but not limited to, the erythema or redness associated with rosacea and the telangiectasias associated with rosacea. Additionally, there is a need for a cosmetically and pharmaceutically acceptable therapeutic which addresses the inflammatory lesions and manifestations associated with rosacea including the papules, pustules and phymas (skin thickening).

U.S. Pat. No. 7,812,049 to Shanler et.al. describes the use of oxymetazoline to treat erythema resulting from rosacea.

There exists a need in the art for a topical pharmaceutical composition comprising oxymetazoline which is physically stable (i.e. without phase separation) and chemically stable with the active pharmaceutical agent and which optimizes the delivery of the oxymetazoline to the skin in such a manner as to effectively treat the pathologic condition.

There also exists a need in the art for a topical cream formulation which is physically stable (i.e. without phase separation) and chemically stable that is well tolerated by and suitable for use in individuals with sensitive, reactive, easily irritated or damaged skin.

BRIEF DESCRIPTION

Embodiments are generally directed to a cream formulation. Certain embodiments may include a cream formulation of oxymetazoline. Some embodiments may be directed to a cosmetically acceptable formulation comprising oxymetazoline and a pharmaceutically acceptable excipient, wherein the formulation is a cream. Some embodiments may be directed to a formulation comprising oxymetazoline and a pharmaceutically acceptable excipient, wherein the formulation is a cream. Some embodiments may be directed to a cream formulation comprising oxymetazoline in a therapeutically effective amount and a pharmaceutically acceptable excipient. Some embodiments of the invention are directed to a cream formulation comprising oxymetazoline, an emulsifier and an emollient. Some embodiments may be directed to a cream formulation comprising oxymetazoline, an emulsifier and an emollient, wherein a ratio of the emulsifier to the emollient comprises from about 0.1:1 to about 1.8:1. In other embodiments, the ratio of the emulsifier to the emollient may comprise from about 0.2:1 to about 1.8:1, from about 0.3:1 to about 1.8:1, or from about 0.4:1 to about 1.8:1, or from about 0.7:1 to about 1.8:1. In certain embodiments, the cream formulation may have a pH from about 2.0 to about 7.0 at room temperature. In further embodiments, the cream formulation may have a pH from about 4.0 to about 5.5 at room temperature.

In some embodiments, the cream formulation may further include a sunscreen or sun-blocking agent. In certain embodiments, the sun-blocking agent may be zinc oxide, titanium dioxide or combinations thereof.

Some embodiments may be directed to a cream formulation comprising oxymetazoline in an amount of from about 0.0075% to about 5% by weight and pharmaceutically acceptable excipients. In some embodiments, the cream formulation may comprise oxymetazoline in an amount from about 0.01% to about 2% by weight. Embodiments may include one or more emulsifiers in a total amount of from about 1% to about 30% by weight of the pharmaceutical composition; and/or one or more emollients in a total amount of from about 1% to about 50% by weight of the pharmaceutical composition. In some embodiments the emollients are in an amount of from about 1% to about 20% by weight of the pharmaceutical composition. In some embodiments, the emulsifier may comprise Tefose 63™. In some embodiments, the emulsifier may comprise PEG-stearate, glycol stearate or a combination thereof. In some embodiments, the emulsifier may comprise ethoxylated fatty acids. In some embodiments, the emulsifier may comprise cetostearyl alcohol. In some embodiments, the formulation may further comprise additional additives selected from the group consisting of preservatives, emulsion stabilizers, pH adjusters, chelating agents, viscosity modifiers, anti-oxidants, surfactants, emollients, opacifying agents, skin conditioners, buffers, and combinations thereof. In some embodiments, the formulation may further comprise a topically active pharmaceutical or cosmetic agent.

In certain embodiments, a cream comprising oxymetazoline, a vasoconstrictor and pharmaceutically acceptable excipients is provided. In certain embodiments, a cream comprising oxymetazoline, an alpha-adrenergic agonist and pharmaceutically acceptable excipients is provided. In certain embodiments, a cream comprising oxymetazoline, an imidazoline alpha-adrenergic agonist and pharmaceutically acceptable excipients is provided. In certain embodiments, a cream comprising oxymetazoline, a non-imidazoline alpha-adrenergic agonist and pharmaceutically acceptable excipients is provided. In certain embodiments, a cream comprising oxymetazoline, an alpha-1 adrenergic agonist and pharmaceutically acceptable excipients is provided. In certain embodiments, a cream comprising oxymetazoline, an alpha-2 adrenergic agonist and pharmaceutically acceptable excipients is provided. In certain embodiments, a cream comprising oxymetazoline, a selective alpha-adrenergic agonist and pharmaceutically acceptable excipients is provided. In certain embodiments, a cream comprising oxymetazoline, a non-selective alpha-adrenergic agonist and pharmaceutically acceptable excipients is provided. In certain embodiments, a cream comprising oxymetazoline, a selective alpha-1 adrenergic agonist and pharmaceutically acceptable excipients is provided. In certain embodiments, a cream comprising oxymetazoline, a selective alpha-2 adrenergic agonist and pharmaceutically acceptable excipients is provided. In certain embodiments, a cream comprising oxymetazoline, a non-selective alpha-1 adrenergic agonist and pharmaceutically acceptable excipients is provided. In certain embodiments, a cream comprising oxymetazoline, a non-selective alpha-2 adrenergic agonist and pharmaceutically acceptable excipients is provided.

In some embodiments, the cream formulation may be stable, non-irritating, cosmetically acceptable, compatible with a wide variety of APIs, or combinations thereof. In certain embodiments, the cream formulation may be non-irritating to patients with sensitive or "reactive" skin such as is commonly encountered in patients with eczema, dermatitis or other conditions characterized by sensitive skin or a disturbance of the epidermal barrier. In certain embodiments, the cream formulation may be non-irritating to individuals who are categorized as "stingers" or "burners," such as patients with rosacea. Such individuals who are "stingers" or "burners" may normally experience symptoms such as itching, burning, stinging, prickling, tingling warmth or flushing to external stimuli including external treatment. However, in certain embodiments herein, the cream formulations may be non-irritating to such individuals so that such symptoms are present in a reduced fashion or are not present. In certain embodiments, the cream formulation may be soothing to the skin. In some embodiments, the soothing effect of the cream formulations of embodiments herein may be long-lasting.

In some embodiments, the cream formulation does not contain an active pharmaceutical ingredient. In some embodiments, the cream formulation may be a vehicle to deliver a pharmacological agent or drug topically. In some embodiments, the cream formulation comprises an active pharmaceutical ingredient other than oxymetazoline. Some embodiments may be directed to a formulation comprising an active pharmaceutical ingredient other than oxymetazoline and a pharmaceutically acceptable excipient. In certain embodiments, a cream comprising an alpha-adrenergic agonist and pharmaceutically acceptable excipients is provided. In certain embodiments, a cream comprising an imidazoline alpha-adrenergic agonist and pharmaceutically acceptable excipients is provided. In certain embodiments, a cream comprising a non-imidazoline alpha-adrenergic agonist and pharmaceutically acceptable excipients is provided. In certain embodiments, a cream comprising an alpha-1 adrenergic agonist and pharmaceutically acceptable excipients is provided. In certain embodiments, a cream comprising an alpha-2 adrenergic agonist and pharmaceutically acceptable excipients is provided. In certain embodiments, a cream comprising a selective alpha-adrenergic agonist and pharmaceutically acceptable excipients is provided. In certain embodiments, a cream comprising a non-selective alpha-adrenergic agonist and pharmaceutically acceptable excipients is provided. In certain embodiments, a cream comprising a selective alpha-1 adrenergic agonist and pharmaceutically acceptable excipients is provided. In certain embodiments, a cream comprising a selective alpha-2 adrenergic agonist and pharmaceutically acceptable excipients is provided. In certain embodiments, a cream comprising a non-selective alpha-1 adrenergic agonist and pharmaceutically acceptable excipients is provided. In certain embodiments, a cream comprising a non-selective alpha-2 adrenergic agonist and pharmaceutically acceptable excipients is provided.

In some embodiments, a method of treating a skin condition, including, but not limited to, rosacea, including, for example, erythematotelangiectatic rosacea, papulopustular rosacea, phymatous rosacea, ocular rosacea or combinations thereof; and symptoms associated with rosacea, including, for example, papules, pustules, phymas (skin thickening), telangiectasias or erythema associated with rosacea, other skin erythemas, telangiectasias, purpura or the like, and other manifestations associated therewith; other inflammatory conditions of the skin including, but not limited to, keratosis pilaris, lupus miliaris dissemniatus faciei, eczema, dermatitis, such as contact dermatitis, atopic dermatitis, seborrheic dermatitis, nummular dermatitis, generalized exfoliative dermatitis, statis dermatitis, neurodermatitis, lichen simplex chronicus, xerosis and xerotic dermatitis, dyshidrosis and dyshidrotic dermatitis, asteotic dermatitis or other conditions characterized by sensitive skin or a disturbance of the epidermal barrier; disorders characterized by rough, dry, cracked or fissured skin, disorders characterized by hyperkeratotic skin such as keratodermas and ichthyosisis and ichthyosiform dermatoses; disorders of hair follicles and sebaceous glands, such as acne, perioral dermatitis, and pseudofolliculitis barbae; disorders of sweat glands, such as miliaria, including, but not limited to, miliaria crystallina, miliaria rubra, miliaria profunda, miliaria pustulosa; sunburn, chronic actinic damage, poikiloderma, radiation dermatitis, actinic purpura ("solar purpura"); other inflammatory dermatoses, reactions and conditions of the skin, including, but not limited to, psoriasis, drug eruptions, erythema multiforme, erythema nodosum, and granuloma annulare; diseases and conditions characterized by bleeding or bruising such as petechiae, ecchymosis, purpura and the like including any accumulation of blood in the skin due to vascular extravasation, irrespective of size or cause, bleeding or bruising due to any skin injury which may include any trauma including surgical or procedural trauma; infection, inflammatory dermatoses or inflammation due to any cause or combinations thereof comprising administering a cream formulation of embodiments described herein is provided. In some embodiments the cream formulation may also have a moisturizing, hydrating, soothing, calming or protective effect on the skin of the subject.

Certain embodiments may include a method of moisturizing, hydrating, soothing, calming or protecting the skin comprising administering a cream formulation, wherein the cream formulation does not contain an API. In embodiments, the cream is non-irritating. In some embodiments, the cream formulation may be used to treat sensitive, irritated, dry or damaged skin. In some embodiments, the sensitive, irritated, or dry skin may be found in patients with rosacea, xerosis, eczema or dermatitis. In some embodiments, the cream formulation without an API may relieve or treat the symptoms of rosacea and symptoms associated with rosacea, including, for example, papules, pustules, phymas (skin thickening), telangiectasias or erythema associated with rosacea, other skin erythemas, telangiectasias, purpura or the like, and other manifestations associated therewith; other inflammatory conditions of the skin including, but not limited to, keratosis pilaris, lupus miliaris dissemniatus faciei, eczema, dermatitis, such as contact dermatitis, atopic dermatitis, seborrheic dermatitis, nummular dermatitis, generalized exfoliative dermatitis, statis dermatitis, neurodermatitis, lichen simplex chronicus, xerosis and xerotic dermatitis, dyshidrosis and dyshidrotic dermatitis, asteotic dermatitis or other conditions characterized by sensitive skin or a disturbance of the epidermal barrier; disorders characterized by rough, dry, cracked or fissured skin, disorders characterized by hyperkeratotic skin such as keratodermas and ichthyosisis and ichthyosiform dermatoses; disorders of hair follicles and sebaceous glands, such as acne, perioral dermatitis, and pseudofolliculitis barbae; disorders of the sweat glands, such as miliaria (including, but not limited to, crystalline, rubra, profunda, or pustule); sunburn, chronic actinic damage, poikiloderma, radiation dermatitis, actinic purpura ("solar purpura"); other inflammatory dermatoses, reactions and conditions of the skin, including, but not limited to, psoriasis, drug eruptions, erythema multiforme, erythema nodosum, and granuloma annulare; diseases and conditions characterized by bleeding or bruising such as petechiae, ecchymosis, purpura and the like including any accumulation of blood in the skin due to vascular extravasation, irrespective of size or cause, bleeding or bruising due to any skin injury which may include any trauma including surgical or procedural trauma; infection, inflammatory dermatoses or inflammation due to any cause.

In certain embodiments herein, the cream formulation may be used to treat skin conditions of various types. For example, the cream formulation may be used to treat rosacea, eczema, dermatitis, atopic dermatitis, psoriasis, steroid-responsive dermatoses, pruritis, or xerosis. In certain embodiments, the cream formulation may be used to treat dry, irritated, erythematous or pruriginous skin in subjects with no underlying skin disease, such as, for example, after physical skin trauma or mechanical skin trauma such as shaving (as a post-shave "healer") or tweezing, after bathing, showering, sweating; or after exposure to extrinsic factors such as "the elements", for example, sun, wind, cold temperature, low humidity, hot and humid conditions, radiation, air pollution, smoke or cigarette smoke; or treat said skin irritation or erythema that is as a result of exposure to a topical irritant such as a chemical agent, insect sting or bite, plant exposure, or application of a topically applied drug product, medicament or topical product, such as a fragrance, insect repellant, exfoliant, skin peeling agent, shaving or depilatory preparation, skin or hair cleanser, soap, detergent or conditioner, hair treatment or colorant, antiperspirant, deodorant, sunscreen, tanning agent, moisturizer, astringent, toner, moisturizer, serum, mask, facial or body cosmetic, ointment, cream, lotion, gel, foam, solution, shake, or powder.

The cream formulations of embodiments herein may have a hydrating effect on the skin. In certain embodiments, the cream formulations may be used to treat intrinsic or extrinsic aging of the skin including, but not limited to, dermatoheliosis or photoaging, blemishes, ephilides, age spots (solar lentigines), solar keratoses, xerosis, roughness of the skin, dullness of the skin, thinning of the skin, sagging of the skin, fine lines, fine and deep facial lines or creases, wrinkles; or improve skin tone, smoothness, softness, suppleness, radiance, skin flexibility, and global skin comfort.

In certain embodiments, the cream formulation may be used as a delivery vehicle for the topical delivery of pharmaceutically active ingredients including, but not limited to, potentially irritating active drug substances. In certain embodiments, these potentially active drug substances may include, but are not limited to, alpha hydroxy acids, retinoic acids, benzoyl peroxide, calcipotriene, calcineurin inhibitors, sunscreens, sunblocks, bleaching agents, depilitories, antiperspirants, or combinations thereof. In some embodiments, the active drug may be anti-rosacea agents such as metronidazole, precipitated sulfur, sodium sulfacetamide, or azelaic acid; antibacterial agents (antibiotics) such as clindamycin phosphate, erythromycin, or antibiotics from the tetracycline family; antimycobacterial agents such as dapsone; other anti-acne agents such as retinoids, or benzoyl peroxide; antiparasitic agents such as metronidazole, permethrin, crotamiton, thiabendazole, ivermectin or pyrethroids; antifungal agents such as compounds of the imidazole family such as miconazole, clotrimazole, econazole, ketoconazole, or salts thereof, polyene compounds such as amphotericin B, compounds of the allylamine family such as terbinafine; steroidal anti-inflammatory agents such as hydrocortisone triamcinolone, fluocinonide, betamethasone valerate or clobetasol propionate, or non-steroidal anti-inflammatory agents such as ibuprofen and salts thereof, naproxen and salts thereof, or acetaminophen; anesthetic agents such as the "amide" and "ester" anesthetics such as lidocaine, prilocaine, tetracaine, hydrochloride and derivatives thereof; antipruriginous agents such as thenaldine, trimeprazine, or pramoxine; antiviral agents such as acyclovir; keratolytic agents such as alpha- and beta-hydroxy acids such as glycolic acid or salicylic acid, or urea; anti-free radical agents (antioxidants) such as Vitamin E (alpha tocopherol) and its derivatives, Vitamin C (ascorbic acid), Vitamin A (retinol) and its derivatives, and superoxide dismutases; antiseborrheic agents such as zinc pyrithione and selenium sulfide; antihistamines such as cyproheptadine or hydroxyzine; tricyclic antidepressants such as doxepin hydrochloride; antipsoriatic agents such as calcipotriene, anthralines, coal tar; immune modulating agents such as imiquimod; calcineurin inhibitors pimecrolimus and tacrolimus; or chemotherapeutic agents such as 5-fluorouracil, nitrogen mustard, carmustine, bexarotene, mitomycin-c and combinations thereof.

The cream formulations of certain embodiments herein may also be used as a delivery vehicle for topically administered anti-infectives such as, but not limited to, antibiotics, antifungals, antiparasitic, and antiviral agents, corticosteroids, imiquimod or other immune modulating drugs, topical anesthetics, topical chemotherapeutic, or topical photosensitizing agents.

Certain embodiments herein include a method of treating or preventing a dermatosis such as acne, rosacea, xerosis, eczema, or dermatitis comprising administering the cream formulation of embodiments herein to a subject in need thereof. In certain embodiments, the cream formulation may be administered topically to a subject in need thereof. In particular embodiments, the subject may be susceptible to a recurrence of the dermatosis.

In certain embodiments, the compositions may be used therapeutically without an API. In some embodiments, the cream formulation of embodiments herein may be used as a delivery vehicle for the delivery of topical agents to a subject's nails.

DESCRIPTION OF DRAWINGS

For a fuller understanding of the nature and advantages of embodiments described herein, reference should be made to the following detailed description taken in connection with the accompanying drawings, in which.

DETAILED DESCRIPTION

Figure 1:
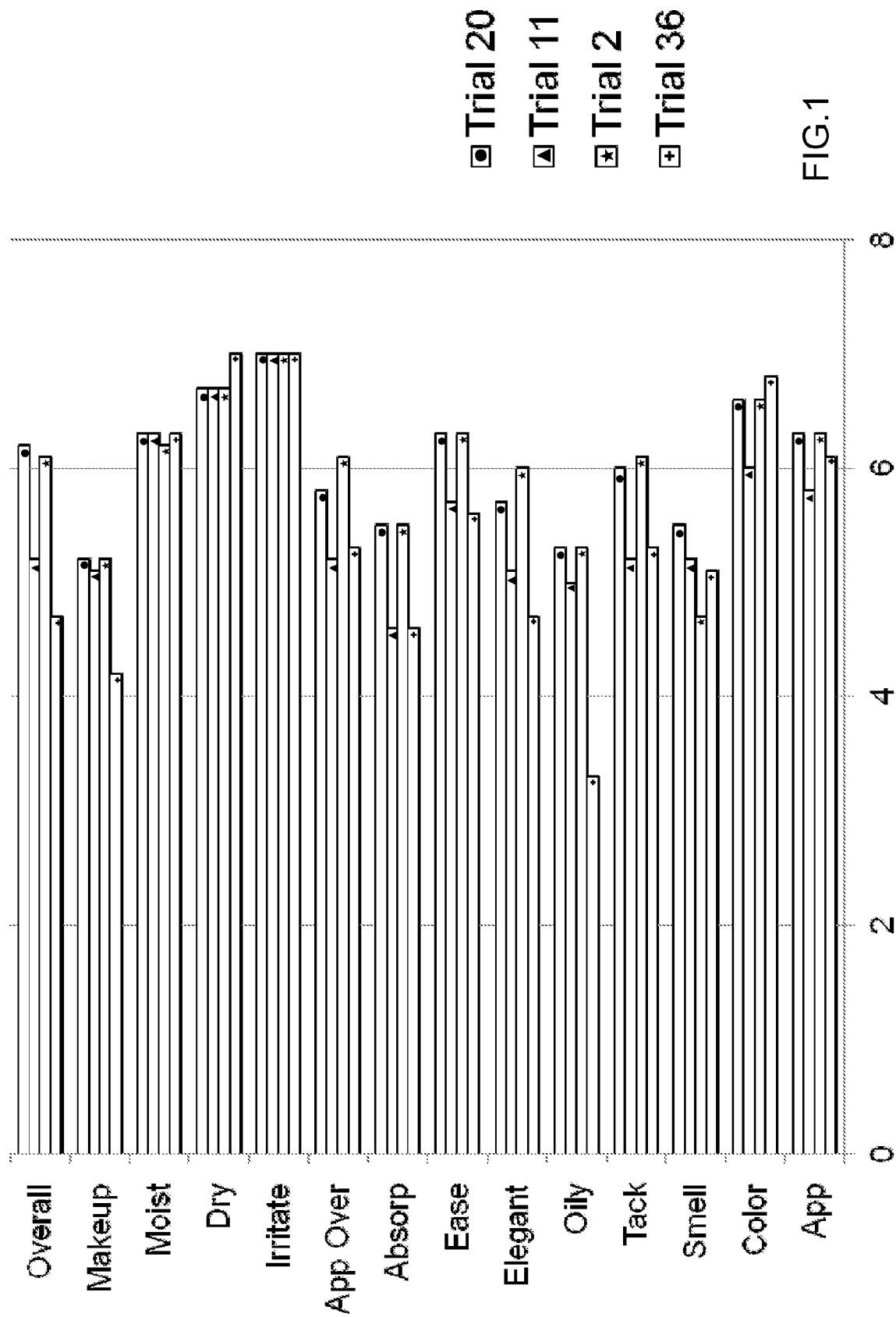
FIG. 1 is a bar graph showing the mean cosmetic acceptability scores including appearance and sensorial evaluation scores by category for creams of Trial 36, Trial 2, Trial 11 and Trial 20.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to a "preservative" is a reference to one or more preservatives and equivalents thereof known to those skilled in the art, and so forth.

As used herein, the term "about" means plus or minus 10% of the numerical value of the number with which it is being used. Therefore, about 50% means in the range of 45%-55%.

"Administering", when used in conjunction with a therapeutic, means to administer a therapeutic directly into or onto a target tissue or to administer a therapeutic to a subject, whereby the therapeutic positively impacts the tissue to which it is targeted. Thus, as used herein, the term "administering", when used in conjunction with a therapeutic, can include, but is not limited to, providing a therapeutic to a subject systemically by, for example, intravenous injection, whereby the therapeutic reaches the target tissue. Administering a composition or therapeutic may be accomplished by, for example, injection, oral administration, topical administration, or by these methods in combination with other known techniques. Such combination techniques may include heating, radiation, ultrasound and the use of delivery agents.

Preferably, administering is a self-administration, wherein the therapeutic or composition is administered by the subject themselves. Alternatively, administering may be administration to the subject by a health care provider.

"Providing", when used in conjunction with a therapeutic, means to administer a therapeutic directly into or onto a target tissue, or to administer a therapeutic to a subject whereby the therapeutic positively impacts the tissue to which it is targeted.

The term "animal" as used herein includes, but is not limited to, humans and non-human vertebrates such as wild, domestic and farm animals.

The term "patient" or "subject" as used herein is an animal, particularly a human, suffering from an unwanted disease or condition that may be treated by the therapeutic and/or compositions described herein.

The term "improves" is used to convey that the present invention changes either the characteristics and/or the physical attributes of the tissue to which it is being provided, applied or administered. The term "improves" may also be used in conjunction with a diseased state such that when a diseased state is "improved" the symptoms or physical characteristics associated with the diseased state are diminished, reduced or eliminated.

The term "inhibiting" generally refers to prevention of the onset of the symptoms, alleviating the symptoms, or eliminating the disease, condition or disorder.

"Optional" or "optionally" means that the subsequently described event or circumstance may or may not occur, and that the description includes instances where the event occurs and instances where it does not.

As used herein, "room temperature" means an indoor temperature of from about 20° C. to about 25° C. (68 to 77° F.).

Throughout the specification of the application, various terms are used such as "primary," "secondary," "first," "second," and the like. These terms are words of convenience in order to distinguish between different elements, and such terms are not intended to be limiting as to how the different elements may be utilized.

By "pharmaceutically acceptable," "physiologically tolerable," and grammatical variations thereof, as they refer to compositions, carriers, diluents, and reagents or other ingredients of the formulation, can be used interchangeably and represent that the materials are capable of being administered without the production of undesirable physiological effects such as rash, burning, irritation or other deleterious effects to such a degree as to be intolerable to the recipient thereof.

As used herein, the term "cosmetically acceptable" and grammatical variations thereof, as they refer to compositions, carriers, diluents, and reagents or other ingredients of the formulation, represent that the materials used and final composition are not irritating or otherwise harmful to the patient in general and to the skin, in particular, and preferably are pleasant and well tolerated with respect to general appearance, pH, color, smell and texture (feel), that they are not, for example, unacceptably sticky (tacky), oily or drying, and that they do spread easily, absorb into the skin at an acceptable rate of absorption, and are generally moisturizing.

"Pharmaceutically acceptable salts" include both acid and base addition salts. "Pharmaceutically acceptable acid addition salt" refers to those salts that retain biological effectiveness and properties of the free bases and that include inorganic acids such as, for example, hydrochloric acid, hydrobromic acid, sulfuric acid, nitric acid, carbonic acid, phosphoric acid, and the like. Organic acids may be selected from aliphatic, cycloaliphatic, aromatic, aralyphatic, heterocyclic, carboxylic, and sulfonic classes of organic acids, such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid, and the like.

As used herein, the term "therapeutic" means an agent utilized to treat, combat, ameliorate, prevent or improve an unwanted condition or disease of a subject. In part, embodiments of the present invention may be directed to the treatment of various skin diseases, conditions or disorders or symptoms thereof, including, but not limited to, rosacea and symptoms associated with rosacea, including, for example, papules, pustules, phymas (skin thickening), telangiectasias or erythema associated with rosacea, other skin erythemas, telangiectasias, purpura or the like, and other manifestations associated therewith; other inflammatory conditions of the skin including, but not limited to, keratosis pilaris, lupus miliaris dissemniatus faciei, eczema, dermatitis, such as contact dermatitis, atopic dermatitis, seborrheic dermatitis, nummular dermatitis, generalized exfoliative dermatitis, statis dermatitis, neurodermatitis, lichen simplex chronicus, xerosis and xerotic dermatitis, dyshidrosis and dyshidrotic dermatitis, asteototic dermatitis or other conditions characterized by sensitive skin or a disturbance of the epidermal barrier; disorders characterized by rough, dry, cracked or fissured skin, disorders characterized by hyperkeratotic skin such as keratodermas and ichthyosisis and ichthyosiform dermatoses; disorders of hair follicles and sebaceous glands, such as acne, perioral dermatitis, and pseudofolliculitis barbae; disorders of sweat glands, such as miliaria, including, but not limited to, miliaria crystallina, miliaria rubra, miliaria profunda, miliaria pustulosa; sunburn, chronic actinic damage, poikiloderma, radiation dermatitis, actinic purpura ("solar purpura"); other inflammatory dermatoses, reactions and conditions of the skin, including, but not limited to, psoriasis, drug eruptions, erythema multiforme, erythema nodosum, and granuloma annulare; diseases and conditions characterized by bleeding or bruising such as petechiae, ecchymosis, purpura and the like including any accumulation of blood in the skin due to vascular extravasation, irrespective of size or cause, bleeding or bruising due to any skin injury which may include any trauma including surgical or procedural trauma; infection, inflammatory dermatoses or inflammation due to any cause or combinations thereof. In part, some embodiments may be directed to a cream formulation that has moisturizing properties.

The terms "therapeutically effective" or "effective", as used herein, may be used interchangeably and refer to an amount of a therapeutic composition of embodiments of the present invention (e.g., a composition comprising oxymetazoline). For example, a therapeutically effective amount of a composition is an amount of the composition, and particularly the active ingredient, such as oxymetazoline, that generally achieves the desired effect.

A "therapeutically effective amount" or "effective amount" of a composition is an amount necessary or sufficient to achieve the desired result. The activity contemplated by the embodiments herein includes medically therapeutic, cosmetically therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. However, the effective amount administered can be determined by the practitioner or manufacturer or patient in light of the relevant circumstances including the condition to be treated, the choice of compound to be administered, and the chosen route of administration, and therefore, the above dosage ranges are not intended to limit the scope of the invention in any way. A therapeutically effective amount of the compound of embodiments herein is typically an amount such that when it is administered in a physiologically tolerable excipient composition, it is sufficient to achieve an effective systemic concentration or local concentration in or on the tissue to achieve the desired therapeutic or clinical outcome.

The terms "treat," "treated," or "treating" as used herein refers to therapeutic treatment, cosmetic treatment and/or prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects.

As used herein, the term "consists of" or "consisting of" means that the formulation includes only the elements, steps, or ingredients specifically recited in the particular claimed embodiment or claim.

As used herein, the term "consisting essentially of" or "consists essentially of" means that the only active pharmaceutical ingredient in the formulation or method that treats the specified condition (e.g. erythema or redness associated with the particular disease to be treated) is the specifically recited therapeutic in the particular embodiment or claim.

Generally speaking, the term "tissue" refers to any aggregation of similarly specialized cells which are united in the performance of a particular function.

As used herein, the term "erythema" refers to any redness of the skin due to hyperemia, congestion of the vasculature or dilation of the vasculature of the skin and its surrounding structures. Erythema may occur in many conditions of the skin including, but not limited to, rosacea and symptoms associated with rosacea, including, for example, papules, pustules, phymas (skin thickening), telangiectasias or erythema associated with rosacea, other skin erythemas, telangiectasias, purpura or the like, and other manifestations associated therewith; other inflammatory conditions of the skin including, but not limited to, keratosis pilaris, lupus miliaris dissemniatus faciei, eczema, dermatitis, such as contact dermatitis, atopic dermatitis, seborrheic dermatitis, nummular dermatitis, generalized exfoliative dermatitis, statis dermatitis, neurodermatitis, lichen simplex chronicus, xerosis and xerotic dermatitis, dyshidrosis and dyshidrotic dermatitis, asteototic dermatitis or other conditions characterized by sensitive skin or a disturbance of the epidermal barrier; disorders characterized by rough, dry, cracked or fissured skin, disorders characterized by hyperkeratotic skin such as keratodermas and ichthyosisis and ichthyosiform dermatoses; disorders of hair follicles and sebaceous glands, such as acne, perioral dermatitis, and pseudofolliculitis barbae; disorders of sweat glands, such as miliaria, including, but not limited to, miliaria crystallina, miliaria rubra, miliaria profunda, miliaria pustulosa; sunburn, chronic actinic damage, poikiloderma, radiation dermatitis, actinic purpura ("solar purpura"); other inflammatory dermatoses, reactions and conditions of the skin, including, but not limited to, psoriasis, drug eruptions, erythema multiforme, erythema nodosum, and granuloma annulare; diseases and conditions characterized by bleeding or bruising such as petechiae, ecchymosis, purpura and the like including any accumulation of blood in the skin due to vascular extravasation, irrespective of size or cause, bleeding or bruising due to any skin injury which may include any trauma including surgical or procedural trauma; infection, inflammatory dermatoses; inflammation due to any cause or a combination thereof.

Keratosis pilaris (KP) is a very common genetic follicular condition that is manifested by the appearance of rough bumps on the skin and may be accompanied by erythema. Lupus miliaris disseminatus faciei (LMDF) is an uncommon, chronic dermatosis characterized by red-to-yellow or yellow-brown papules of the central face, particularly on and around the eyelids, that may be accompanied by erythema.

As used herein, the term "purpura" refers to any accumulation of blood in the skin due to vascular extravasation, irrespective of size or cause. As used herein, "purpura" refers to medical conditions commonly referred to as "petechiae" (pinpoint spots), "ecchymoses" (larger macular (flat) patches) and "purpura" (larger spots).

Purpura, in general, is hemorrhage of blood out of the vascular spaces and into the skin or surrounding tissues of the skin or mucous membranes. This hemorrhage results in a collection of blood in the dermis and/or subdermal tissues of the skin that is visible initially as a dark purple/red discoloration that changes color as it breaks down and is resorbed.

In particular, purpura can be characterized as flat (macular or non-palpable) or raised (palpable or papular). The definition of macular purpuric subtypes include: petechiae-defined as small purpura (less than 4-5 millimeters (mm) in diameter, purpura-defined as greater than 4-5 mm and less than 1 cm (centimeter) in diameter, and ecchymoses-defined as greater than 1 cm in diameter. The size divisions are not absolute but are useful rules of thumb and there is often a range in size of clinical purpuras in any one specific condition.

A bruise, also called a contusion or ecchymosis, is an injury to biological tissue in which blood vessels such as the capillaries are damaged, allowing blood to seep into the surrounding tissue(s). Bruising is usually caused by a blunt impact and its likelihood and its severity increases as one ages due to thinning and loss of elasticity of the skin.

Certain embodiments herein are directed to pharmaceutical compositions formulated for topical administration of oxymetazoline. In certain embodiments, the pharmaceutical compositions may be creams, and such creams may have any number and quantity of additional components. Certain embodiments of the invention are directed at a cream formulation comprising oxymetazoline from about 0.0075% to about 5% and pharmaceutically acceptable excipients. Some embodiments of the invention are directed at a cream formulation consisting essentially of oxymetazoline from about 0.0075% to about 5% and pharmaceutically acceptable excipients. Some embodiments of the invention are directed at a cream formulation consisting of oxymetazoline from about 0.0075% to about 5% and pharmaceutically acceptable excipients. Such formulations may be used to treat rosacea and symptoms associated with rosacea, including, for example, papules, pustules, phymas (skin thickening), telangiectasias or erythema associated with rosacea, other skin erythemas, telangiectasias, purpura or the like, and other manifestations associated therewith; other inflammatory conditions of the skin including, but not limited to, keratosis pilaris, lupus miliaris dissemniatus faciei, eczema, dermatitis, such as contact dermatitis, atopic dermatitis, seborrheic dermatitis, nummular dermatitis, generalized exfoliative dermatitis, statis dermatitis, neurodermatitis, lichen simplex chronicus, xerosis and xerotic dermatitis, dyshidrosis and dyshidrotic dermatitis, asteototic dermatitis or other conditions characterized by sensitive skin or a disturbance of the epidermal barrier; disorders characterized by rough, dry, cracked or fissured skin, disorders characterized by hyperkeratotic skin such as keratodermas and ichthyosisis and ichthyosiform dermatoses; disorders of hair follicles and sebaceous glands, such as acne, perioral dermatitis, and pseudofolliculitis barbae; disorders of sweat glands, such as miliaria, including, but not limited to, crystallina, miliaria rubra, miliaria profunda, miliaria pustulosa; sunburn, chronic actinic damage, poikiloderma, radiation dermatitis, actinic purpura ("solar purpura"); other inflammatory dermatoses, reactions and conditions of the skin, including, but not limited to, psoriasis, drug eruptions, erythema multiforme, erythema nodosum, and granuloma annulare; diseases and conditions characterized by bleeding or bruising such as petechiae, ecchymosis, purpura and the like including any accumulation of blood in the skin due to vascular extravasation, irrespective of size or cause, bleeding or bruising due to any skin injury which may include any trauma including surgical or procedural trauma; infection, inflammatory dermatoses, inflammation due to any cause or the like. Such formulations may be used to treat or prevent symptoms such as, but not limited to, papules, pustules, other inflammatory lesions, phymas (skin thickening), telangiectasias or erythema associated with rosacea and other inflammatory conditions of the skin including, but not limited to, keratosis pilaris, lupus miliaris dissemniatus faciei, eczema, dermatitis, such as contact dermatitis, atopic dermatitis, seborrheic dermatitis, nummular dermatitis, generalized exfoliative dermatitis, statis dermatitis, neurodermatitis, lichen simplex chronicus, xerosis and xerotic dermatitis, dyshidrosis and dyshidrotic dermatitis, asteototic dermatitis or other conditions characterized by sensitive skin or a disturbance of the epidermal barrier; disorders characterized by rough, dry, cracked or fissured skin, disorders characterized by hyperkeratotic skin such as keratodermas and ichthyosisis and ichthyosiform dermatoses; disorders of hair follicles and sebaceous glands, such as acne, perioral dermatitis, and pseudofolliculitis barbae; disorders of sweat glands, such as miliaria, including, but not limited to, miliaria crystallina, miliaria rubra, miliaria profunda, miliaria pustulosa; sunburn, chronic actinic damage, poikiloderma, radiation dermatitis, actinic purpura ("solar purpura"); other inflammatory dermatoses, reactions and conditions of the skin, including, but not limited to, psoriasis, drug eruptions, erythema multiforme, erythema nodosum, and granuloma annulare; diseases and conditions characterized by bleeding or bruising such as petechiae, ecchymosis, purpura and the like including any accumulation of blood in the skin due to vascular extravasation, irrespective of size or cause, bleeding or bruising due to any skin injury which may include any trauma including surgical or procedural trauma; infection, inflammatory dermatoses or inflammation due to any cause and other skin conditions characterized by increased erythema of the skin. Such formulations may also be used to treat or prevent purpura, which is a hemorrhage of blood out of the vascular spaces and into the skin or surrounding tissues of the skin or mucous membranes. In further embodiments, the formulation is cosmetically acceptable.

Further embodiments are directed to methods of treating erythema, redness or telangiectasias associated with rosacea comprising administering a cream comprising oxymetazoline in a therapeutically effective amount. Some embodiments are directed to methods of treating papules, pustules, and other inflammatory lesions associated with rosacea comprising administering a cream comprising oxymetazoline in a therapeutically effective amount. Some embodiments are directed to methods of treating skin erythema comprising administering a cream comprising oxymetazoline in a therapeutically effective amount. Some embodiments are directed to methods of treating purpura comprising administering a cream comprising oxymetazoline in a therapeutically effective amount. Some embodiments are directed to methods of treating keratosis pilaris, lupus miliaris disseminatus faciei or the like comprising administering a cream comprising oxymetazoline in a therapeutically effective amount. Some embodiments are directed to methods of treating redness or erythema associated with rosacea, skin erythemas, telangiectasias, purpura or the like, and other manifestations associated therewith; other inflammatory conditions of the skin including, but not limited to, keratosis pilaris, lupus miliaris dissemniatus faciei, eczema, dermatitis, such as contact dermatitis, atopic dermatitis, seborrheic dermatitis, nummular dermatitis, generalized exfoliative dermatitis, statis dermatitis, neurodermatitis, lichen simplex chronicus, xerosis and xerotic dermatitis, dyshidrosis and dyshidrotic dermatitis, asteototic dermatitis or other conditions characterized by sensitive skin or a disturbance of the epidermal barrier; disorders characterized by rough, dry, cracked or fissured skin, disorders characterized by hyperkeratotic skin such as keratodermas and ichthyosisis and ichthyosiform dermatoses; disorders of hair follicles and sebaceous glands, such as acne, perioral dermatitis, and pseudofolliculitis barbae; disorders of sweat glands, such as miliaria, including, but not limited to, miliaria crystallina, miliaria rubra, miliaria profunda, miliaria pustulosa; sunburn, chronic actinic damage, poikiloderma, radiation dermatitis, actinic purpura ("solar purpura"); other inflammatory dermatoses, reactions and conditions of the skin, including, but not limited to, psoriasis, drug eruptions, erythema multiforme, erythema nodosum, and granuloma annulare; diseases and conditions characterized by bleeding or bruising such as petechiae, ecchymosis, purpura and the like including any accumulation of blood in the skin due to vascular extravasation, irrespective of size or cause, bleeding or bruising due to any skin injury which may include any trauma including surgical or procedural trauma; infection, inflammatory dermatoses, or inflammation due to any cause. In further embodiments, the formulation is cosmetically acceptable.

Certain embodiments of the invention are directed to methods of treating erythema or redness associated with rosacea comprising administering a cream comprising oxymetazoline in an amount from about 0.0075% to about 5% by weight of the cream and pharmaceutically acceptable excipients. Embodiments are directed to methods of treating inflammatory lesions including papules and pustules associated with rosacea comprising administering a cream comprising oxymetazoline in an amount from about 0.0075% to about 5% by weight of the cream and pharmaceutically acceptable excipients. Embodiments are directed to methods of treating skin thickening (phymas) associated with rosacea comprising administering a cream comprising oxymetazoline in an amount from about 0.0075% to about 5% by weight of the cream and pharmaceutically acceptable excipients. Some embodiments of the invention are directed to methods of treating erythema or redness associated with telangiectasia comprising administering a cream comprising oxymetazoline in an amount from about 0.0075% to about 5% by weight of the cream and pharmaceutically acceptable excipients. Some embodiments of the invention are directed to methods of treating telangiectasia comprising administering a cream comprising oxymetazoline in an amount from about 0.0075% to about 5% by weight of the cream and pharmaceutically acceptable excipients. Some embodiments of the invention are directed to methods of treating erythema or redness associated with erythemato-telangiectatic rosacea comprising administering a cream comprising oxymetazoline in an amount from about 0.0075% to about 5% by weight of the cream. Some embodiments of the invention are directed to methods of treating erythemato-telangiectatic rosacea comprising administering a cream comprising oxymetazoline in an amount from about 0.0075% to about 5% by weight of the cream and pharmaceutically acceptable excipients. Some embodiments of the invention are directed to methods of treating erythema or redness associated with papulopustular rosacea comprising administering a cream comprising oxymetazoline in an amount from about 0.0075% to about 5% by weight of the cream. Some embodiments of the invention are directed to methods of treating papules associated with papulopustular rosacea comprising administering a cream comprising oxymetazoline in an amount from about 0.0075% to about 5% by weight of the cream. Some embodiments of the invention are directed to methods of treating papulopustular rosacea comprising administering a cream comprising oxymetazoline in an amount from about 0.0075% to about 5% by weight of the cream and pharmaceutically acceptable excipients. Embodiments of the invention are directed to methods of treating symptoms associated with rosacea comprising administering a cream comprising oxymetazoline in an amount from about 0.0075% to about 5% by weight of the cream and pharmaceutically acceptable excipients, wherein the symptoms are selected from the group consisting of papules, pustules, erythema (redness), skin thickening and telangiectasias. Some embodiments of the invention are directed to methods of treating purpura comprising administering a cream comprising oxymetazoline in an amount from about 0.0075% to about 5% by weight of the cream and pharmaceutically acceptable excipients. Embodiments are directed to methods of treating keratosis pilaris, lupus miliaris disseminatus faciei or the like comprising administering a cream comprising oxymetazoline in an amount from about 0.0075% to about 5% by weight of the cream and pharmaceutically acceptable excipients. Embodiments are directed to methods of treating rosacea and symptoms associated with rosacea, including, for example, papules, pustules, phymas (skin thickening), telangiectasias or erythema associated with rosacea, other skin erythemas, telangiectasias, purpura or the like, and other manifestations associated therewith; other inflammatory conditions of the skin including, but not limited to, keratosis pilaris, lupus miliaris dissemniatus faciei, eczema, dermatitis, such as contact dermatitis, atopic dermatitis, seborrheic dermatitis, nummular dermatitis, generalized exfoliative dermatitis, statis dermatitis, neurodermatitis, lichen simplex chronicus, xerosis and xerotic dermatitis, dyshidrosis and dyshidrotic dermatitis, asteototic dermatitis or other conditions characterized by sensitive skin or a disturbance of the epidermal barrier; disorders characterized by rough, dry, cracked or fissured skin, disorders characterized by hyperkeratotic skin such as keratodermas and ichthyosisis and ichthyosiform dermatoses; disorders of hair follicles and sebaceous glands, such as acne, perioral dermatitis, and pseudofolliculitis barbae; disorders of sweat glands, such as miliaria, including, but not limited to, miliaria crystallina, miliaria rubra, miliaria profunda, miliaria pustulosa; sunburn, chronic actinic damage, poikiloderma, radiation dermatitis, actinic purpura ("solar purpura"); other inflammatory dermatoses, reactions and conditions of the skin, including, but not limited to, psoriasis, drug eruptions, erythema multiforme, erythema nodosum, and granuloma annulare; diseases and conditions characterized by bleeding or bruising such as petechiae, ecchymosis, purpura and the like including any accumulation of blood in the skin due to vascular extravasation, irrespective of size or cause, bleeding or bruising due to any skin injury which may include any trauma including surgical or procedural trauma; infection, inflammatory dermatoses, inflammation due to any cause comprising administering a cream comprising oxymetazoline in an amount from about 0.0075% to about 5% by weight of the cream and pharmaceutically acceptable excipients. In further embodiments, the formulation is cosmetically acceptable.

Certain embodiments of the invention are directed to methods of treating erythema or redness associated with rosacea comprising administering a cream consisting of oxymetazoline in an amount from about 0.0075% to about 5% by weight of the cream and pharmaceutically acceptable excipients. Some embodiments are directed to methods of treating papules associated with rosacea comprising administering a cream consisting of oxymetazoline in an amount from about 0.0075% to about 5% by weight of the cream and pharmaceutically acceptable excipients. Some embodiments of the invention are directed to methods of treating symptoms associated with rosacea comprising administering a cream consisting of oxymetazoline in an amount from about 0.0075% to about 5% by weight of the cream and pharmaceutically acceptable excipients, wherein the symptoms are selected from the group consisting of papules, pustules, erythema (redness), skin thickening, and telangiectasias. Some embodiments of the invention are directed to methods of treating erythema or redness associated with telangiectasia comprising administering a cream consisting of oxymetazoline in an amount from about 0.0075% to about 5% by weight of the cream and pharmaceutically acceptable excipients. Some embodiments of the invention are directed to methods of treating telangiectasia comprising administering a cream consisting of oxymetazoline in an amount from about 0.0075% to about 5% by weight of the cream and pharmaceutically acceptable excipients. Some embodiments of the invention are directed to methods of treating erythema or redness associated with erythemato-telangiectatic rosacea comprising administering a cream consisting of oxymetazoline in an amount from about 0.0075% to about 5% by weight of the cream and pharmaceutically acceptable excipients. Some embodiments of the invention are directed to methods of treating erythemato-telangiectatic rosacea comprising administering a cream consisting of oxymetazoline in an amount from about 0.0075% to about 5% by weight of the cream and pharmaceutically acceptable excipients. Some embodiments of the invention are directed to methods of treating erythema or redness associated with papulopustular rosacea comprising administering a cream consisting of oxymetazoline in an amount from about 0.0075% to about 5% by weight of the cream. Some embodiments of the invention are directed to methods of treating papules or pustules associated with papulopustular rosacea comprising administering a cream consisting of oxymetazoline in an amount from about 0.0075% to about 5% by weight of the cream. Some embodiments of the invention are directed to methods of treating papulopustular rosacea comprising administering a cream consisting of oxymetazoline in an amount from about 0.0075% to about 5% by weight of the cream and pharmaceutically acceptable excipients. Some embodiments of the invention are directed to methods of treating purpura comprising administering a cream consisting of oxymetazoline in an amount from about 0.0075% to about 5% by weight of the cream and pharmaceutically acceptable excipients. Embodiments are directed to methods of treating rosacea and symptoms associated with rosacea, including, for example, papules, pustules, phymas (skin thickening), telangiectasias or erythema associated with rosacea, other skin erythemas, telangiectasias, purpura or the like, and other manifestations associated therewith; other inflammatory conditions of the skin including, but not limited to, keratosis pilaris, lupus miliaris dissemniatus faciei, eczema, dermatitis, such as contact dermatitis, atopic dermatitis, seborrheic dermatitis, nummular dermatitis, generalized exfoliative dermatitis, statis dermatitis, neurodermatitis, lichen simplex chronicus, xerosis and xerotic dermatitis, dyshidrosis and dyshidrotic dermatitis, asteototic dermatitis or other conditions characterized by sensitive skin or a disturbance of the epidermal barrier; disorders characterized by rough, dry, cracked or fissured skin, disorders characterized by hyperkeratotic skin such as keratodermas and ichthyosisis and ichthyosiform dermatoses; disorders of hair follicles and sebaceous glands, such as acne, perioral dermatitis, and pseudofolliculitis barbae; disorders of sweat glands, such as miliaria, including, but not limited to, miliaria crystallina, miliaria rubra, miliaria profunda, miliaria pustulosa; sunburn, chronic actinic damage, poikiloderma, radiation dermatitis, actinic purpura ("solar purpura"); other inflammatory dermatoses, reactions and conditions of the skin, including, but not limited to, psoriasis, drug eruptions, erythema multiforme, erythema nodosum, and granuloma annulare; diseases and conditions characterized by bleeding or bruising such as petechiae, ecchymosis, purpura and the like including any accumulation of blood in the skin due to vascular extravasation, irrespective of size or cause, bleeding or bruising due to any skin injury which may include any trauma including surgical or procedural trauma; infection, inflammatory dermatoses, inflammation due to any cause comprising administering a cream consisting of oxymetazoline in an amount from about 0.0075% to about 5% by weight of the cream and pharmaceutically acceptable excipients. In further embodiments, the formulation is cosmetically acceptable.

Certain embodiments of the invention are directed to methods of treating erythema or redness associated with rosacea comprising administering a cream consisting essentially of oxymetazoline in an amount from about 0.0075% to about 5% by weight of the cream and pharmaceutically acceptable excipients. Some embodiments are directed to methods of treating papules associated with rosacea comprising administering a cream consisting essentially of oxymetazoline in an amount from about 0.0075% to about 5% by weight of the cream and pharmaceutically acceptable excipients. Some embodiments of the invention are directed to methods of treating symptoms associated with rosacea comprising administering a cream consisting essentially of oxymetazoline in an amount from about 0.0075% to about 5% by weight of the cream and pharmaceutically acceptable excipients, wherein the symptoms are selected from the group consisting of papules, pustules, erythema (redness), skin thickening, and telangiectasias. Some embodiments of the invention are directed to methods of treating erythema or redness associated with telangiectasia comprising administering a cream consisting essentially of oxymetazoline in an amount from about 0.0075% to about 5% by weight of the cream and pharmaceutically acceptable excipients. Some embodiments of the invention are directed to methods of treating telangiectasia comprising administering a cream consisting essentially of oxymetazoline in an amount from about 0.0075% to about 5% by weight of the cream and pharmaceutically acceptable excipients. Some embodiments of the invention are directed to methods of treating erythema or redness associated with erythemato-telangiectatic rosacea comprising administering a cream consisting essentially of oxymetazoline in an amount from about 0.0075% to about 5% by weight of the cream and pharmaceutically acceptable excipients. Some embodiments of the invention are directed to methods of treating erythemato-telangiectatic rosacea comprising administering a cream consisting essentially of oxymetazoline in an amount from about 0.0075% to about 5% by weight of the cream and pharmaceutically acceptable excipients. Some embodiments of the invention are directed to methods of treating erythema or redness associated with papulopustular rosacea comprising administering a cream consisting essentially of oxymetazoline in an amount from about 0.0075% to about 5% by weight of the cream. Some embodiments of the invention are directed to methods of treating papules or pustules associated with papulopustular rosacea comprising administering a cream consisting essentially of oxymetazoline in an amount from about 0.0075% to about 5% by weight of the cream. Some embodiments of the invention are directed to methods of treating papulopustular rosacea comprising administering a cream consisting essentially of oxymetazoline in an amount from about 0.0075% to about 5% by weight of the cream and pharmaceutically acceptable excipients. Some embodiments of the invention are directed to methods of treating purpura comprising administering a cream consisting essentially of oxymetazoline in an amount from about 0.0075% to about 5% by weight of the cream and pharmaceutically acceptable excipients. Some embodiments are directed to methods of treating keratosis pilaris, lupus miliaris disseminatus faciei or the like comprising administering a cream consisting essentially of oxymetazoline in an amount from about 0.0075% to about 5% by weight of the cream and pharmaceutically acceptable excipients. Some embodiments are directed to methods of treating rosacea and symptoms associated with rosacea, including, for example, papules, pustules, phymas (skin thickening), telangiectasias or erythema associated with rosacea, other skin erythemas, telangiectasias, purpura or the like, and other manifestations associated therewith; other inflammatory conditions of the skin including, but not limited to, keratosis pilaris, lupus miliaris dissemniatus faciei, eczema, dermatitis, such as contact dermatitis, atopic dermatitis, seborrheic dermatitis, nummular dermatitis, generalized exfoliative dermatitis, statis dermatitis, neurodermatitis, lichen simplex chronicus, xerosis and xerotic dermatitis, dyshidrosis and dyshidrotic dermatitis, asteototic dermatitis or other conditions characterized by sensitive skin or a disturbance of the epidermal barrier; disorders characterized by rough, dry, cracked or fissured skin, disorders characterized by hyperkeratotic skin such as keratodermas and ichthyosisis and ichthyosiform dermatoses; disorders of hair follicles and sebaceous glands, such as acne, perioral dermatitis, and pseudofolliculitis barbae; disorders of sweat glands, such as miliaria, including, but not limited to, miliaria crystallina, miliaria rubra, miliaria profunda, miliaria pustulosa; sunburn, chronic actinic damage, poikiloderma, radiation dermatitis, actinic purpura ("solar purpura"); other inflammatory dermatoses, reactions and conditions of the skin, including, but not limited to, psoriasis, drug eruptions, erythema multiforme, erythema nodosum, and granuloma annulare; diseases and conditions characterized by bleeding or bruising such as petechiae, ecchymosis, purpura and the like including any accumulation of blood in the skin due to vascular extravasation, irrespective of size or cause, bleeding or bruising due to any skin injury which may include any trauma including surgical or procedural trauma; infection, inflammatory dermatoses, inflammation due to any cause comprising administering a cream consisting essentially of oxymetazoline in an amount from about 0.0075% to about 5% by weight of the cream and pharmaceutically acceptable excipients. In further embodiments, the formulation is cosmetically acceptable.

Oxymetazoline is the common name for 3-(4,5-dihydro-1H-imidazol-2-ylmethyl)-2,4-dimethyl-6-tert-butyl-phenol, which has the chemical structure:

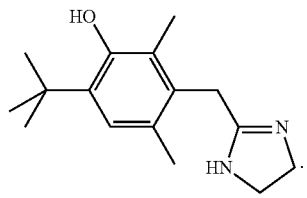 [SMILES: Cc1cc(C(C)(C)C)c(O)c(C)c1CC1=NCCN1]

As used herein, oxymetazoline includes both oxymetazoline free base and an acid addition salt of oxymetazoline. For example, in some embodiments, the oxymetazoline used in the preparation of the pharmaceutical composition may include a pharmaceutical salt, such as hydrochloric acid, hydrobromic acid, sulfuric acid, nitric acid, carbonic acid, phosphoric acid, and the like, or an organic acid such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid, and the like. In certain embodiments, the pharmaceutical salt may be hydrochloric acid A "cream," as used herein, refers to a semi-solid emulsion, i.e. a dispersed system having at least two immiscible phases where one phase is dispersed in another, with droplets ranging in diameter from about 0.1 µm to about 100 µm that is capable of penetrating the stratum corneum layer of skin. The creams of various embodiments can have a viscosity of from about 2,500 centipoises (cP) to about 150,000 cP at about 25° C. In some embodiments, the creams described herein can exhibit a melting point of greater than about 25° C., greater than about 30° C., greater than about 35° C., greater than about 40° C., from about 25° C. to about 80° C., from about 25° C. to about 60° C., from about 30° C. to about 80° C., from about 30° C. to about 60° C., from about 35° C. to about 80° C., from about 35° C. to about 60° C., from about 35° C. to about 50° C., from about 35° C. to about 40° C., from about 40° C. to about 80° C., or from about 40° C. to about 60° C.

In certain embodiments of the present invention a cream comprising oxymetazoline, as the active pharmaceutical ingredient (API), and pharmaceutically acceptable excipients is provided. In some embodiments, the cream may comprise from about 0.0075% to about 5%, from about 0.0075% to about 2.5%, from about 0.0075% to about 2%, from about 0.0075% to about 1.5%, from about 0.0075% to about 1%, from about 0.0075% to about 0.5%, from about 0.0075% to about 0.25%, from about 0.0075% to about 0.15%, from about 0.0075% to about 0.1%, from about 0.0075% to about 0.025%, from about 0.0075% to about 0.075%, from about 0.0075% to about 0.06%, from about 0.0075% to about 0.05%, from about 0.01% to about 5%, from about 0.01% to about 2.5%, from about 0.01% to about 2%, from about 0.01% to about 1.5%, from about 0.01% to about 1%, from about 0.01% to about 0.5%, from about 0.01% to about 0.25%, from about 0.01% to about 0.15%, from about 0.01% to about 0.1%, from about 0.01% to about 0.025%, from about 0.05% to about 5%, from about 0.05% to about 2.5%, from about 0.05% to about 2%, from about 0.05% to about 1%, from about 0.05% to about 0.5%, from about 0.05% to about 0.25%, from about 0.05% to about 0.15%, from about 0.05% to about 0.1%, from about 0.05% to about 0.075% from about 0.1% to about 5%, from about 0.1% to about 2.5%, from about 0.1% to about 2%, from about 0.1% to about 1.5%, from about 0.1% to about 1%, from about 0.1% to about 0.5%, from about 0.1% to about 0.25%, from about 0.1% to about 0.15%, from about 0.15% to about 5%, from about 0.15% to about 2.5%, from about 0.15% to about 2%, from about 0.15% to about 1.5%, from about 0.15% to about 1%, from about 0.15% to about 0.5%, from about 0.15% to about 0.25% by weight of oxymetazoline and pharmaceutically acceptable excipients. In some embodiments, the cream may comprise about 0.0075%, about 0.01%, about 0.025%, about 0.05%, about 0.06%, about 0.075%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1%, about 1.05%, about 1.1%, about 1.15%, about 1.2%, about 1.25%, about 1.3%, about 1.35%, about 1.4%, about 1.45%, about 1.5%, about 1.55%, about 1.6%, about 1.65%, about 1.7%, about 1.75%, about 1.8%, about 1.85%, about 1.9%, about 1.95%, about 2%, about 2.05%, about 2.1%, about 2.15%, about 2.2%, about 2.25%, about 2.3%, about 2.35%, about 2.4%, about 2.45%, about 2.5%, about 2.55%, about 2.6%, about 2.65%, about 2.7%, about 2.75%, about 2.8%, about 2.85%, about 2.9%, about 2.95%, about 3%, about 3.5%, about 4%, about 4.5%, or about 5% by weight of oxymetazoline and pharmaceutically acceptable excipients. In some embodiments, the cream may comprise less than about 5% by weight of oxymetazoline and pharmaceutically acceptable excipients. In some embodiments, the cream may comprise less than about 2.5% by weight of oxymetazoline and pharmaceutically acceptable excipients. In some embodiments, the cream may comprise less than about 2% by weight of oxymetazoline and pharmaceutically acceptable excipients. In some embodiments, the cream may comprise less than about 1% by weight of oxymetazoline and pharmaceutically acceptable excipients. In certain embodiments, a cream comprising oxymetazoline, a vasoconstrictor and pharmaceutically acceptable excipients is provided. In certain embodiments, a cream comprising oxymetazoline, an alpha-adrenergic agonist and pharmaceutically acceptable excipients is provided. In certain embodiments, a cream comprising oxymetazoline, an imidazoline alpha-adrenergic agonist and pharmaceutically acceptable excipients is provided. In certain embodiments, a cream comprising oxymetazoline, a non-imidazoline alpha-adrenergic agonist and pharmaceutically acceptable excipients is provided. In certain embodiments, a cream comprising oxymetazoline, an alpha-1 adrenergic agonist and pharmaceutically acceptable excipients is provided. In certain embodiments, a cream comprising oxymetazoline, an alpha-2 adrenergic agonist and pharmaceutically acceptable excipients is provided. In certain embodiments, a cream comprising oxymetazoline, a selective alpha-adrenergic agonist and pharmaceutically acceptable excipients is provided. In certain embodiments, a cream comprising oxymetazoline, a non-selective alpha-adrenergic agonist and pharmaceutically acceptable excipients is provided. In certain embodiments, a cream comprising oxymetazoline, a selective alpha-1 adrenergic agonist and pharmaceutically acceptable excipients is provided. In certain embodiments, a cream comprising oxymetazoline, a selective alpha-2 adrenergic agonist and pharmaceutically acceptable excipients is provided. In certain embodiments, a cream comprising oxymetazoline, a non-selective alpha-1 adrenergic agonist and pharmaceutically acceptable excipients is provided. In certain embodiments, a cream comprising oxymetazoline, a non-selective alpha-2 adrenergic agonist and pharmaceutically acceptable excipients is provided.

In certain embodiments of the present invention a cream consisting essentially of oxymetazoline and pharmaceutically acceptable excipients is provided. In some embodiments, the cream may consist essentially of from about 0.0075% to about 5%, from about 0.0075% to about 2.5%, from about 0.0075% to about 2%, from about 0.0075% to about 1.5%, from about 0.0075% to about 1%, from about 0.0075% to about 0.5%, from about 0.0075% to about 0.25%, from about 0.0075% to about 0.15%, from about 0.0075% to about 0.1%, from about 0.0075% to about 0.025%, from about 0.0075% to about 0.075%, from about 0.0075% to about 0.06%, from about 0.0075% to about 0.05%, from about 0.01% to about 5%, from about 0.01% to about 2.5%, from about 0.01% to about 2%, from about 0.01% to about 1.5%, from about 0.01% to about 1%, from about 0.01% to about 0.5%, from about 0.01% to about 0.25%, from about 0.01% to about 0.15%, from about 0.01% to about 0.1%, from about 0.01% to about 0.025%, from about 0.05% to about 5%, from about 0.05% to about 2.5%, from about 0.05% to about 2%, from about 0.05% to about 1.5%, from about 0.05% to about 1%, from about 0.05% to about 0.5%, from about 0.05% to about 0.25%, from about 0.05% to about 0.15%, from about 0.05% to about 0.1%, from about 0.05% to about 0.075% from about 0.1% to about 5%, from about 0.1% to about 2.5%, from about 0.1% to about 2%, from about 0.1% to about 1.5%, from about 0.1% to about 1%, from about 0.1% to about 0.5%, from about 0.1% to about 0.25%, from about 0.1% to about 0.15%, from about 0.15% to about 5%, from about 0.15% to about 2.5%, from about 0.15% to about 2%, from about 0.15% to about 1.5%, from about 0.15% to about 1%, from about 0.15% to about 0.5%, from about 0.15% to about 0.25% by weight of oxymetazoline and pharmaceutically acceptable excipients. In some embodiments, the cream may consist essentially of about 0.0075%, about 0.01%, about 0.025%, about 0.05%, about 0.06%, about 0.075%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1%, about 1.05%, about 1.1%, about 1.15%, about 1.2%, about 1.25%, about 1.3%, about 1.35%, about 1.4%, about 1.45%, about 1.5%, about 1.55%, about 1.6%, about 1.65%, about 1.7%, about 1.75%, about 1.8%, about 1.85%, about 1.9%, about 1.95%, about 2%, about 2.05%, about 2.1%, about 2.15%, about 2.2%, about 2.25%, about 2.3%, about 2.35%, about 2.4%, about 2.45%, about 2.5%, about 2.55%, about 2.6%, about 2.65%, about 2.7%, about 2.75%, about 2.8%, about 2.85%, about 2.9%, about 2.95%, about 3%, about 3.5%, about 4%, about 4.5%, or about 5% by weight of oxymetazoline and pharmaceutically acceptable excipients. In some embodiments, the cream may consist essentially of less than about 5% by weight of oxymetazoline and pharmaceutically acceptable excipients. In some embodiments, the cream may consist essentially of less than about 2.5% by weight of oxymetazoline and pharmaceutically acceptable excipients. In some embodiments, the cream may consist essentially of less than about 2% by weight of oxymetazoline and pharmaceutically acceptable excipients. In some embodiments, the cream may consist essentially of less than about 1% by weight of oxymetazoline and pharmaceutically acceptable excipients. In certain embodiments, a cream consisting essentially of oxymetazoline, a vasoconstrictor and pharmaceutically acceptable excipients is provided. In certain embodiments, a cream consisting essentially of oxymetazoline, an alpha-adrenergic agonist and pharmaceutically acceptable excipients is provided. In certain embodiments, a cream consisting essentially of oxymetazoline, an imidazoline alpha-adrenergic agonist and pharmaceutically acceptable excipients is provided. In certain embodiments, a cream consisting essentially of oxymetazoline, a non-imidazoline alpha-adrenergic agonist and pharmaceutically acceptable excipients is provided. In certain embodiments, a cream consisting essentially of oxymetazoline, an alpha-1 adrenergic agonist and pharmaceutically acceptable excipients is provided. In certain embodiments, a cream consisting essentially of oxymetazoline, an alpha-2 adrenergic agonist and pharmaceutically acceptable excipients is provided. In certain embodiments, a cream consisting essentially of oxymetazoline, a selective alpha-adrenergic agonist and pharmaceutically acceptable excipients is provided. In certain embodiments, a cream consisting essentially of oxymetazoline, a non-selective alpha-adrenergic agonist and pharmaceutically acceptable excipients is provided. In certain embodiments, a cream consisting essentially of oxymetazoline, a selective alpha-1 adrenergic agonist and pharmaceutically acceptable excipients is provided. In certain embodiments, a cream consisting essentially of oxymetazoline, a selective alpha-2 adrenergic agonist and pharmaceutically acceptable excipients is provided. In certain embodiments, a cream consisting essentially of oxymetazoline, a non-selective alpha-1 adrenergic agonist and pharmaceutically acceptable excipients is provided. In certain embodiments, a cream consisting essentially of oxymetazoline, a non-selective alpha-2 adrenergic agonist and pharmaceutically acceptable excipients is provided.

In certain embodiments of the present invention a cream consisting of oxymetazoline and pharmaceutically acceptable excipients is provided. In some embodiments, the cream may consist of from about 0.0075% to about 5%, from about 0.0075% to about 2.5%, from about 0.0075% to about 2%, from about 0.0075% to about 1.5%, from about 0.0075% to about 1%, from about 0.0075% to about 0.5%, from about 0.0075% to about 0.25%, from about 0.0075% to about 0.15%, from about 0.0075% to about 0.1%, from about 0.0075% to about 0.025%, from about 0.0075% to about 0.075%, from about 0.0075% to about 0.06%, from about 0.0075% to about 0.05%, from about 0.01% to about 5%, from about 0.01% to about 2.5%, from about 0.01% to about 2%, from about 0.01% to about 1.5%, from about 0.01% to about 1%, from about 0.01% to about 0.5%, from about 0.01% to about 0.25%, from about 0.01% to about 0.15%, from about 0.01% to about 0.1%, from about 0.01% to about 0.025%, from about 0.05% to about 5%, from about 0.05% to about 2.5%, from about 0.05% to about 2%, from about 0.05% to about 1.5%, from about 0.05% to about 1%, from about 0.05% to about 0.5%, from about 0.05% to about 0.25%, from about 0.05% to about 0.15%, from about 0.05% to about 0.1%, from about 0.05% to about 0.075% from about 0.1% to about 5%, from about 0.1% to about 2.5%, from about 0.1% to about 2%, from about 0.1% to about 1.5%, from about 0.1% to about 1%, from about 0.1% to about 0.5%, from about 0.1% to about 0.25%, from about 0.1% to about 0.15%, from about 0.15% to about 5%, from about 0.15% to about 2.5%, from about 0.15% to about 2%, from about 0.15% to about 1.5%, from about 0.15% to about 1%, from about 0.15% to about 0.5%, from about 0.15% to about 0.25% by weight of oxymetazoline and pharmaceutically acceptable excipients. In some embodiments, the cream may consist of about 0.0075%, about 0.01%, about 0.025%, about 0.05%, about 0.06%, about 0.075%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1%, about 1.05%, about 1.1%, about 1.15%, about 1.2%, about 1.25%, about 1.3%, about 1.35%, about 1.4%, about 1.45%, about 1.5%, about 1.55%, about 1.6%, about 1.65%, about 1.7%, about 1.75%, about 1.8%, about 1.85%, about 1.9%, about 1.95%, about 2%, about 2.05%, about 2.1%, about 2.15%, about 2.2%, about 2.25%, about 2.3%, about 2.35%, about 2.4%, about 2.45%, about 2.5%, about 2.55%, about 2.6%, about 2.65%, about 2.7%, about 2.75%, about 2.8%, about 2.85%, about 2.9%, about 2.95%, about 3%, about 3.5%, about 4%, about 4.5%, or about 5% by weight of oxymetazoline and pharmaceutically acceptable excipients. In some embodiments, the cream may consist of less than about 5% by weight of oxymetazoline and pharmaceutically acceptable excipients. In some embodiments, the cream may consist of less than about 2.5% by weight of oxymetazoline and pharmaceutically acceptable excipients. In some embodiments, the cream may consist of less than about 2% by weight of oxymetazoline and pharmaceutically acceptable excipients. In some embodiments, the cream may consist of less than about 1% by weight of oxymetazoline and pharmaceutically acceptable excipients. In certain embodiments, a cream consisting of oxymetazoline, a vasoconstrictor and pharmaceutically acceptable excipients is provided. In certain embodiments, a cream consisting of oxymetazoline, an adrenomimetic and pharmaceutically acceptable excipients is provided. In certain embodiments, a cream consisting of oxymetazoline, an alpha-adrenergic agonist and pharmaceutically acceptable excipients is provided. In certain embodiments, a cream consisting of oxymetazoline, an imidazoline alpha-adrenergic agonist and pharmaceutically acceptable excipients is provided. In certain embodiments, a cream consisting of oxymetazoline, a non-imidazoline alpha-adrenergic agonist and pharmaceutically acceptable excipients is provided. In certain embodiments, a cream consisting of oxymetazoline, an alpha-1 adrenergic agonist and pharmaceutically acceptable excipients is provided. In certain embodiments, a cream consisting of oxymetazoline, an alpha-2 adrenergic agonist and pharmaceutically acceptable excipients is provided. In certain embodiments, a cream consisting of oxymetazoline, a selective alpha-adrenergic agonist and pharmaceutically acceptable excipients is provided. In certain embodiments, a cream consisting of oxymetazoline, a non-selective alpha-adrenergic agonist and pharmaceutically acceptable excipients is provided. In certain embodiments, a cream consisting of oxymetazoline, a selective alpha-1 adrenergic agonist and pharmaceutically acceptable excipients is provided. In certain embodiments, a cream consisting of oxymetazoline, a selective alpha-2 adrenergic agonist and pharmaceutically acceptable excipients is provided. In certain embodiments, a cream consisting of oxymetazoline, a non-selective alpha-1 adrenergic agonist and pharmaceutically acceptable excipients is provided. In certain embodiments, a cream consisting of oxymetazoline, a non-selective alpha-2 adrenergic agonist and pharmaceutically acceptable excipients is provided.

In some embodiments, the cream may comprise an API other than oxymetazoline in an amount that is clinically effective. In some embodiments, the cream may comprise from about 0.0075% to about 50%, from about 0.0075% to about 40%, from about 0.0075% to about 35%, from about 0.0075% to about 30%, from about 0.0075% to about 25%, from about 0.0075% to about 20%, from about 0.0075% to about 15%, from about 0.0075% to about 10%, from about 0.0075% to about 5%, from about 0.0075% to about 4%, from about 0.0075% to about 3%, from about 0.0075% to about 2.5%, from about 0.0075% to about 2%, from about 0.0075% to about 1%, from about 0.0075% to about 0.5%, from about 0.0075% to about 0.25%, from about 0.0075% to about 0.15%, from about 0.0075% to about 0.1%, from about 0.0075% to about 0.075%, from about 0.0075% to about 0.06%, from about 0.0075% to about 0.05%, from about 0.0075% to about 0.025%, from about 0.01% to about 40%, from about 0.01% to about 35%, from about 0.01% to about 30%, from about 0.01% to about 25%, from about 0.01% to about 20%, from about 0.01% to about 15%, from about 0.01% to about 10%, from about 0.01% to about 5%, from about 0.01% to about 4%, from about 0.01% to about 3%, from about 0.01% to about 2.5%, from about 0.01% to about 2%, from about 0.01% to about 1%, from about 0.01% to about 0.5%, from about 0.01% to about 0.25%, from about 0.01% to about 0.15%, from about 0.01% to about 0.1%, from about 0.01% to about 0.05%, from about 0.01% to about 0.025%, from about 0.05% to about 40%, from about 0.05% to about 35%, from about 0.05% to about 30%, from about 0.05% to about 25%, from about 0.05% to about 20%, from about 0.05% to about 15%, from about 0.05% to about 10%, from about 0.05% to about 5%, from about 0.05% to about 4%, from about 0.05% to about 3%, from about 0.05% to about 2.5%, from about 0.05% to about 2%, from about 0.05% to about 1%, from about 0.05% to about 0.5%, from about 0.05% to about 0.25%, from about 0.05% to about 0.15%, from about 0.05% to about 0.1%, from about 0.05% to about 0.075%, from about 0.1% to about 40%, from about 0.1% to about 35%, from about 0.1% to about 30%, from about 0.1% to about 25%, from about 0.1% to about 20%, from about 0.1% to about 15%, from about 0.1% to about 10%, from about 0.1% to about 5%, from about 0.1% to about 4%, from about 0.1% to about 3%, from about 0.1% to about 2.5%, from about 0.1% to about 2%, from about 0.1% to about 1%, from about 0.1% to about 0.5%, from about 0.1% to about 0.25%, from about 0.1% to about 0.15%, from about 0.15% to about 40%, from about 0.15% to about 35%, from about 0.15% to about 30%, from about 0.15% to about 25%, from about 0.15% to about 20%, from about 0.15% to about 15%, from about 0.15% to about 10%, from about 0.15% to about 5%, from about 0.15% to about 4%, from about 0.15% to about 3%, from about 0.15% to about 2.5%, from about 0.15% to about 2%, from about 0.15% to about 1%, from about 0.15% to about 0.5%, from about 0.15% to about 0.25% by weight of an API other than oxymetazoline and pharmaceutically acceptable excipients. In some embodiments, the cream may comprise about 0.0075%, about 0.01%, about 0.025%, about 0.05%, about 0.06%, about 0.075%, about 0.1%, about 0.15%, about 0.2%, about 0.25%, about 0.3%, about 0.35%, about 0.4%, about 0.45%, about 0.5%, about 0.75%, about 1%, about 2%, about 2.5% or about 5% by weight of an API other than oxymetazoline and pharmaceutically acceptable excipients.

In certain embodiments, a cream comprising an API other than oxymetazoline, an alpha-adrenergic agonist and pharmaceutically acceptable excipients is provided. In certain embodiments, a cream comprising an API other than oxymetazoline, an imidazoline alpha-adrenergic agonist and pharmaceutically acceptable excipients is provided. In certain embodiments, a cream comprising an API other than oxymetazoline, a non-imidazoline alpha-adrenergic agonist and pharmaceutically acceptable excipients is provided. In certain embodiments, a cream comprising an API other than oxymetazoline, an alpha-1 adrenergic agonist and pharmaceutically acceptable excipients is provided. In certain embodiments, a cream comprising an API other than oxymetazoline, an alpha-2 adrenergic agonist and pharmaceutically acceptable excipients is provided. In certain embodiments, a cream comprising an API other than oxymetazoline, a selective alpha-adrenergic agonist and pharmaceutically acceptable excipients is provided. In certain embodiments, a cream comprising an API other than oxymetazoline, a non-selective alpha-adrenergic agonist and pharmaceutically acceptable excipients is provided. In certain embodiments, a cream comprising an API other than oxymetazoline, a selective alpha-1 adrenergic agonist and pharmaceutically acceptable excipients is provided. In certain embodiments, a cream comprising an API other than oxymetazoline, a selective alpha-2 adrenergic agonist and pharmaceutically acceptable excipients is provided. In certain embodiments, a cream comprising an API other than oxymetazoline, a non-selective alpha-1 adrenergic agonist and pharmaceutically acceptable excipients is provided. In certain embodiments, a cream comprising an API other than oxymetazoline, a non-selective alpha-2 adrenergic agonist and pharmaceutically acceptable excipients is provided.

In certain embodiments, the cream may comprise a formulation having a buffer system. In some embodiments, the cream may comprise a buffering agent. In some embodiments, the buffering agent may be selected from a group consisting of citric acid, sodium citrate, sodium lactate, ammonium hydroxide, trizma acetate, sodium borate, acetic acid, sodium acetate, phosphoric acid, sodium phosphate, sodium citrate dehydrate and the like. In certain embodiments, the buffer capacity may be from about 0 mM to about 600 mM; from about 0 mM to about 600 mM; from about 5 mM to about 600 mM; from about 5 mM to about 400 mM; from about 5 mM to about 300 mM; from about 5 mM to about 200 mM; from about 200 mM to about 400 mM; about 0 mM, about 100 mM, about 200 mM, about 300 mM, about 400 mM, about 500 mM, or about 600 mM.

In certain embodiments, the cream may comprise the formulation of any of Trials 1-51 described herein with oxymetazoline as the API. In other embodiments the cream may comprise the formulation of any of Trials 1-51 with an API other than oxymetazoline. In certain embodiments of the present invention, the cream may comprise the formulation of any of Trials 22, 24, 25, or 35-51 as described herein. In one embodiment of the present invention, the cream consists essentially of the formulation of any of Trials 22, 24, 25, or 35-51 as described herein. In one embodiment of the present invention, the cream consists of the formulation of any of Trials 22, 24, 25, or 35-51 as described herein. In some embodiments, the cream formulation comprises Trial 38 as a base formulation.

In certain embodiments the cream formulations are not only "non-irritating" to the sensitive skin of patients with rosacea, but are calming, or "soothing" to the skin. In addition, the calming or soothing and moisturizing effect of the cream formulation of certain embodiments herein may last for an extended period of time. In some embodiments, the soothing effect may last up to at least about four hours, at least about five hours, at least about six hours, at least about seven hours, at least about eight hours, at least about ten hours, at least about 12 hours, at least about 15 hours, at least about 18 hours, at least about 21 hours, at least about 24 hours, or at least about 48 hours with a single application. In some embodiments, the soothing effect may last for from about 1 to about 48 hours; from about 1 to about 24 hours; from about 1 to about 21 hours; from about 1 to about 18 hours; from about 1 to about 16 hours; from about 1 to about 12 hours; from about 1 to about 10 hours; from about 1 to about 8 hours; from about 2 to about 824 hours; from about 2 to about 16 hours; from about 2 to about 12 hours; from about 2 to about 8 hours; from about 4 to about 24 hours; from about 4 to about 16 hours; from about 4 to about 12 hours; from about 4 to about 8 hours; from about 6 to about 24 hours; from about 6 to about 16 hours; from about 6 to about 12 hours; from about 4 to about 8 hours; from about 6 to about 8 hours; from about 2 to about 6 hours; from about 4 to about 6 hours, or combinations thereof. In some embodiments, this soothing effect may be maintained with daily application of the cream formulation to the skin. In some embodiments, this soothing effect may be maintained for as long as the cream formulation is applied to the skin daily. In some embodiments, this soothing effect may be maintained with daily application of the cream formulation for at least about 1 month, at least about 2 months, at least about 3 months, at least about 4 months, at least about 5 months, at least about 6 months, at least about 9 months, or at least about 12 months.

The cream formulation of certain embodiments is cosmetically acceptable to both patients with rosacea, a disorder characterized by a defect in the epidermal barrier and by normal controls.

In certain embodiments the cream formulation is a soothing, long-lasting moisturizer that is cosmetically elegant and well tolerated even in subjects with extremely sensitive and highly reactive skin.

In some embodiments, the cream may include an emulsifying agent, or emulsifier. The emulsifier can be provided to adjust the properties of the cream, such as density, viscosity, the melting point, and/or droplet size; and in some embodiments, the emulsifier may increase the stability of the cream. Various emulsions suitable for embodiments described herein and methods for preparing such emulsions are well known in the art and are described in, for example, Remington's Pharmaceutical Sciences, Mack Publishing Co., Easton, Pa., USA, which is hereby incorporated by reference in its entirety. In some embodiments, the cream may include an emulsifier in an amount from about 1% to about 30%, from about 1% to about 25%, from about 1% to about 20%, or from about 4% to about 12% emulsifier. In some embodiments, the cream may include emulsifier in an amount greater than 8%. In some embodiments, the cream may include from about 8% to about 30% emulsifier. In some embodiments, the cream may include from about 8% to about 25% emulsifier. In other embodiments, the cream may include from about 8% to about 20% emulsifier. In still other embodiments, the cream may include from about 8% to about 10% emulsifier. If more than one emulsifier is used, the cream may include from about 1% to about 30% of each emulsifier, from about 2% to about 30% of each emulsifier or from about 2% to about 25% of each emulsifier.

The creams of various embodiments may include any emulsifiers or combination of emulsifiers. For example, in some embodiments, the cream may be a common oil-in-water or water-in-oil emulsion including oxymetazoline and water or one or more common oils such as, for example, cottonseed, groundnut, corn, germ, olive, castor, soybean, mineral, and sesame oils. In other embodiments, the cream may include one or more emulsifiers, such as, for example, sesquioleates such as sorbitan sesquioleate or polyglyceryl-2-sesquioleate, ethoxylated esters of derivatives of natural oils such as the polyethoxylated ester of hydrogenated castor oil, silicone emulsifiers such as silicone polyols, anionic emulsifiers, fatty acid soaps such as potassium stearate and fatty acid sulphates like sodium cetostearyl sulphate, ethoxylated fatty alcohols, sorbitan esters, ethoxylated sorbitan esters, ethoxylated fatty acid esters such as ethoxylated stearates, ethoxylated mono-, di-, and triglycerides, non-ionic self-emulsifying waxes, ethoxylated fatty acids, methylglucose esters such as polyglycerol-3 methyl glucose distearate, and mixtures thereof. In particular embodiments, the emulsifier may be an ethoxylated fatty acid such as, for example, the mixture of PEG-6/PEG-32/glycol stearate marketed under the trademark TEFOSE™ 63 by Gattefosse. As used herein, TEFOSE™ 63 is considered an emulsifier and, in certain embodiments described herein, shall be considered a mixture of one or more polyethylene glycol (PEG) stearates and one or more glycol stearates. In some embodiments, the emulsifier may comprise a polyethylene glycol (PEG) stearate, a glycol stearate or a mixture thereof. In some embodiments, the cream may include from about 1% to about 30% TEFOSE™ 63. In some embodiments, the cream may include from about 1% to about 20% TEFOSE™ 63. In other embodiments, the cream may include from about 1% to less than about 20% TEFOSE™ 63. In embodiments, the cream may include from about 4% to about 12% TEFOSE™ 63. In some embodiments, the cream may include greater than about 8% TEFOSE™ 63. In other embodiments, the cream may include from about 8% to about 10% TEFOSE™. In still other embodiments, the cream may include from about 8% to less than about 10% TEFOSE™ 63. In some embodiments, the cream may comprise TEFOSE™ 63 in an amount from about 1% to about 20%. In various embodiments, the cream may comprise TEFOSE™ 63 in an amount from about 3% to about 15%, from about 5% to about 10%, from about 7% to about 10%, about 9% or about 8%. In some embodiments the cream may comprise about 7.1%, about 7.2%, about 7.3%, about 7.4%, about 7.5%, about 7.6%, about 7.7%, about 7.8%, about 7.9%, about 8%, about 8.1%, about 8.2%, about 8.3%, about 8.4%, or about 8.5% by weight of TEFOSE™ 63. In certain embodiments, TEFOSE™ 63 is comprised of PEG-6 stearate, glycol stearate, and PEG-32 stearate. In embodiments, the cream comprises PEG-6 stearate, glycol stearate, and PEG-32 stearate added as TEFOSE™ 63 in an about from about 1% to about 20%, from about 3% to about 15%, from about 5% to about 10%, from about 7% to about 10%, about 9% or about 8%. In some embodiments, the cream comprises PEG-6 stearate, glycol stearate and PEG-32 stearate. In embodiments, the cream may comprise PEG-6 stearate, glycol stearate and PEG-32 stearate in a ratio of about 63:18.5:18.5, about 75:12.5:12.5, about 50:25:25, about 75:15:10 or ranges of such ratios. In embodiments, the cream may comprise PEG-6 stearate, glycol stearate and PEG-32 stearate in a combined amount of from about 1% to about 30%, from about 1% to about 20%, from about 3% to about 15%, from about 5% to about 10%, from about 7% to about 10%, about 9% or about 8%. In embodiments, the cream may comprise PEG-6 stearate in an about from about 1% to about 20% by weight, from about 1% to about 10% by weight, from about 4% to about 10% by weight or from about 4% to about 6% by weight. In some embodiments, the cream may comprise glycol stearate in an amount from about 0.1% to about 10%, from about 0.1% to about 8%, from about 0.5% to about 5%, from about 0.5% to about 3%, from about 0.5% to about 2%, or from about 0.8% to about 2%. In some embodiments, the cream may comprise PEG-32 stearate in an amount from about 0.1% to about 10%, from about 0.1% to about 8%, from about 0.5% to about 5%, from about 0.5% to about 3%, from about 0.5% to about 2%, or from about 0.8% to about 2%. In some embodiments, the cream may comprise PEG-6 may be present in an amount of about 5% w/w; glycol stearate may be present in an amount of about 1.5% w/w, PEG-32 stearate may be present in an amount of about 1.5% w/w.

In some embodiments, the hydrophilic-lipophilic balance ("HLB") of the oil phase (or internal phase) of the cream may be very closely matched with the HLB values of the blend of emulsifiers in the cream. For example, the ingredients in the oil phase may include HLB values of:

| Ingredient | HLB value* |
|---|---|
| Medium chain triglycerides | 10.0 |
| diisopropyl adipate | 9.0 |
| oleyl alcohol | 14.0 |
| lanolin | 12.0 |

*HLB values are approximate and may vary by about ±1 unit.

Also, as example, the blend of emulsifiers may include HLB values of:

| Ingredient | HLB value* |
|---|---|
| TEFOSE ™ 63 | 9.0-10.0 |
| cetostearyl alcohol | 15.5 |
| Macrogol (6) cetostearyl ether | 10.0-12.0 |
| Macrogol (25) cetostearyl ether | 15.0-17.0 |

*HLB values are approximate and may vary by about ±1 unit.

In some embodiments, the cream may comprise an emulsifier having a hydrophilic-lipophilic balance of from about 9.0 to about 17.0. In some embodiments, the hydrophilic-lipophilic balance is determined by Griffin's method. For example, in Trial 38, the HLB values for the oil phase and the emulsifier blend is as follows:

| Oil Phase | | | |
|---|---|---|---|
| Component | Desired HLB | Percent in Formula | Contribution |
| Medium chain triglycerides | 10.0 | 7.0 | 0.70 |
| Diisopropyl adipate | 9.0 | 7.0 | 0.63 |
| Oleyl alcohol | 14.0 | 7.0 | 0.98 |
| Lanolin | 12.0 | 2.0 | 0.24 |
| | | Oil Phase SUM | 2.55 |
| Emulifier Blend | | | |
| Component | HLB Value* | Percent in Formula | Contribution |
| Tefose 63 | 9 to 10 | 8.0 | 0.76 |
| Cetostearyl alcohol | 15.5 | 8.0 | 1.24 |
| Macrogol (6) cetostearyl ether | 10 to 12 | 2.0 | 0.22 |
| Macrogol (25) cetostearyl ether | 15 to 17 | 2.0 | 0.32 |
| | | Emulsifier Blend SUM | 2.54 |

*For HLB value ranges, the mid value was used to execute the calculation.

It may be understood from the above calculations that where percentages of the oil phase ingredients are varied, physically stable emulsions may be obtained by varying the percentages of blend emulsifiers so that the required HLB of the oil phase remains closely matched. In embodiments, the HLB may be matched within +/−1 HLB value, within +/−0.5 HLB value or within +/−0.1 HLB value.

Without wishing to be bound by theory, it is surprising that, for example, in Trial 38, using four neutral to hydrophilic emulsifiers, such as TEFOSE 63™ (having an HLB value from about 9.0 to about 10.0) or Macrogol (25) cetostearyl ether (having an HLB value from about 15.0 to about 17.0), in the concentrations or proportions described, results in a cosmetically acceptable emulsion that is non-irritating. Nonionic surfactants such as those used in embodiments herein may contain irritants such as polyethylene glycol (PEG). Such PEGylated or PEG containing surfactants may be irritating and may cause contact dermatitis at high levels. In some embodiments, the cream formulation may comprise an emulsifier having an HLB value of from about 9.0 to about 17.0 in cream embodiments described herein wherein the cream formulation is cosmetically acceptable and non-irritating. In embodiments, the cream formulation may be non-irritating to even patients with extremely reactive and/or sensitive skin, such as, but not limited to, that typically seen in patients with rosacea, eczema, dermatitis, and other conditions of the skin characterized by a disturbance of the epidermal barrier.

Furthermore, it is surprising that in some embodiments, the cream may further produce a long lasting soothing effect on the skin. The term "soothing", as used herein, means that the formulation is moisturizing, softening, cosmetically appealing, non-irritating or generally calming and comforting to the skin or may decrease any erythema (or redness), if present.

Thus, in some embodiments, the cream formulation is soothing to the skin. In some embodiments, the soothing effect of the cream formulations of embodiments herein may be long-lasting. In some embodiments, the soothing effect may last up to at least about four hours, at least about five hours, at least about six hours, at least about seven hours, at least about eight hours, at least about ten hours, at least about 12 hours, at least about 15 hours, at least about 18 hours, at least about 21 hours, at least about 24 hours or at least about 48 hours with a single application. In some embodiments, the soothing effect may last for from about 1 to about 48 hours; from about 1 to about 24 hours; from about 1 to about 21 hours; from about 1 to about 18 hours; from about 1 to about 16 hours; from about 1 to about 12 hours; from about 1 to about 10 hours; from about 1 to about 8 hours; from about 2 to about 24 hours; from about 2 to about 16 hours; from about 2 to about 12 hours; from about 2 to about 8 hours; from about 4 to about 24 hours; from about 4 to about 16 hours; from about 4 to about 12 hours; from about 4 to about 8 hours; from about 6 to about 24 hours; from about 6 to about 16 hours; from about 6 to about 12 hours; from about 6 to about 8 hours; from about 2 to about 6 hours; from about 4 to about 6 hours, or combinations thereof. In some embodiments, this soothing effect may be maintained with daily application of the cream formulation to the skin. In some embodiments, this soothing effect may be maintained for as long as the cream formulation is applied to the skin daily. In some embodiments, this soothing effect may be maintained with daily application of the cream formulation for at least about 1 month, at least about 2 months, at least about 3 months, at least about 4 months, at least about 5 months, at least about 6 months, at least about 9 months, or at least about 12 months.

In some embodiments described herein, the cream formulation is cosmetically elegant and highly stable. Without wishing to be bound by theory, it is believed that such cosmetically elegant and stable emulsions may restore and reinforce the epidermal barrier function ordinarily provided by healthy stratum corneum, ceramides, cholesterol and epidermal lipids, providing protection and restoring hydration to the skin.

In some embodiments, the cream formulation comprises an emulsifier in an amount of greater than about 5% and is non-irritating. In some embodiments, the cream formulation comprises an emulsifier in an amount of greater than about 10% and is non-irritating. In some embodiments, the cream formulation comprises an emulsifier in an amount of greater than about 15% and is non-irritating. In some embodiments, the cream formulation comprises an emulsifier in an amount of greater than about 20% and is non-irritating. In some embodiments, the cream formulation comprises an emulsifier in an amount of greater than about 25% and is non-irritating. In some embodiments, the cream formulation comprises an emulsifier in an amount of greater than about 30% and is non-irritating. In some embodiments, the cream formulation comprises propylene glycol and is non-irritating. In some embodiments, the cream formulation comprises propylene glycol in an amount of greater than about 4% and is non-irritating.

The creams of various embodiments may include any number of additional components such as, for example, preservatives, emulsion stabilizers, pH adjusters, chelating agents, viscosity modifiers, antioxidants, surfactants, emollients, opacifying agents, skin conditioners, buffers, fragrances and combinations thereof. In some embodiments, such additional components may provide a dual purpose. For example, certain surfactants may also act as emulsifiers, certain emollients may also act as opacifying agents, and certain buffering agents may also act as chelating agents.

In certain embodiments of the invention, the formulation may further comprise a topically active pharmaceutical or cosmetic agent other than oxymetazoline, destined in part, to have a synergistic effect or a therapeutic effect associated with another skin complaint, condition or affliction. Examples of these agents include: anti-rosacea agents such as metronidazole, precipitated sulfur, sodium sulfacetamide, or azelaic acid; antibacterial agents (antibiotics) such as clindamycin phosphate, erythromycin, or antibiotics from the tetracycline family; antimycobacterial agents such as dapsone; other antiacne agents such as retinoids, or benzoyl peroxide; antiparasitic agents such as metronidazole, permethrin, crotamiton, thiabendazole, ivermectin or pyrethroids; antifungal agents such as compounds of the imidazole family such as miconazole, clotrimazole, econazole, ketoconazole, or salts thereof, polyene compounds such as amphotericin B, compounds of the allylamine family such as terbinafine; steroidal anti-inflammatory agents such as hydrocortisone triamcinolone, fluocinonide, betamethasone valerate or clobetasol propionate, or non-steroidal anti-inflammatory agents such as ibuprofen and salts thereof, naproxen and salts thereof, or acetaminophen; anesthetic agents such as the "amide" and "ester" anesthetics, including, but not limited to, lidocaine, prilocaine, tetracaine, hydrochloride and derivatives thereof; antipruriginous agents such as thenaldine, trimeprazine, or pramoxine; antiviral agents such as acyclovir; keratolytic agents such as alpha- and beta-hydroxy acids such as glycolic acid or salicylic acid, or urea; anti-free radical agents (antioxidants) such as Vitamin E (alpha tocopherol) and its derivatives, Vitamin C (ascorbic acid), Vitamin A (retinol) and its derivatives, and superoxide dismutases; antiseborrheic agents such as zinc pyrithione and selenium sulfide; antihistamines such as cyproheptadine or hydroxyzine; tricyclic antidepressants such as doxepin hydrochloride; antipsoriatic agents such as calcipotriene, anthralines, coal tar; immune modulating agents such as imiquimod, or the calcineurin inhibitors pimecrolimus and tacrolimus, and chemotherapeutic agents such as 5-fluorouracil, nitrogen mustard, carmustine, bexarotene, mitomycin-c or combinations thereof.

The topically active pharmaceutical or cosmetic agent may include, without limitation, one or more of hydroxyacids, polyhydroxy acids, polyhydroxy lactones, ketoacids and related compounds; phenyl alpha acyloxyalkanoic acids and derivatives; N-acyl-aldosamines, N-acylamino acids and related N-acyl compounds; N-(phosphonoalkyl)-aminocarbohydrates, N-(phosphonoalkyl)-amino acids and their related N-(phosphonoalkyl)-compounds; local analgesics and anesthetics; anti-acne agents; anti-bacterial agents; anti-yeast agents; anti-fungal agents; anti-viral agents; anti-infective agents; anti-dandruff agents; anti-dermatitis agents; anti-eczema agents; anti-histamine agents; anti-pruritic agents; anti-emetics; anti-motion sickness agents; anti-inflammatory agents; anti-hyperkeratotic agents; antiperspirants; anti-psoriatic agents; anti-rosacea agents; anti-seborrheic agents; hair conditioners and hair treatment agents; anti-aging and anti-wrinkle agents; anti-anxiety agents; anti-convulsant agents; anti-depressant agents; sunblock and sunscreen agents; skin lightening agents; depigmenting agents; astringents; cleansing agents; corn, callus and wart removing agents; skin plumping agents; skin volumizing agents; skin firming agents; matrix metalloproteinase (MMP) inhibitors; topical cardiovascular agents; wound-healing agents; gum disease or oral care agents; amino acids; peptides; dipeptides; tripeptides; glutathione and its derivatives; oligopeptides; polypeptides; carbohydrates; aminocarbohydrates; vitamins; corticosteroids; tanning agents; hormones, retinoids or combinations thereof.

In some embodiments, the topically active pharmaceutical or cosmetic agent may include, without limitation, abacavir, acebutolol, acetaminophen, acetaminosalol, acetazolamide, acetohydroxamic acid, acetylsalicylic acid, N-acylglutathione ethyl ester and other esters, N-acyl proline ethyl ester and other esters, acitretin, aclovate, acrivastine, actiq, acyclovir, adalimumab, adapalene, adefovir dipivoxil, adenosine, albuterol, alefacept, alfuzosin, allopurinol, alloxanthine, almotriptan, alprazolam, alprenolol, aluminum acetate, aluminum chloride, aluminum chlorohydroxide, aluminum hydroxide, amantadine, amiloride, aminacrine, p-aminobenzoic acid, aminocaproic acid, aminolevulinic acid, aminosalicylic acid, amiodarone, amitriptyline, amlodipine, amocarzine, amodiaquin, amorolfine, amoxapine, amphetamine, ampicillin, anagrelide, anastrozole, anthralin, apomorphine, aprepitant, arbutin, aripiprazole, ascorbic acid, ascorbyl palmitate, atazanavir, atenolol, atomoxetine, atropine, azathioprine, azelaic acid, azelastine, azithromycin, bacitracin, beclomethasone dipropionate, bemegride, benazepril, benzilic acid, bendroflumethiazide, benzocaine, benzonatate, benzophenone, benzoyl peroxide, benztropine, bepridil, betamethasone dipropionate, betamethasone valerate, botulinum toxin, brimonidine, brompheniramine, bupivacaine, buprenorphine, bupropion, burimamide, butenafine, butoconazole, cabergoline, caffeic acid, caffeine, calcipotriene, camphor, candesartan cilexetil, capsaicin, carbamazepine, carbamide peroxide, cefditoren pivoxil, cefepime, cefpodoxime proxetil, celecoxib, cetirizine, cevimeline, chitosan, chlordiazepoxide, chlorhexidine, chloroquine, chlorothiazide, chloroxylenol, chlorpheniramine, chlorpromazine, chlorpropamide, ciclopirox, cilostazol, cimetidine, cinacalcet, ciprofloxacin, citalopram, citric acid, cladribine, clarithromycin, clemastine, clindamycin, clioquinol, clobetasol propionate, clocortolone pivalate, clomiphene, clonidine, clopidogrel, clotrimazole, clozapine, cocaine, codeine, cromolyn, crotamiton, cyclizine, cyclobenzaprine, cycloserine, cytarabine, dacarbazine, dalfopristin, dapsone, daptomycin, daunorubicin, deferoxamine, dehydroepiandrosterone, delavirdine, desipramine, desloratadine, desmopressin, desoximetasone, dexamethasone, dexmedetomidine, dexmethylphenidate, dexrazoxane, dextroamphetamine, diazepam, diclofenac, dicyclomine, didanosine, dihydrocodeine, dihydromorphine, diltiazem, 6,8-dimercaptooctanoic acid (dihydrolipoic acid), diphenhydramine, diphenoxylate, dipyridamole, disopyramide, dobutamine, dofetilide, dolasetron, donepezil, dopa esters, dopamide, dopamine, dorzolamide, doxepin, doxorubicin, doxycycline, doxylamine, doxypin, duloxetine, dyclonine, econazole, efalizumab, eflornithine, eletriptan, emtricitabine, enalapril, ephedrine, epinephrine, epinine, epirubicin, eptifibatide, ergotamine, erythromycin, escitalopram, esmolol, esomeprazole, estazolam, estradiol, etanercept, ethacrynic acid, ethinyl estradiol, ethyl pyruvate, etidocaine, etomidate, famciclovir, famotidine, felodipine, fentanyl, ferulic acid, fexofenadine, finasteride, flecamide, fluconazole, flucytosine, fluocinolone acetonide, fluocinonide, 5-fluorouracil, fluoxetine, fluphenazine, flurazepam, fluticasone propionate, fluvoxamine, formoterol, furosemide, galactarolactone, galactonic acid, galactonolactone, galantamine, gatifloxacin, gefitinib, gemcitabine, gemifloxacin, glucarolactone, gluconic acid, gluconolactone, glucuronic acid, glucuronolactone, glycolic acid, griseofulvin, guaifenesin, guanethidine, N-guanylhistamine, haloperidol, haloprogin, hexylresorcinol, homatropine, homosalate, hydralazine, hydrochlorothiazide, hydrocortisone, hydrocortisone 21-acetate, hydrocortisone 17-butyrate, hydrocortisone 17-valerate, hydrogen peroxide, hydromorphone, hydroquinone, hydroquinone monoether, hydroxyzine, hyoscyamine, hypoxanthine, ibuprofen, ichthammol, idarubicin, imatinib, imipramine, imiquimod, indinavir, indomethacin, infliximab, irbesartan, irinotecan, isoetharine, isoproterenol, itraconazole, kanamycin, ketamine, ketanserin, ketoconazole, ketoprofen, ketotifen, kojic acid, labetalol, lactic acid, lactobionic acid, lamivudine, lamotrigine, lansoprazole, letrozole, leuprolide, levalbuterol, levofloxacin, lidocaine, linezolid, lobeline, loratadine, loperamide, losartan, loxapine, lysergic diethylamide, mafenide, malic acid, maltobionic acid, mandelic acid, maprotiline, mebendazole, mecamylamine, meclizine, meclocycline, memantine, menthol, meperidine, mepivacaine, mequinol, mercaptopurine, mescaline, metanephrine, metaproterenol, metaraminol, metformin, methadone, methamphetamine, methotrexate, methoxamine, methyldopa esters, methyldopamide, 3,4-methylenedioxymethamphetamine, methyllactic acid, methyl nicotinate, methylphenidate, methyl salicylate, metiamide, metolazone, metoprolol, metronidazole, mexiletine, miconazole, midazolam, midodrine, miglustat, minocycline, minoxidil, mirtazapine, mitoxantrone, moexiprilat, molindone, monobenzone, morphine, moxifloxacin, moxonidine, mupirocin, nadolol, naftifine, nalbuphine, nalmefene, naloxone, naproxen, nefazodone, nelfinavir, neomycin, nevirapine, nicardipine, nicotine, nifedipine, nimodipine, nisoldipine, nitrofurantoin, nizatidine, norepinephrine, nystatin, octopamine, octreotide, octyl methoxycinnamate, octyl salicylate, ofloxacin, olanzapine, olmesartan medoxomil, olopatadine, omeprazole, ondansetron, oxiconazole, oxotremorine, oxybenzone, oxybutynin, oxycodone, oxymetazoline, padimate O, palonosetron, pantothenic acid, pantoyl lactone, paroxetine, pemoline, penciclovir, penicillamine, penicillins, pentazocine, pentobarbital, pentostatin, pentoxifylline, pergolide, perindopril, permethrin, phencyclidine, phenelzine, pheniramine, phenmetrazine, phenobarbital, phenol, phenoxybenzamine, phentolamine, phenylephrine, phenylpropanolamine, phenyloin, N-(phosphonomethyl)-glycine, N-(phosphonomethyl)-creatine, N-(phosphonomethyl)-tyramine, physostigmine, pilocarpine, pimecrolimus, pimozide, pindolol, pioglitazone, pipamazine, piperonyl butoxide, pirenzepine, podofilox, podophyllin, povidone iodine, pramipexole, pramoxine, prazosin, prednisone, prenalterol, prilocalne, procainamide, procaine, procarbazine, praline, promazine, promethazine, promethazine propionate, propafenone, propoxyphene, propranolol, propylthiouracil, protriptyline, pseudoephedrine, pyrethrin, pyrilamine, pyrimethamine, quetiapine, quinapril, quinethazone, quinidine, quinupristin, rabeprazole, reserpine, resorcinol, retinal, 13-cis retinoic acid, retinoic acid, retinol, retinyl acetate, retinyl palmitate, ribavirin, ribonic acid, ribonolactone, rifampin, rifapentine, rifaximin, riluzole, rimantadine, risedronic acid, risperidone, ritodrine, rivastigmine, rizatriptan, ropinirole, ropivacaine, salicylamide, salicylic acid, salmeterol, scopolamine, selegiline, selenium sulfide, serotonin, sertaconazole, sertindole, sertraline, shale tar, sibutramine, sildenafil, sotalol, streptomycin, strychnine, sulconazole, sulfacetamide, sulfabenz, sulfabenzamide, sulfabromomethazine, sulfacetamide (sodium sulfacetamide), sulfachlorpyridazine, sulfacytine, sulfadiazine, sulfadimethoxine, sulfadoxine, sulfaguanole, sulfalene, sulfamethizole, sulfamethoxazole, sulfanilamide, sulfapyrazine, sulfapyridine, sulfasalazine, sulfasomizole, sulfathiazole, sulfisoxazole, sulfur, tacrolimus, tadalafil, tamsulosin, tartaric acid, tazarotene, tegaserol, telithromycin, telmisartan, temozolomide, tenofovir disoproxil, terazosin, terbinafine, terbutaline, terconazole, terfenadine, tetracaine, tetracycline, tetrahydrozoline, thalidomide, theobromine, theophylline, thiabendazole, thioctic acid (lipoic acid), thioridazine, thiothixene, thymol, tiagabine, timolol, tinidazole, tioconazole, tirofiban, tizanidine, tobramycin, tocamide, tolazoline, tolbutamide, tolnaftate, tolterodine, tramadol, tranylcypromine, trazodone, triamcinolone acetonide, triamcinolone diacetate, triamcinolone hexacetonide, triamterene, triazolam, triclosan, triflupromazine, trimethoprim, trimipramine, tripelennamine, triprolidine, tromethamine, tropic acid, tyramine, undecylenic acid, urea, urocanic acid, ursodiol, vardenafil, venlafaxine, verapamil, vitamin E acetate, voriconazole, warfarin, wood tar, xanthine, zafirlukast, zaleplon, zinc pyrithione, ziprasidone, zolmitriptan, zolpidem or combinations thereof.

Embodiments are not limited by the number or type of preservatives used in the creams described herein. For example, preservatives useful in embodiments may include, but are not limited to, pentylene glycol, ethylene diamine tetra acetate (EDTA) and its salts, chlorhexidine and its diacetate, dihydrochloride, digluconate derivatives, 1,1,1-trichloro-2-methyl-2-propanol, parachlorometaxylenol, polyhexamethylenebiguanide hydrochloride, dehydroacetic acid, diazolidinyl urea, 2,4-dichlorobenzyl alcohol, 4,4-dimethyl-1,3-oxazolidine, formaldehyde, glutaraldehyde, dimethylidantoin, imidazolidinyl urea, 5-chloro-2-methyl-4-isothiazolin-3-one, ortho-phenylphenol, benzyl alcohol, benzoic acid and its salts, 4-hydroxybenzoic acid and its methyl-, ethyl-, propyl-, isopropyl-, butyl-, isobutyl-esters(parabens), methylparaben, propylparaben, isopropylparabens, isobutylparabens, butylparabens, ethylparaben, trichlosan, 2-phenoxyethanol, phenyl mercuric acetate, quaternium-15, methylsalicylate, salicylic acid and its salts, sorbic acid and its salts, iodopropanyl butylcarbamate, calcium sorbate, zinc pyrithione, 5-bromo-Snitro-1,3-dioxane, 2-bromo-2-nitropropane-1,3-diol, sulfites, bisulfites, and benzalkonium chloride, phenoxyethanol, 2-phenoxyethanol, chloroxylenol, diazolidinyl urea, and combinations thereof. In embodiments, the cream may include any preservative, including, but not limited to. those listed above or a combination thereof. In certain embodiments, the cream may include a combination of methylparaben, propylparaben, and 2-phenoxyethanol.

Preservatives may be provided in any concentration known in the art. For example in some embodiments, the cream may include from about 0.01% to about 3% by weight of any one preservative, and in other embodiments, the cream may include from about 0.05% to about 1.2% by weight of any one preservative. Thus, in creams that include more than one preservative each preservative may be provided at about 0.01% to about 3% by weight or from about 0.05% to about 1.2% by weight. In some embodiments the cream may comprise each preservative in an amount of about 0.05%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, or about 1% by weight.

The creams of various embodiments may include any chelating agent or combination of chelating agents. Examples of the chelating agents useful in various embodiments include, but are not limited to, alanine, sodium polyphosphate, sodium methaphosphate, citric acid, phosphoric acid, tartaric acid, ethylenediamine tetra acetic acid (Edetate, EDTA) and derivatives and salts thereof, dihydroxyethyl glycine, and mixtures thereof. In particular embodiments, the chelating agent may be EDTA or edetate disodium, dihydrate.

The chelating agents may be provided in any effective amount. For example, in some embodiments, the cream may include from about 0.001% to about 2% by weight chelating agent, and in other embodiments, the cream may include from about 0.05% to about 1% by weight chelating agent. In some embodiments the cream may comprise about 0.001%, about 0.002%, about 0.003%, about 0.004%, about 0.005%, about 0.006%, about 0.007%, about 0.008%, about 0.009%, about 0.01%, about 0.011%, about 0.012%, about 0.013%, about 0.014%, about 0.015%, about 0.016%, about 0.017%, about 0.018%, about 0.019%, about 0.02%, about 0.025%, about 0.03%, about 0.035%, about 0.04%, about 0.045%, or about 0.05% by weight chelating agent.

In some embodiments, the cream may include one or more viscosity modifiers. The viscosity modifier of such embodiments may generally include a high molecular weight compound such as, for example, carboxyvinyl polymer, carboxymethyl cellulose, polyvinyl pyrrolidone, hydroxyethyl cellulose, methyl cellulose, natural gum such as gelatin and tragacanth gum, and various alcohols such as polyvinyl alcohol. In other embodiments, the viscosity modifier may include ethanol or isopropyl alcohol. In some embodiments, the viscosity modifier may be a high molecular weight saturated and unsaturated fatty alcohol such as, but are not limited to, carbitol, lauryl alcohol, myristyl alcohol, cetyl alcohol, isocetyl alcohol, stearyl alcohol, isostearyl alcohol, hydroxystearyl alcohol, oleyl alcohol, ricinoleyl alcohol, behenyl alcohol, erucyl alcohol, 2-octyldodecanyl alcohol, cetearyl alcohol, lanolin alcohol, and the like, and in certain embodiments, the viscosity modifier may be oleyl alcohol.

The viscosity modifier may be provided in any amount necessary to create a cream that fits within the viscosity described above, and in certain embodiments, the cream may include from about 0.1% to about 30% by weight viscosity modifier. In some embodiments, the cream may include from about 0.5% to about 20% by weight viscosity modifier. In some embodiments, the cream may include from about 0.5% to about 10% by weight viscosity modifier. In some embodiments, the cream may include a viscosity modifier in an amount from about 2% to about 10% by weight. In some embodiments the cream may comprise about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, or about 10% by weight viscosity modifier.

The cream of certain embodiments may include one or more antioxidants. Numerous antioxidants are known in the art, and any such antioxidant may be used to prepare the oxymetazoline creams described herein. Examples of suitable antioxidants include, but are not limited to, amino acids such as glycine, histidine, tyrosine, trytophan and derivatives thereof, imidazoles such as urocanic acid and derivatives thereof, peptides, such as D,L-carnosine, D-carnosine, L-carnosine and derivatives thereof such as anserine, carotinoids, carotenes such as α-carotone, β-carotene, lycopene, and derivatives thereof, chlorogenic acid and derivatives thereof, lipoic acid and derivatives thereof such as dihydrlipoic acid, aurothioglycose, propylthiouracil and other thiols such as thioredoxin, glutathione, cysteine, cystine, cystamine and glycosyl, N-acetyl, methyl, ethyl, propyl, amyl, butyl, lauryl, palmitoyl, oleyl, α-linoleyl, cholesteryl and glyceryl esters and salts thereof, dilauryl thiodipropionate, distearyl thiodipropionate, thiodipropionic acid and derivatives thereof such as esters, ethers, peptides, lipids, nucleotides, nucleosides, and salts, sulfoximine compounds such as buthionine sulfoximines, homocysteine sulfoximine, buthionine sulfones, penta-, hexa-, hepta-thionine sulfoximine, unsaturated fatty acids and derivatives thereof such as α-linolenic acid, linoleic acid, oleic acid, folic acid and derivatives thereof, ubiquinone and ubiquinol and derivatives thereof, vitamin C and derivatives there of such as ascorbyl palmitate, magnesium ascorbyl phosphate, ascorbyl acetate, tocopherals and derivatives such as vitamin E acetate, vitamin A and derivatives such as vitamin A palmitate, vitamin B and derivatives thereof, coniferyl benzoate of benzoin resin, rutinic acid and derivatives thereof, α-glycosylrutin, ferulic acid, furfurylidene glucitol, carnosine, butyl hydroxytoluene, trihydroxy-butyrophenone, uric acid and derivatives thereof, mannose and derivatives thereof, superoxide dismutase, zinc and derivatives thereof such as ZnO, $ZnSO_4$, selenium and derivatives thereof such as selenium methionine, stilbene and derivatives thereof such as stilbene oxide, trans-stilbene oxide and the like. In particular exemplary embodiments, the one or more antioxidants may include vitamin B, nordihydroguaiaretic acid, butylated hydroxyanisole (BHA), butylated hydroxytoluene (BHT), propyl gallate, erythorbate acid, sodium erythorbate, ascorbir palmitate, and ascorbir stearate. butyl hydroxyanisole, and gallic esters, and in some embodiments, the one or more antioxidants may include BHT.

The one or more antioxidants may be provided in any suitable amount. For example in some embodiments, one or more antioxidants may be from about 0.001% to about 3% by weight of the cream, and in other embodiments, the one or more antioxidants may be from about 0.01% to about 1% by weight of the cream or from about 0.01% to about 0.50% by weight of the cream. In some embodiments the cream may comprise about 0.01%, about 0.015%, about 0.02%, about 0.025%, about 0.03%, about 0.035%, about 0.04%, about 0.045%, about 0.05%, about 0.055%, about 0.06%, about 0.065%, about 0.07%, about 0.075%, about 0.08%, about 0.085%, about 0.09%, about 0.095%, or about 0.1% by weight antioxidant.

In some embodiments, oxymetazoline creams described herein may include one or more surfactants. Such embodiments are not limited by type of surfactant used; for example, in some embodiments, the one or more surfactants may be anionic surfactants such as alkyl sulfates, alkylether sulfates, alkylsulfonates, alkylaryl sulfonates, alkyl succinates, alkyl sulfosuccinates, N-alkoylsarcosinates, acyl taurates, acyl isethionates, alkyl phosphates, alkyl ether phosphates, alkyl ether carboxylates, α-olefinsulfonates, and the alkali metal and alkaline earth metal salts and ammonium and triethanolamine salts thereof. Such alkyl ether sulfates, alkyl ether phosphates and alkyl ether carboxylates can have between 1 and 10 ethylene oxide or propylene oxide units, and in some embodiments, 1 to 3 ethylene oxide units, per molecule. More specific examples include, but are not limited to, sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecylbenzene sulfonate, triethanolamine dodecylbenzenesulfonate. In other embodiments, the one or more surfactants may be amphoteric surfactants such as, for example, alkylbetaines, alkylamidopropylbetaines, alkylsulfobetaines, alkylglycinates, alkylcarboxyglycinates, alkylamphoacetates or α-propionates, alkylamphodiacetates or α-dipropionates, and more specifically, cocodimethylsulfopropylbetaine, lauryl betaine, cocamidopropylbetaine or sodium cocamphopropionate.

In certain embodiments, the one or more surfactants may be non-ionic surfactants such as, for example, the reaction products of aliphatic alcohols or alkylphenols having 6 to 20 carbon atoms in a linear or branched alkyl chain with ethylene oxide and/or propylene oxide where the alkylene oxide may be from about 6 moles to about 60 moles per mole of alcohol. In particular embodiments, non-ionic surfactants may include alkylamine oxides, mono- and dialkylalkanolamides, fatty acid esters of polyethylenenglycols, ethoxylated fatty acids amides, saturated fatty acid alcohols reacted with ethylene oxide, alkyl polyglycosides, and sorbitan ether esters, and in some embodiments, the non-ionic surfactant may be ceteareth-2, ceteareth-3, ceteareth-4, ceteareth-5, ceteareth-6, ceteareth-7, ceteareth-8, ceteareth-9, ceteareth-10, ceteareth-11, ceteareth-12, ceteareth-13, ceteareth-14, ceteareth-15, ceteareth-16, ceteareth-17, ceteareth-18, ceteareth-20, ceteareth-22, ceteareth-23, ceteareth-24, ceteareth-25, ceteareth-27, ceteareth-28, ceteareth-29, ceteareth-30, ceteareth-33, ceteareth-34, ceteareth-40, ceteareth-50, ceteareth-55, ceteareth-60, ceteareth-80, ceteareth-100, and the like or combinations thereof, or one or more ceteareth in combination with a fatty acid alcohol such as stearyl alcohol, oleyl alcohol, linoleyl alcohol, arachidyl alcohol, cetyl alcohol, and the like. In certain embodiments, the one or more surfactants may be a commercially available ceteareth containing surfactants such as CREMOPHOR EL®, CREMOPHOR A-6®, CREMPHOR A-25® or combinations thereof.

The one or more surfactants of various embodiments may make up from about 0.1% to about 50% by weight of the cream and in some embodiments, from about 0.5% to about 20% by weight of the cream. In embodiments in which more than one surfactant is provided in the oxymetazoline cream, each surfactant may be from about 0.5% to about 12% by weight of the cream, and in some embodiments, each surfactant of the oxymetazoline cream containing two or more surfactants may be from about 0.5% to about 5% by weight of the cream. In some embodiments the cream may comprise each surfactant in an amount of about 0.5%, about 1%, about 1.5%, about 2%, about 2.5%, about 3%, about 3.5%, about 4%, about 4.5%, or about 5% by weight.

In some embodiments, the oxymetazoline cream may include one or more emollients. Generally, emollients function enable the cream and by extension the active agent to remain on the skin surface or in the stratum corneum. Emollients are well known in the art and are listed, for example, the International Cosmetic Ingredient Dictionary, Eighth Edition, 2000, which is hereby incorporated by reference in its entirety. In certain embodiments, the one or more emollient may be fatty esters, fatty alcohols, or combinations thereof including, but not limited to, diisopropyl adipate, oleyl alcohol, lanolin, isopropyl myristate, isopropyl palmitate, caprylic/capric triglycerides, cetyl lactate, cetyl palmitate, hydrogenated castor oil, glyceryl esters, hydroxycetyl isostearate, hydroxy cetyl phosphate, isopropyl isostearate, isostearyl isostearate, diisopropyl sebacate, polyoxypropylene (5) poloxyethylene (20) cetyl ether (PPG-5-Ceteth-20), 2-ethylhexyl isononoate, 2-ethylhexyl stearate, $C_{12}$ to $C_{16}$ fatty alcohol, $C_{12}$ to $C_{16}$ fatty alcohol lactate, isopropyl lanolate, 2-ethyl-hexyl salicylate, and mixtures thereof. In some embodiments, the one or more emollients may be a combination of fatty alcohols. In certain embodiments, the one or more emollients may be 1-hexadecanol, acetylated lanolin, behenocyl dimethicone, $C_{12-15}$ alkyl benzoate, cetearyl octanoate, cocoglycerides, dicaprylate/dicaprate dimethicone copolyol, dimethiconol, dioctyl adipate, glyceryl stearate, isocetyl alcohol, isohexadecane, isopentylcyclohexanone, isopropyl palmitate, lauryl lactate, mineral oil, methoxy peg-22/dodecyl glycol copolymer, myristyl lactate, ocryldodecyl neopentanoate, octyl cocoate, octyl palmitate, octyl stearate, octyldodecyl neopentanoate, polyglyceryl-4 isosterate, polyoxyl 40 stearate, polyoxymethylene urea, potassium sorbate, propylene glycol, propylene glycol isoceth-3 acetate, and propylene glycol myristyl ether acetate.

The emollient may be provided in any suitable amount. For example, in some embodiments, the one or more emollient may be from about 1% to about 50% by weight of the cream, and in other embodiments, the emollient may be from about 2% to about 7% by weight of the oxymetazoline cream. In some embodiments the cream may comprise each emollient in an amount of about 1%, about 1.5%, about 2%, about 2.5%, about 3%, about 3.5%, about 4%, about 4.5%, about 5%, about 5.5%, about 6%, about 6.5%, about 7%, about 7.5%, or about 8% by weight. As indicated above, the emollient may also be provided in an amount sufficient to provide a ratio of emulsifier to emollient of from about 0.002:1 to about 50:1. In some embodiments, the ratio of emulsifier to emollient is from about 0.1:1 to about 1.8:1, from about 0.2:1 to about 1.8:1, from about 0.3:1 to about 1.8:1, from about 0.4:1 to about 1.8:1, from about 0.5:1 to about 1.8:1, from about 0.7:1 to about 1.8:1, about 0.3:1 to about 1.5:1, about 0.3:1 to about 1.285:1, about 0.3 to about 1:1, about 0.4:1 to about 1.5:1, about 0.4:1 to about 1.285:1, about 0.4:1 to about 1:1, about 0.7:1 to about 1.8:1, about 0.7:1 to about 1.5:1, about 0.7:1 to about 1.285:1, about 0.7:1 to about 1:1, about 0.73:1 to about 1.8:1, about 0.73:1 to about 1.5:1, about 0.73:1 to about 1.285:1, about 0.73:1 to about 1:1, about 0.87:1 to about 1.5:1, about 0.87:1 to about 1.285:1, about 0.87:1 to about 1:1, about 1:1 to about 1.285:1, about 1:1 to about 1.25:1, about 1:1 to about 1.2:1, about 1:1, about 0.87:1, about 0.73:1, or about 0.7:1, or combinations thereof. In such embodiments, the percentage by weight of emollient in the cream will fall within these ranges. In some embodiments, the emulsifier may comprise TEFOSE™ 63, cetostearyl alcohol macrogol (6) cetostearyl ether, macrogol(25) cetostearyl ether or combinations thereof. In some embodiments, the cream may comprise an emulsifier of low molecular weight polyethylene glycol(s) or its esters (e.g. PEG-32 stearate, PEG-6 stearate). In some embodiments, the ratio of TEFOSE™ 63 to cetostearyl alcohol is from about 0.7:1 to about 1.8:1, about 0.7:1 to about 1.5:1, about 0.7:1 to about 1.285:1, about 0.7 to about 1:1, about 0.73:1 to about 1.8:1, about 0.73:1 to about 1.5:1, about 0.73:1 to about 1.285:1, about 0.73:1 to about 1:1, about 0.87:1 to about 1.5:1, about 0.87:1 to about 1.285:1, about 0.87:1 to about 1:1, about 1:1 to about 1.285:1, about 1:1 to about 1.25:1, about 1:1 to about 1.2:1, about 1:1 to about 0.87:1, about 0.73:1, or about 0.7:1 or combinations thereof. In some embodiments, the emollient may comprise triglycerides medium chain, diisopropyl adipate, oleyl alcohol, lanolin or combinations thereof.

Without wishing to be bound by theory, from the standpoint of emulsion stability, if an ester is not properly emulsified, the emulsion will exhibit "creaming": separation of the non-polar phase to the top of the cream and aqueous layer underneath. It is believed that the embodiments described herein contain no "true" oil phase and the medium chain triglycerides, diisopropyl adipate and oleyl alcohol are not "true" oils, thus forming an oil-phase-less emulsion. This may make the cream formulation of embodiments herein extremely difficult to emulsify and it may explain why there are so many varied emulsifiers.

In certain embodiments, the oxymetazoline cream may include one or more opacifying agents. Opacifying agents provide color or whiteness to a composition that may otherwise be clear of would have an undesirable color. In some embodiments, components such as, for example, emollients, surfactants, and/or emulsifiers may provide sufficient opaqueness. In other embodiments, one or more additional opacifying agents may be provided to the cream. Opacifying agents are well known in the art and include, but are not limited to, higher fatty alcohols such as cetyl, stearyl, cetostearyl alcohol, arachidyl and behenyl alcohols, solid esters such as cetyl palmitate, glyceryl laurate, stearamide MEA-stearate, high molecular weight fatty amides and alkanolamides and various fatty acid derivatives such as propylene glycol and polyethylene glycol esters. In other embodiments, opacifying agents may include inorganic materials such as, for example, magnesium aluminum silicate, zinc oxide, titanium dioxide or other sunblocking agents.

In embodiments in which an opacifying agent is used, the opacifying agent may be provided in any amount necessary to provide the desired opaqueness. In such embodiments, the opacifying agent may generally be from about 0.01% to about 20% by weight of the cream, and in some embodiments, the opacifying agent may be from about 0.01% to about 5% or about 0.02% to about 2% by weight of the cream. In some embodiments the cream may comprise about 2%, about 2.5%, about 3%, about 3.5%, about 4%, about 4.5%, about 5%, about 5.5%, about 6%, about 6.5%, about 7%, about 7.1%, about 7.2%, about 7.3%, about 7.4%, about 7.5%, about 7.6%, about 7.7%, about 7.8%, about 7.9%, about 8%, about 8.1%, about 8.2%, about 8.3%, about 8.4%, about 8.5%, about 8.6%, about 8.7%, about 8.8%, about 8.9%, about 9%, about 9.5%, about 10%, about 10.5%, about 11%, about 11.5%, or about 12% by weight opacifying agent.

In some embodiments, the oxymetazoline cream may include one or more skin conditioners. Skin conditioners are components that may generally improve moisture retention in the skin, retard evaporation of water from the skin, and cause plasticization/softening of the skin. Common skin conditioners include, for example, mineral oil, petrolatum, aliphatic alcohols, lanolin and its derivatives, fatty acids, glycol fatty acids, sugars, glycerin, propylene glycol, sorbitols, and polyethylene glycols, vitamins and herbal derivatives. Additional skin conditioners can be found in CTFA Cosmetic Ingredient Handbook, 1st Ed., 1988, which is hereby incorporated herein by reference in its entirety. In some embodiments, the one or more skin conditioners may include, but are not limited to, humectants, such as fructose, glucose, glycerin, propylene glycol, glycereth-26, mannitol and urea, pyrrolidone carboxylic acid, hydrolyzed lecithin, coco-betaine, cysteine hydrochloride, glutamine, polyoxypropylene (15) polyoxyethylene (PPG-15), sodium gluconate, potassium aspartate, oleyl betaine, thiamine hydrochloride, sodium laureth sulfate, sodium hyaluronate, hydrolyzed proteins, hydrolyzed keratin, amino acids, amine oxides, water-soluble derivatives of vitamins A, E and D, amino-functional silicones, ethoxylated glycerin, α-hydroxy acids and salts thereof, water-soluble fatty oil derivatives, such as PEG-24 hydrogenated lanolin, almond oil, grape seed oil and castor oil; numerous other water-soluble skin conditioners listed, and mixtures thereof. In certain embodiments, the skin conditioners may include lanolin or lanolin derivatives, caprylic capric/triglyceride, diisopropyl adipate, and combinations thereof.

Skin conditioners may be provided to the creams of various embodiments in any amount known in the art, and the amount of skin conditioner provided may vary depending upon the type of skin condition or combination of skin conditioners used. In general, the creams of embodiments may include a conditioner in an amount from about 1% to about 50% by weight of the cream or from about 1% to about 25% by weight of the cream. In some embodiments the cream may comprise each skin conditioner in an amount of about 1%, about 1.5%, about 1.6%, about 1.7%, about 1.8%, about 1.9%, about 2%, about 2.1%, about 2.2%, about 2.3%, about 2.4%, about 2.5%, about 3%, about 3.5%, about 3.6%, about 3.7%, about 3.8%, about 3.9%, about 4%, about 4.1%, about 4.2%, about 4.3%, about 4.4%, about 4.5%, about 5%, about 5.5%, about 6%, about 6.5%, about 6.6%, about 6.7%, about 6.8%, about 6.9%, about 7%, about 7.1%, about 7.2%, about 7.3%, about 7.4%, about 7.5%, about 8%, about 8.5%, about 9%, about 9.5%, or about 10% by weight.

The oxymetazoline creams of various embodiments may be of neutral to mildly acidic pH to allow for comfortable application to the subject's skin, particularly in light of the disease state or condition suffered by the subject. For example, in various embodiments, the pH of the creams may be from about 2.5 to about 7.0, from about 4.0 to about 7.0, or from about 4.0 to about 5.5 at room temperature. In other embodiments, the pH of such creams may be about 4.5 to about 5.5 at room temperature, and in particular embodiments, the pH of the creams may be about 4.5 at room temperature. Any components or combination of components known and useful in the art may be used to achieve an appropriate pH such as, for example, pH regulators including, but not limited to, lactic acid, citric acid, sodium citrate, glycolic acid, succinic acid, phosphoric acid, monosodium phosphate, disodium phosphate, oxalic acid, dl-malic acid, calcium carbonate, sodium hydroxide and sodium carbonate, sodium hydrogen carbonate, and ammonium hydrogen carbonate. In certain embodiments the pH regulators comprise anhydrous citric acid and sodium citrate dihydrate In various embodiments, the total buffer capacity may be from about from about 0 mM to about 600 mM; from about 0 mM to about 600 mM; from about 5 mM to about 600 mM; from about 5 mM to about 400 mM; from about 5 mM to about 300 mM; from about 5 mM to about 200 mM; from about 200 mM to about 400 mM; about 0 mM, about 100 mM, about 200 mM, about 300 mM, about 400 mM, about 500 mM, or about 600 mM. In some embodiments the cream comprises each pH regulator in an amount of about 0.05%, about 0.1%, about 0.15%, about 0.16%, about 0.17%, about 0.18%, about 0.19%, about 0.2%, about 0.21%, about 0.22%, about 0.23%, about 0.24%, about 0.25%, about 0.26%, about 0.27%, about 0.28%, about 0.29%, about 0.3%, about 0.31%, about 0.32%, about 0.33%, about 0.34%, about 0.35%, about 0.36%, about 0.37%, about 0.38%, about 0.39%, about 0.4%, about 0.45%, about 0.5%, about 0.55%, about 0.6%, about 0.65%, about 0.7%, about 0.75%, about 0.8%, about 0.85%, about 0.9%, about 0.95%, or about 1% by weight.

Embodiments of the invention also include methods for preparing pharmaceutical compositions as described above by, for example, conventional mixing and the like. For example, in some embodiments, oxymetazoline may be combined with any combination of components described above in purified water using conventional mixing, and after a stable emulsion has formed, the pH and viscosity may be adjusted using known methods to achieve a cream having an appropriate pH. In other embodiments, various combinations of components may be combined in purified water by conventional mixing and oxymetazoline may then be added to the mixture. The pH, viscosity, opaqueness, and/or density may be adjusted to achieve a cream which is cosmetically acceptable.

Certain embodiments are directed to methods of making the cream formulation comprising making a first solution comprising the steps of dissolving preservatives, such as methylparaben and propylparaben, into a solvent, such as polyethylene glycol 300, mixing with a magnetic stirrer until the mixture becomes homogeneous, adding other preservatives, such as 2-phenoxyethanol, to the mixture; making a second solution comprising the steps of heating purified water, and a chelating agent, such as disodium edetate (EDTA); making an oil phase comprising adding emulsifiers, such as Tefose 63, cetostearyl alcohol, Cremophor A-6 and Cremaphor A-25; antioxidants, such as butylated hydroxytoluene; emollients, such as lanolin, diisopropyl adipate, triglycerides medium chain; and viscosity modifiers, such as cetostearyl alcohol; heating and mixing the oil phase; dissolving oxymetazoline into the second solution to create an aqueous phase; adding the first solution to the aqueous phase to make an aqueous phase solution; and adding the aqueous phase solution to the oil phase to make a cream.

Certain embodiments are directed to methods of making the cream formulation comprising a "one-pot" process. In the one-pot process, the batch may be manufactured in one vessel, kettle or container that can be heated by means of a steam or a heated fluid. First, an oil phase may be made comprising adding emulsifiers, such as Tefose 63, cetostearyl alcohol, Cremophor A-6 and Cremaphor A-25; antioxidants, such as butylated hydroxytoluene; emollients, such as lanolin, diisopropyl adipate, triglycerides medium chain; and viscosity modifiers such as cetostearyl alcohol, heating and mixing the oil phase, then separately in a small container preparing a side-mix by dissolving preservatives, such as methylparaben and propylparaben, into a solvent, such as polyethylene glycol 300, mixing with a magnetic stirrer until the mixture becomes homogeneous, adding other preservatives, such as 2-phenoxyethanol, to the mixture; and a chelating agent, such as disodium edetate (EDTA) and adding this solution to the oil phase, mixing and heating this solution to high temperature and then adding slowly the purified water, the water is added at a rate that the temperature in the pot is maintained at above about 70 degrees C.; once all the water has been added and the cream has been made, dissolving the API (e.g. oxymetazoline) into the cream. Alternatively, the API may be added at any time during the process which is feasible or where it is conventionally added.

Yet other embodiments are directed to methods for using the pharmaceutical compositions. In general, the oxymetazoline creams of certain embodiments described herein may be administered topically to the skin, and in some embodiments, the oxymetazoline creams may be applied to portions of the skin that exhibit or may be prone to papules, pustules, other inflammatory lesions, phymas (skin thickening) or erythema associated with rosacea, purpura, telangiectasias, keratosis pilaris, lupus miliaris disseminatus faciei or the like. In other embodiments, oxymetazoline cream may be applied over an entire skin area including those areas not currently exhibiting or prone to papules, pustules, other inflammatory lesions, phymas (skin thickening) or erythema associated with rosacea, purpura, telangiectasias, keratosis pilaris, lupus miliaris disseminatus faciei or the like. In certain embodiments, the pharmaceutical compositions may be provided in an effective amount to a skin area exhibiting or prone to a skin condition (e.g. dryness).

In various embodiments, the pharmaceutical compositions may be applied to provide an effective amount of oxymetazoline to the subject, and in certain embodiments, the pharmaceutical compositions may be provided in an effective amount to a skin area exhibiting or prone to the symptoms of rosacea, telangiectasias, skin thickening, pustules, papules, other skin erythemas, purpura, keratosis pilaris, lupus miliaris disseminatus faciei or the like. In some embodiments, an effective amount of the cream (e.g. oxymetazoline cream) may be applied to the skin of the subject in need of treatment as the result from a single application. In other embodiments, the cream (e.g. oxymetazoline cream) may be reapplied over the course of, for example, a day, a week, a month, several months, or several years or until the condition is resolved. For example, in one exemplary embodiment, a therapeutic method may include applying the oxymetazoline creams described herein to a skin area exhibiting or prone to symptoms of rosacea, skin thickening, telangiectasias, pustules, papules, other skin erythemas, purpura, keratosis pilaris, lupus miliaris disseminatus faciei or the like once per day as long as the symptoms persist. In other embodiments, the oxymetazoline cream may be applied as a maintenance therapy, wherein the cream is continuously applied as needed or applied on a scheduled basis over time while the subject is in need of such treatment. In embodiments, a therapeutic method may include applying the cream once per day, 2 times per day, 3 times per day, 4 times per day or as needed or prescribed. In some embodiments, a therapeutic method may include applying the cream pro re nata (PRN or as needed). In other embodiments, a therapeutic method may include applying the oxymetazoline cream 2 times per day, for example, every 4 hours, as long as the symptoms persist. In other exemplary embodiments, a therapeutic method may include applying the oxymetazoline creams 2 or more times, for example, every 6 hours or every 12 hours, per day as long as the symptoms persist. In such embodiments, application of the oxymetazoline creams may be carried out until the symptoms of rosacea, skin thickening, telangiectasias, pustules, papules, other skin erythemas, purpura, keratosis pilaris, lupus miliaris disseminatus faciei or the like have been substantially reduced or eliminated, and in some embodiments, the amount of oxymetazoline cream applied or the frequency of application may be modified throughout the course of treatment based on the subject's reaction to the pharmaceutical composition and the clinician's recommendations. For example, after symptom reduction or elimination is observed, the amount of oxymetazoline cream applied or the frequency of applications may be modified to maintain a therapeutic effect.

The creams of various embodiments may be applied by any method. For example, in some embodiments, the oxymetazoline cream may be applied by hand by the subject or another person, such as a clinician. In other embodiments, the cream may be packaged with an applicator such as a wand, swath of cloth, or applicator pad, and in still other embodiments, measured doses of the cream may be packaged for application by hand. Without wishing to be bound by theory, providing the cream with a prepackaged applicator or in measured doses may provide a more controlled dose. In general, the subject and/or clinician will ensure that the cream is applied evenly over the skin area to be treated.

In one embodiment a formulation comprises oxymetazoline and a pharmaceutically acceptable excipient, wherein the formulation is a cream. In one aspect the formulation comprises a therapeutically effective amount of oxymetazoline. In one aspect, the formulation is cosmetically acceptable. In one aspect the formulation comprises an emulsifier and an emollient. In a further aspect the hydrophilic-lipophilic balance of the emulsifier is from about 9.0 to about 17.0. In a further aspect the emulsifier is present in a total amount of from about 1% to about 30% by weight. In a further aspect the emulsifier comprises Tefose 63™. In a further aspect the emulsifier comprises a PEG-stearate, a glycol stearate or a mixture thereof. In a further aspect the emulsifier is polyethylene glycol 6 (PEG-6), polyethylene glycol 32 (PEG-32), and glycol stearate. In a further aspect the emulsifier comprises ethoxylated fatty acids. In a further aspect the emollient is present in a total amount of from about 1% to about 50% by weight. In a further aspect the emollient comprises cetostearyl alcohol. In a further aspect the ratio of the emulsifier to the emollient comprises from about 0.7:1 to about 1.8:1. In a further aspect the ratio of the emulsifier to the emollient comprises from about 0.7:1 to about 1.5:1. In one aspect the formulation comprises an additive selected from the group consisting of preservatives, emulsion stabilizers, pH adjusters, chelating agents, viscosity modifiers, anti-oxidants, surfactants, emollients, opacifying agents, skin conditioners, buffers, and combinations thereof. In a further aspect the one or more preservatives is present in an amount of from about 0.01% to about 5% by weight. In a further aspect the one or more chelating agents is present in an amount of about 0.001% to about 2% by weight. In a further aspect the one or more viscosity modifiers is present in an amount of from about 0.5% to about 30% by weight. In a further aspect the one or more antioxidants is present in an amount of from about 0.01% to about 3% by weight. In a further aspect the one or more surfactants is present in an amount of from about 0.1% to about 50% by weight. In a further aspect the one or more opacifying agents is present in an amount of from about 0.01% to about 20% by weight. In a further aspect the one or more skin conditioners is present in an amount of from about 1% to about 50% by weight. In a further aspect the one or more pH regulators is present in an amount sufficient to provide a pH of from about 2.5 to about 7.0 for the formulation. In one aspect the formulation further comprises a topically active pharmaceutical agent or cosmetic agent. In a further aspect the topically active pharmaceutical agent is selected from the group consisting of an antimycobacterial agent, an anti-rosacea agent, and a mixture thereof. In a further aspect the formulation further comprises dapsone or metronidazole. In one aspect the formulation comprises a pH from about 2.0 to about 7.0 at room temperature. In one aspect the pH of the formulation does not decrease after about 4 weeks storage at about 25° C./60% RH, about 30° C./75% RH or about 40° C./75% RH. In one aspect the pH of the formulation does not decrease after about 1 week storage (e.g. where cream formulation is packaged into tubes—for example into 30 g polyethylene tubes or 30 g glaminate tubes) at about 60° C. In one aspect the pH of the formulation is unchanged after about 4 weeks storage at about 25° C./60% RH, about 30° C./75% RH or about 40° C./75% RH. In one aspect the pH of the formulation is unchanged after about 1 week storage at about 60° C. In one aspect the formulation maintains a pH of from about 4.30 to about 4.70 after about 4 weeks storage at about 25° C./60% RH, about 30° C./75% RH or about 40° C./75% RH. In one aspect the formulation maintains a pH of from about 4.30 to about 4.70 after about 1 week storage at about 60° C. In one aspect the formulation maintains a pH of from about 4.30 to about 4.70 after about 9 months storage at about 25° C./60% RH, or after about 6 months storage at about 40° C./75% RH. In one aspect the formulation maintains a pH of from about 4.10 to about 4.60 after about 3 months storage at about 25° C./60% RH or after about 3 months at about 40° C./75% RH. In one aspect the formulation maintains a pH of about 4.5 after about 4 weeks storage at about 25° C./60% RH, about 30° C./75% RH or about 40° C./75% RH. In one aspect the formulation maintains a pH of about 4.5 after about 1 week storage at about 60° C. In one aspect the appearance (e.g. viscosity, consistency and/or color) of the formulation is unchanged after about 4 weeks storage at about 25° C./60% RH, about 30° C./75% RH or about 40° C./75% RH. In one aspect the appearance of the formulation is unchanged after about 1 week storage at about 60° C. In one aspect the oxymetazoline is present in an amount of from about 0.0075% to about 5% by weight. In one aspect the oxymetazoline is present in an amount of about 0.5%, about 1.0% or about 1.5% by weight. In one aspect the formulation comprises a vasoconstrictor. In a further aspect the vasoconstrictor is an alpha-adrenergic agonist. In a further aspect the vasoconstrictor is an imidazoline type alpha-adrenergic agonist, a non-imidazoline type alpha-adrenergic agonist, an alpha-1 adrenergic agonist, an alpha-2 adrenergic agonist, a selective alpha-adrenergic agonist, a non-selective alpha-adrenergic agonist, a selective alpha-1 adrenergic agonist, a selective alpha-2 adrenergic agonist, a non-selective alpha-1 adrenergic agonist, a non-selective alpha-2 adrenergic agonist or a combination thereof.

In one embodiment a cream formulation comprises an active pharmaceutical ingredient other than oxymetazoline, an emulsifier and an emollient. In one aspect the ratio of the emulsifier to the emollient is from about 0.7:1 to about 1.8:1. In a further aspect, the formulation comprises an emulsifer in a total amount of from about 1% to about 30% by weight. In a further aspect, the emulsifier comprises Tefose 63™. In a further aspect the emulsifier comprises a PEG-stearate, a glycol stearate or a combination thereof. In a further aspect the emulsifier is polyethylene glycol 6 (PEG-6), polyethylene glycol 32 (PEG-32), and glycol stearate. In a further aspect the hydrophilic-lipophilic balance of the emulsifier is from about 9.0 to about 17.0. In a further aspect the emulsifier comprises ethoxylated fatty acids. In a further aspect the emulsifier comprises cetostearyl alcohol. In a further aspect, the formulation comprises an emulsifer and an emollient, and the ratio of the emulsifier to the emollient comprises from about 0.7:1 to about 1.5:1. In a further aspect, the formulation further comprises an additive selected from the group consisting of preservatives, emulsion stabilizers, pH adjusters, chelating agents, viscosity modifiers, antioxidants, surfactants, emollients, opacifying agents, skin conditioners, buffers, fragrances and combinations thereof. In a further aspect, the active pharmaceutical ingredient is a topically active pharmaceutical or cosmetic agent. In a further aspect the active pharmaceutical ingredient is a systemically active pharmaceutical or cosmetic agent. In a further aspect the formulation comprises a pH from about 2.0 to about 7.0 at room temperature. In a further aspect the formulation comprises a pH from about 4.0 to about 5.5 at room temperature. In a further aspect the active pharmaceutical ingredient is in an amount of from about 0.0075% to about 50% by weight. In a further aspect, the active pharmaceutical ingredient is an imidazoline alpha-adrenergic agonist, a non-imidazoline alpha-adrenergic agonist, an alpha-1 adrenergic agonist, an alpha-2 adrenergic agonist, a selective alpha-adrenergic agonist, a non-selective alpha-adrenergic agonist, a selective alpha-1 adrenergic agonist, a selective alpha-2 adrenergic agonist, a non-selective alpha-1 adrenergic agonist, a non-selective alpha-2 adrenergic agonist or a combination thereof.

In one embodiment, a cream formulation comprises an emulsifier and an emollient, wherein a ratio of the emulsifier to the emollient is from about 0.7:1 to about 1.8:1 and wherein the formulation does not contain an active pharmaceutical ingredient.

In one embodiment, a pharmaceutical composition comprises an API other than oxymetazoline; an emulsifier; and an emollient; wherein a ratio of the emulsifier to the emollient comprises from about 0.7:1 to about 1.8:1, and wherein the composition is a cream.

In one embodiment, a pharmaceutical composition comprises an API other than oxymetazoline in an amount of from about 0.0075% to about 50% by weight of the pharmaceutical composition; an emulsifier in an amount of about 1% to about 30% by weight of the pharmaceutical composition; and an emollient in an amount of from about 1% to about 50% by weight of the pharmaceutical composition.

At least one embodiment provides a method of treating a skin condition selected from the group consisting of rosacea and symptoms associated with rosacea, including, for example, papules, pustules, phymas, telangiectasias or erythema associated with rosacea, other skin erythemas, telangiectasias, purpura or the like, and other manifestations associated therewith; other inflammatory conditions of the skin including, but not limited to, keratosis pilaris, lupus miliaris dissemniatus faciei, eczema, dermatitis, such as contact dermatitis, atopic dermatitis, seborrheic dermatitis, nummular dermatitis, generalized exfoliative dermatitis, statis dermatitis, neurodermatitis, lichen simplex chronicus, xerosis and xerotic dermatitis, dyshidrosis and dyshidrotic dermatitis, asteototic dermatitis or other conditions characterized by sensitive skin or a disturbance of the epidermal barrier; disorders characterized by rough, dry, cracked or fissured skin, disorders characterized by hyperkeratotic skin such as keratodermas and ichthyosisis and ichthyosiform dermatoses; disorders of hair follicles and sebaceous glands, such as acne, perioral dermatitis, and pseudofolliculitis barbae; disorders of sweat glands, such as miliaria, including, but not limited to, miliaria crystallina, miliaria rubra, miliaria profunda, miliaria pustulosa; sunburn, chronic actinic damage, poikiloderma, radiation dermatitis, actinic purpura; other inflammatory dermatoses, reactions and conditions of the skin, including, but not limited to, psoriasis, drug eruptions, erythema multiforme, erythema nodosum, and granuloma annulare; diseases and conditions characterized by bleeding or bruising such as petechiae, ecchymosis, purpura and the like including any accumulation of blood in the skin due to vascular extravasation, irrespective of size or cause, bleeding or bruising due to any skin injury which may include any trauma including surgical or procedural trauma; infection, inflammatory dermatoses or inflammation due to any cause comprising administering a cream formulation of an embodiment described herein.

EXAMPLES

Although the present invention has been described in considerable detail with reference to certain preferred embodiments thereof, other versions are possible. Therefore, the spirit and scope of the appended claims should not be limited to the description and the preferred versions contained within this specification. Various aspects of the present invention will be illustrated with reference to the following non-limiting examples.

Example 1

The amount per batch (kg) for each component of the oxymetazoline cream prepared as described below are provided with their concentration by weight of the total cream in Table 1. Table 2 illustrates a function and amount per batch (kg) for each component of the cream prepared as described below with each component's concentration by weight of the total cream wherein Tefose™ 63 is replaced by a mixture of PEG-6 Stearate, Glycol Stearate and PEG-32 Stearate.

Solution 1: In a 2 L glass beaker, 44.0 g of methylparaben, NF and 11.0 g of propylparaben, NF was dissolved into 880 g of polyethylene glycol by mixing with a magnetic stirrer until the mixture became homogeneous. Once the parabens were dissolved, 176.0 g of phenoxyethanol Ph Eur was added to the mixture.

Solution 2: In a separate 36 L capacity stainless steel beaker, heat purified 11305 g of purified water was heated to 75° C. to 78° C. using a hot plate, and 2.2 g of disodium edetate (EDTA), USP, 44.0 g of anhydrous citric acid, USP, and 66.0 g of sodium citrate dehydrate, USP was added to the heated water using a low mixing speed (450 rpm) while maintaining the temperature of the solution at 75° C. to 78° C.

Oil Phase: Into a reactor vessel, preferably an anchor-type, propeller-equipped reactor vessel, 11.0 g of butylated hydroxytoluene, NF, 1760 g of Tefose™ 63 (PEG-& glycol & PEG-32 Stearate), 1760 g of cetostearyl alcohol, NF, 1540 g of triglycerides medium chain, NF (caprylic capric triglycerides), 1540 g of diisopropyl adipate, 1540 g of oleyl alcohol, NF, 440 g of lanolin, USP, 440 g of macrogol (6) cetostearyl ether (Cremophor A-6), Ph Eur, and 440 g of macrogol (25) cetostearyl ether (Cremophor A-25), Ph Eur was added, and the mixture was heated to 73° C. to 75° C. while mixing at a low mixing speed (50 rpm).

While the oil phase was melting, oxymetazoline hydrochloride, USP was dissolved into Solution 2 to create the aqueous phase, and evaporated water was replaced by adding 10.9 g of purified water to the stainless steel beaker. Solution 1 was then added to the aqueous phase while the temperature was maintained at 75° C. to 78° C. with low speed mixing (250 rpm). The resulting aqueous phase solution was than added at a moderate speed to the oil phase in the reactor vessel, preferably an anchor-type, propeller-equipped reactor vessel, with low speed mixing (50 rpm), and stirring was continued until the temperature in the reactor was 40° C. The mixing speed was then lowered to 30 rpm, and the temperature was reduced to 35° C. When 35° C. was reached, the mixing speed was again lowered to 20 rpm. The resulting white cream was manually discharged from the reactor and stored in a two 12 L stainless steel beakers.

TABLE 1

COMPOSITION OF OXYMETAZOLINE CREAM TRIAL 36

| Ingredient | % W/W | Amount per Batch (g) |
|---|---|---|
| Oxymetazoline hydrochloride, USP | 0.01 | 2.2 |
| 2-Phenoxyethanol, Ph Eur | 0.80 | 176 |

TABLE 1-continued

COMPOSITION OF OXYMETAZOLINE CREAM TRIAL 36

| Ingredient | % W/W | Amount per Batch (g) |
|---|---|---|
| Methylparaben, NF | 0.20 | 44 |
| Propylparaben, NF | 0.05 | 11 |
| Edetate Disodium, Dihydrate, USP | 0.01 | 2.2 |
| Butylated Hydroxytoluene, NF | 0.05 | 11 |
| Polyethylene Glycol 300, NF | 4.0 | 880 |
| Tefose 63 | 8.0 | 1760 |
| Cetostearyl alcohol, NF | 8.0 | 1760 |
| Triglycerides medium chain, NF (caprylic capric/triglycerides) | 7.0 | 1540 |
| Diisopropyl adipate | 7.0 | 1540 |
| Oleyl alcohol, NF | 7.0 | 1540 |
| Lanolin, USP | 2.0 | 440 |
| Cremophor A-6 | 2.0 | 440 |
| Cremophor A-25 | 2.0 | 440 |
| Purified Water, USP (1) | 51.38 | 11305.8 |
| Purified Water, USP (2) | QS | QS |
| Anhydrous Citric Acid, USP | 0.20 | 44 |
| Sodium Citrate Dihydrate, USP | 0.30 | 66 |

TABLE 2

COMPOSITION OF OXYMETAZOLINE CREAM TRIAL 36

| % W/W | Ingredients | Function |
|---|---|---|
| QS | Oxymetazoline Hydrochloride, USP | Active |
| 0.80 | Phenoxyethanol, Ph Eur | Antimicrobial preservative |
| 0.20 | Methylparaben, NF | Antimicrobial preservative |
| 0.05 | Propylparaben, NF | Antimicrobial preservative |
| 0.01 | Disodium Edetate, USP | Chelating agent |
| 0.05 | Butylated Hydroxytoluene, NF | Anti-oxidant |
| 4.00 | Polyethylene Glycol 300, NF | Humectant |
| 5.00 | PEG-6 Stearate | Emulsifier |
| 1.50 | Glycol Stearate | Emulsifier |
| 1.50 | PEG-32 Stearate | Emulsifier |
| 8.00 | Cetostearyl alcohol, NF | Emollient, stiffening agent and emulsion stabilizer |
| 7.00 | Triglycerides medium chain, NF (Caprylic capric triglycerides) | Emollient, oil component |
| 7.00 | Diisopropyl adipate | Emollient, oil component |
| 7.00 | Oleyl Alcohol, NF | Emollient, oil component |
| 2.00 | Lanolin, USP | Emollient, oil component |
| 2.00 | Macrogol (6) Cetostearyl Ether (Cremophor A-6), Ph Eur | Non-ionic o/w emulsifier, consistency enhancer |
| 2.00 | Macrogol (25) Cetostearyl Ether (Cremophor A-25), Ph Eur | Non-ionic o/w emulsifier, consistency enhancer |
| 51.38 | Purified Water, USP | Vehicle |
| 0.20 | Anhydrous Citric Acid, USP | Buffering agent |
| 0.30 | Sodium Citrate Dihydrate, USP | Buffering agent |
| 100.00 | | |

Example 2

Oxymetazoline creams having a variety of formulations were prepared as described in Example 1 in order to obtain a cream which was cosmetically acceptable and had enough consistency to support prolonged exposure at 40° C. without losing its physical integrity. Trial 1 was a base formulation without any API. Trial 2 included 0.1% API to determine the impact that the API would have on the base formulation. The consistency (Viscosity value) revealed that there was no immediate physical impact of the active at 0.1% concentration on the physical integrity of the cream base as compared to the plain base in Trial 1. Trials 3, 5 and 6 were formulations prepared during development work. Trials 7-11 were formulations prepared for the first stability study. Trials 12-13 were formulations containing higher concentrations of oxymetazoline (2% and 1%, respectively). Trials 15-18 were formulations made for toxicology studies. Batches A and B were the same and were combined to make a larger batch for the toxicology studies. Trial 19 was a formulation without preservatives for analytical method development. Trials 20-34 were the first round of optimization formulations. Trials 35-37 were buffered at pH 4.5 and included a high content of cetostearyl alcohol and Tefose™ 63. Trials 38-41 further optimized the Trial 36 formulation with 0.5%, 1%, 2% API and a placebo. Trials 42-43 further optimized the Trial 36 formulation with 0.01%, and 0.15% API and were used in the permeation flux studies. Trial 45 was a large engineering batch of the Trial 36 formulation. Trial 46-48 and 51 were made for analytical method development. Trials 49-50 were made for toxicology studies and contain 0.05% and 0% API, respectively.

TABLE 3

PREPARATION OF OXYMETAZOLINE CREAM: TRIALS 1-7A (% W/W)

| | Trial 1 | Trial 2 | Trial 3 | Trial 4 | Trial 5 | Trial 6 | Trial 7 | Trial 7A |
|---|---|---|---|---|---|---|---|---|
| Oxymetazoline HCl | 0.000 | 0.100 | 0.025 | NA | 0.100 | 0.050 | 0.150 | 0.025 |
| Phenoxyethanol | 0.800 | 0.800 | 0.800 | NA | 0.800 | 0.800 | 0.800 | 0.800 |
| Methylparaben | 0.200 | 0.200 | 0.200 | NA | 0.200 | 0.200 | 0.200 | 0.200 |
| Propylparaben | 0.050 | 0.050 | 0.050 | NA | 0.050 | 0.050 | 0.050 | 0.050 |
| Disodium Edetate | 0.010 | 0.010 | 0.010 | NA | 0.010 | 0.010 | 0.010 | 0.010 |
| Butylated Hydroxytoluene | 0.050 | 0.050 | 0.050 | NA | 0.050 | 0.050 | 0.050 | 0.050 |
| Polyethylene Glycol 300 | 4.000 | 4.000 | 4.000 | NA | 4.000 | 4.000 | 4.000 | 4.000 |
| Tefose 63 | 7.500 | 7.500 | 8.000 | NA | 8.000 | 8.000 | 8.000 | 8.000 |
| Cetostearyl alcohol | 4.000 | 4.000 | 5.000 | NA | 5.000 | 5.000 | 5.000 | 5.000 |
| Triglycerides medium chain | 7.000 | 7.000 | 7.000 | NA | 7.000 | 7.000 | 7.000 | 7.000 |
| Diisopropyl adipate | 7.000 | 7.000 | 7.000 | NA | 7.000 | 7.000 | 7.000 | 7.000 |
| Oleyl Alcohol | 7.000 | 7.000 | 7.000 | NA | 7.000 | 7.000 | 7.000 | 7.000 |
| Lanolin | 2.000 | 2.000 | 2.000 | NA | 2.000 | 2.000 | 2.000 | 2.000 |
| Macrogol (6) Cetostearyl Ether | 2.000 | 2.000 | 2.000 | NA | 2.000 | 2.000 | 2.000 | 2.000 |
| Macrogol (25) Cetostearyl Ether | 2.000 | 2.000 | 2.000 | NA | 2.000 | 2.000 | 2.000 | 2.000 |
| Anhydrous Citric Acid | 0.000 | 0.000 | 0.000 | NA | 0.000 | 0.000 | 0.000 | 0.000 |

TABLE 3-continued

PREPARATION OF OXYMETAZOLINE CREAM: TRIALS 1-7A (% W/W)

|  | Trial 1 | Trial 2 | Trial 3 | Trial 4 | Trial 5 | Trial 6 | Trial 7 | Trial 7A |
|---|---|---|---|---|---|---|---|---|
| Sodium Citrate Dihydrate | 0.000 | 0.000 | 0.000 | NA | 0.000 | 0.000 | 0.000 | 0.000 |
| Hydroxyethyl Cellulose | 0.000 | 0.000 | 0.000 | NA | 0.000 | 0.000 | 0.000 | 0.000 |
| Lipoid S-75 | 0.000 | 0.000 | 0.000 | NA | 0.000 | 0.000 | 0.000 | 0.000 |
| Trizma | 0.000 | 0.000 | 0.000 | NA | 0.000 | 0.000 | 0.000 | 0.000 |
| Purified Water | 56.390 | 56.290 | 54.865 | NA | 54.790 | 54.840 | 54.740 | 54.865 |

TABLE 4

PREPARATION OF OXYMETAZOLINE CREAM: TRIALS 8-15A (% W/W)

|  | Trial 8 | Trial 9 | Trial 10 | Trial 11 | Trial 12 | Trial 13 | Trial 14 | Trial 15A |
|---|---|---|---|---|---|---|---|---|
| Oxymetazoline HCl | 0.100 | 0.050 | 0.150 | 0.010 | 2.000 | 1.000 | NA | 2.000 |
| Phenoxyethanol | 0.800 | 0.800 | 0.800 | 0.800 | 0.800 | 0.800 | NA | 0.800 |
| Methylparaben | 0.200 | 0.200 | 0.200 | 0.200 | 0.200 | 0.200 | NA | 0.200 |
| Propylparaben | 0.050 | 0.050 | 0.050 | 0.050 | 0.050 | 0.050 | NA | 0.050 |
| Disodium Edetate | 0.010 | 0.010 | 0.010 | 0.010 | 0.010 | 0.010 | NA | 0.010 |
| Butylated Hydroxytoluene | 0.050 | 0.050 | 0.050 | 0.050 | 0.050 | 0.050 | NA | 0.050 |
| Polyethylene Glycol 300 | 4.000 | 4.000 | 4.000 | 4.000 | 4.000 | 4.000 | NA | 4.000 |
| Tefose 63 | 8.000 | 8.000 | 8.000 | 8.000 | 8.000 | 8.000 | NA | 8.000 |
| Cetostearyl alcohol | 5.000 | 5.000 | 5.000 | 5.000 | 5.000 | 5.000 | NA | 5.000 |
| Triglycerides medium chain | 7.000 | 7.000 | 7.000 | 7.000 | 7.000 | 7.000 | NA | 7.000 |
| Diisopropyl adipate | 7.000 | 7.000 | 7.000 | 7.000 | 7.000 | 7.000 | NA | 7.000 |
| Oleyl Alcohol | 7.000 | 7.000 | 7.000 | 7.000 | 7.000 | 7.000 | NA | 7.000 |
| Lanolin | 2.000 | 2.000 | 2.000 | 2.000 | 2.000 | 2.000 | NA | 2.000 |
| Macrogol (6) Cetostearyl Ether | 2.000 | 2.000 | 2.000 | 2.000 | 2.000 | 2.000 | NA | 2.000 |
| Macrogol (25) Cetostearyl Ether | 2.000 | 2.000 | 2.000 | 2.000 | 2.000 | 2.000 | NA | 2.000 |
| Anhydrous Citric Acid | 0.000 | 0.000 | 0.000 | 0.000 | 0.000 | 0.000 | NA | 0.000 |
| Sodium Citrate Dihydrate | 0.000 | 0.000 | 0.000 | 0.000 | 0.000 | 0.000 | NA | 0.000 |
| Hydroxyethyl Cellulose | 0.000 | 0.000 | 0.000 | 0.000 | 0.000 | 0.000 | NA | 0.000 |
| Lipoid S-75 | 0.000 | 0.000 | 0.000 | 0.000 | 0.000 | 0.000 | NA | 0.000 |
| Trizma | 0.000 | 0.000 | 0.000 | 0.000 | 0.000 | 0.000 | NA | 0.000 |
| Purified Water | 54.790 | 54.840 | 54.740 | 54.880 | 52.890 | 53.890 | NA | 52.890 |

TABLE 5

PREPARATION OF OXYMETAZOLINE CREAM: TRIALS 15B-19 (% W/W)

|  | Trial 15B | Trial 16A | Trial 16B | Trial 17A | Trial 17B | Trial 18A | Trial 18B | Trial 19 |
|---|---|---|---|---|---|---|---|---|
| Oxymetazoline HCl | 2.000 | 1.000 | 1.000 | 0.500 | 0.500 | 0.000 | 0.000 | 0.150 |
| Phenoxyethanol | 0.800 | 0.800 | 0.800 | 0.800 | 0.800 | 0.800 | 0.800 | 0.000 |
| Methylparaben | 0.200 | 0.200 | 0.200 | 0.200 | 0.200 | 0.200 | 0.200 | 0.000 |
| Propylparaben | 0.050 | 0.050 | 0.050 | 0.050 | 0.050 | 0.050 | 0.050 | 0.000 |
| Disodium Edetate | 0.010 | 0.010 | 0.010 | 0.010 | 0.010 | 0.010 | 0.010 | 0.010 |
| Butylated Hydroxytoluene | 0.050 | 0.050 | 0.050 | 0.050 | 0.050 | 0.050 | 0.050 | 0.050 |
| Polyethylene Glycol 300 | 4.000 | 4.000 | 4.000 | 4.000 | 4.000 | 4.000 | 4.000 | 4.000 |
| Tefose 63 | 8.000 | 8.000 | 8.000 | 8.000 | 8.000 | 8.000 | 8.000 | 8.000 |
| Cetostearyl alcohol | 5.000 | 5.000 | 5.000 | 5.000 | 5.000 | 5.000 | 5.000 | 5.000 |
| Triglycerides medium chain | 7.000 | 7.000 | 7.000 | 7.000 | 7.000 | 7.000 | 7.000 | 7.000 |
| Diisopropyl adipate | 7.000 | 7.000 | 7.000 | 7.000 | 7.000 | 7.000 | 7.000 | 7.000 |
| Oleyl Alcohol | 7.000 | 7.000 | 7.000 | 7.000 | 7.000 | 7.000 | 7.000 | 7.000 |
| Lanolin | 2.000 | 2.000 | 2.000 | 2.000 | 2.000 | 2.000 | 2.000 | 2.000 |
| Macrogol (6) Cetostearyl Ether | 2.000 | 2.000 | 2.000 | 2.000 | 2.000 | 2.000 | 2.000 | 2.000 |
| Macrogol (25) Cetostearyl Ether | 2.000 | 2.000 | 2.000 | 2.000 | 2.000 | 2.000 | 2.000 | 2.000 |
| Anhydrous Citric Acid | 0.000 | 0.000 | 0.000 | 0.000 | 0.000 | 0.000 | 0.000 | 0.000 |
| Sodium Citrate Dihydrate | 0.000 | 0.000 | 0.000 | 0.000 | 0.000 | 0.000 | 0.000 | 0.000 |
| Hydroxyethyl Cellulose | 0.000 | 0.000 | 0.000 | 0.000 | 0.000 | 0.000 | 0.000 | 0.000 |
| Lipoid S-75 | 0.000 | 0.000 | 0.000 | 0.000 | 0.000 | 0.000 | 0.000 | 0.000 |
| Trizma | 0.000 | 0.000 | 0.000 | 0.000 | 0.000 | 0.000 | 0.000 | 0.000 |
| Purified Water | 52.890 | 53.890 | 53.890 | 54.390 | 54.390 | 54.890 | 54.890 | 55.790 |

TABLE 6

PREPARATION OF OXYMETAZOLINE CREAM: TRIALS 20-27 (% W/W)

| | Trial 20 | Trial 21 | Trial 22 | Trial 23 | Trial 24 | Trial 25 | Trial 26 | Trial 27 |
|---|---|---|---|---|---|---|---|---|
| Oxymetazoline HCl | 0.010 | 0.150 | 0.010 | 0.010 | 0.010 | 0.010 | 0.010 | 0.010 |
| Phenoxyethanol | 0.800 | 0.800 | 0.800 | 0.800 | 0.800 | 0.800 | 0.800 | 0.800 |
| Methylparaben | 0.200 | 0.200 | 0.200 | 0.200 | 0.200 | 0.200 | 0.200 | 0.200 |
| Propylparaben | 0.050 | 0.050 | 0.050 | 0.050 | 0.050 | 0.050 | 0.050 | 0.050 |
| Disodium Edetate | 0.010 | 0.010 | 0.010 | 0.010 | 0.010 | 0.010 | 0.010 | 0.010 |
| Butylated Hydroxytoluene | 0.050 | 0.050 | 0.050 | 0.050 | 0.050 | 0.050 | 0.050 | 0.050 |
| Polyethylene Glycol 300 | 4.000 | 4.000 | 4.000 | 4.000 | 4.000 | 4.000 | 4.000 | 4.000 |
| Tefose 63 | 8.000 | 8.000 | 8.000 | 8.000 | 8.000 | 8.000 | 10.000 | 10.000 |
| Cetostearyl alcohol | 5.000 | 5.000 | 5.000 | 5.000 | 5.000 | 5.000 | 8.000 | 10.000 |
| Triglycerides medium chain | 7.000 | 7.000 | 7.000 | 7.000 | 7.000 | 7.000 | 7.000 | 7.000 |
| Diisopropyl adipate | 7.000 | 7.000 | 7.000 | 7.000 | 7.000 | 7.000 | 7.000 | 7.000 |
| Oleyl Alcohol | 7.000 | 7.000 | 7.000 | 7.000 | 7.000 | 7.000 | 7.000 | 7.000 |
| Lanolin | 2.000 | 2.000 | 2.000 | 2.000 | 2.000 | 2.000 | 2.000 | 2.000 |
| Macrogol (6) Cetostearyl Ether | 2.000 | 2.000 | 2.000 | 2.000 | 2.000 | 2.000 | 2.000 | 2.000 |
| Macrogol (25) Cetostearyl Ether | 2.000 | 2.000 | 2.000 | 2.000 | 2.000 | 2.000 | 2.000 | 2.000 |
| Anhydrous Citric Acid | 0.000 | 0.000 | 0.200 | 0.000 | 0.100 | 0.200 | 0.000 | 0.000 |
| Sodium Citrate Dihydrate | 0.000 | 0.000 | 0.300 | 0.000 | 0.450 | 0.300 | 0.000 | 0.000 |
| Hydroxyethyl Cellulose | 0.000 | 0.000 | 0.000 | 0.500 | 0.000 | 0.500 | 0.000 | 0.000 |
| Lipoid S-75 | 0.000 | 0.000 | 0.000 | 0.000 | 0.000 | 0.000 | 0.000 | 0.000 |
| Trizma | 0.000 | 0.000 | 0.000 | 0.000 | 0.000 | 0.000 | 0.000 | 0.000 |
| Purified Water | 54.880 | 54.740 | 54.380 | 54.380 | 54.330 | 53.880 | 49.880 | 47.880 |

TABLE 7

PREPARATION OF OXYMETAZOLINE CREAM: TRIALS 28-35 (% W/W)

| | Trial 28 | Trial 29 | Trial 30 | Trial 31 | Trial 32 | Trial 33 | Trial 34 | Trial 35 |
|---|---|---|---|---|---|---|---|---|
| Oxymetazoline HCl | 0.010 | 0.010 | 0.010 | 0.010 | 0.010 | 0.150 | 0.150 | 0.010 |
| Phenoxyethanol | 0.800 | 0.800 | 0.800 | 0.800 | 0.800 | 0.800 | 0.800 | 0.800 |
| Methylparaben | 0.200 | 0.200 | 0.200 | 0.200 | 0.200 | 0.200 | 0.200 | 0.200 |
| Propylparaben | 0.050 | 0.050 | 0.050 | 0.050 | 0.050 | 0.050 | 0.050 | 0.050 |
| Disodium Edetate | 0.010 | 0.010 | 0.010 | 0.010 | 0.010 | 0.010 | 0.010 | 0.010 |
| Butylated Hydroxytoluene | 0.050 | 0.050 | 0.050 | 0.050 | 0.050 | 0.050 | 0.050 | 0.050 |
| Polyethylene Glycol 300 | 4.000 | 4.000 | 4.000 | 4.000 | 4.000 | 4.000 | 4.000 | 4.000 |
| Tefose 63 | 8.000 | 8.000 | 8.000 | 8.000 | 8.000 | 8.000 | 8.000 | 10.000 |
| Cetostearyl alcohol | 5.000 | 5.000 | 5.000 | 5.000 | 5.000 | 5.000 | 5.000 | 10.000 |
| Triglycerides medium chain | 3.500 | 10.500 | 7.000 | 7.000 | 7.000 | 3.500 | 10.500 | 7.000 |
| Diisopropyl adipate | 3.500 | 10.500 | 7.000 | 7.000 | 7.000 | 3.500 | 10.500 | 7.000 |
| Oleyl Alcohol | 14.000 | 0.000 | 0.000 | 0.000 | 7.000 | 14.000 | 0.000 | 7.000 |
| Lanolin | 2.000 | 2.000 | 2.000 | 2.000 | 2.000 | 2.000 | 2.000 | 2.000 |
| Macrogol (6) Cetostearyl Ether | 2.000 | 2.000 | 2.000 | 2.000 | 1.000 | 2.000 | 2.000 | 2.000 |
| Macrogol (25) Cetostearyl Ether | 2.000 | 2.000 | 2.000 | 2.000 | 1.000 | 2.000 | 2.000 | 2.000 |
| Anhydrous Citric Acid | 0.000 | 0.000 | 0.000 | 0.000 | 0.000 | 0.000 | 0.000 | 0.200 |
| Sodium Citrate Dihydrate | 0.000 | 0.000 | 0.000 | 0.000 | 0.000 | 0.000 | 0.000 | 0.300 |
| Hydroxyethyl Cellulose | 0.000 | 0.000 | 0.000 | 0.000 | 0.000 | 0.000 | 0.000 | 0.000 |
| Lipoid S-75 | 0.000 | 0.000 | 2.000 | 0.000 | 0.000 | 0.000 | 0.000 | 0.000 |
| Trizma | 0.000 | 0.000 | 0.000 | 0.000 | 0.000 | 0.000 | 0.000 | 0.000 |
| Purified Water | 54.880 | 54.880 | 59.880 | 61.880 | 56.880 | 54.740 | 54.740 | 47.380 |

TABLE 8

PREPARATION OF OXYMETAZOLINE CREAM: TRIALS 36-40A (% W/W)

| | Trial 36 | Trial 37 | Trial 38 | Trial 38A | Trial 39 | Trial 39A | Trial 40 | Trial 40A |
|---|---|---|---|---|---|---|---|---|
| Oxymetazoline HCl | 0.010 | 0.010 | 0.000 | 0.000 | 0.500 | 0.500 | 1.000 | 1.000 |
| Phenoxyethanol | 0.800 | 0.800 | 0.800 | 0.800 | 0.800 | 0.800 | 0.800 | 0.800 |
| Methylparaben | 0.200 | 0.200 | 0.200 | 0.200 | 0.200 | 0.200 | 0.200 | 0.200 |
| Propylparaben | 0.050 | 0.050 | 0.050 | 0.050 | 0.050 | 0.050 | 0.050 | 0.050 |

TABLE 8-continued

PREPARATION OF OXYMETAZOLINE CREAM: TRIALS 36-40A (% W/W)

| | Trial 36 | Trial 37 | Trial 38 | Trial 38A | Trial 39 | Trial 39A | Trial 40 | Trial 40A |
|---|---|---|---|---|---|---|---|---|
| Disodium Edetate | 0.010 | 0.010 | 0.010 | 0.010 | 0.010 | 0.010 | 0.010 | 0.010 |
| Butylated Hydroxytoluene | 0.050 | 0.050 | 0.050 | 0.050 | 0.050 | 0.050 | 0.050 | 0.050 |
| Polyethylene Glycol 300 | 4.000 | 4.000 | 4.000 | 4.000 | 4.000 | 4.000 | 4.000 | 4.000 |
| Tefose 63 | 8.000 | 9.000 | 8.000 | 8.000 | 8.000 | 8.000 | 8.000 | 8.000 |
| Cetostearyl alcohol | 8.000 | 7.000 | 8.000 | 8.000 | 8.000 | 8.000 | 8.000 | 8.000 |
| Triglycerides medium chain | 7.000 | 7.000 | 7.000 | 7.000 | 7.000 | 7.000 | 7.000 | 7.000 |
| Diisopropyl adipate | 7.000 | 7.000 | 7.000 | 7.000 | 7.000 | 7.000 | 7.000 | 7.000 |
| Oleyl Alcohol | 7.000 | 7.000 | 7.000 | 7.000 | 7.000 | 7.000 | 7.000 | 7.000 |
| Lanolin | 2.000 | 2.000 | 2.000 | 2.000 | 2.000 | 2.000 | 2.000 | 2.000 |
| Macrogol (6) Cetostearyl Ether | 2.000 | 2.000 | 2.000 | 2.000 | 2.000 | 2.000 | 2.000 | 2.000 |
| Macrogol (25) Cetostearyl Ether | 2.000 | 2.000 | 2.000 | 2.000 | 2.000 | 2.000 | 2.000 | 2.000 |
| Anhydrous Citric Acid | 0.200 | 0.200 | 0.200 | 0.200 | 0.200 | 0.200 | 0.200 | 0.200 |
| Sodium Citrate Dihydrate | 0.300 | 0.300 | 0.300 | 0.300 | 0.300 | 0.300 | 0.300 | 0.300 |
| Hydroxyethyl Cellulose | 0.000 | 0.000 | 0.000 | 0.000 | 0.000 | 0.000 | 0.000 | 0.000 |
| Lipoid S-75 | 0.000 | 0.000 | 0.000 | 0.000 | 0.000 | 0.000 | 0.000 | 0.000 |
| Trizma | 0.000 | 0.000 | 0.000 | 0.000 | 0.000 | 0.000 | 0.000 | 0.000 |
| Purified Water | 51.380 | 51.380 | 51.390 | 51.390 | 50.890 | 50.890 | 50.390 | 50.390 |

TABLE 9

PREPARATION OF OXYMETAZOLINE CREAM: TRIALS 41-47 (% W/W)

| | Trial 41 | Trial 41A | Trial 42 | Trial 43 | Trial 44 | Trial 45 | Trial 46 | Trial 47 |
|---|---|---|---|---|---|---|---|---|
| Oxymetazoline HCl | 2.000 | 2.000 | 0.010 | 0.150 | NA | 0.000 | 0.500 | 0.250 |
| Phenoxyethanol | 0.800 | 0.800 | 0.800 | 0.800 | NA | 0.800 | 0.800 | 0.800 |
| Methylparaben | 0.200 | 0.200 | 0.200 | 0.200 | NA | 0.200 | 0.200 | 0.200 |
| Propylparaben | 0.050 | 0.050 | 0.050 | 0.050 | NA | 0.050 | 0.050 | 0.050 |
| Disodium Edetate | 0.010 | 0.010 | 0.010 | 0.010 | NA | 0.010 | 0.010 | 0.010 |
| Butylated Hydroxytoluene | 0.050 | 0.050 | 0.050 | 0.050 | NA | 0.050 | 0.050 | 0.050 |
| Polyethylene Glycol 300 | 4.000 | 4.000 | 4.000 | 4.000 | NA | 4.000 | 4.000 | 4.000 |
| Tefose 63 | 8.000 | 8.000 | 8.000 | 8.000 | NA | 8.000 | 8.000 | 8.000 |
| Cetostearyl alcohol | 8.000 | 8.000 | 8.000 | 8.000 | NA | 8.000 | 8.000 | 8.000 |
| Triglycerides medium chain | 7.000 | 7.000 | 7.000 | 7.000 | NA | 7.000 | 7.000 | 7.000 |
| Diisopropyl adipate | 7.000 | 7.000 | 7.000 | 7.000 | NA | 7.000 | 7.000 | 7.000 |
| Oleyl Alcohol | 7.000 | 7.000 | 7.000 | 7.000 | NA | 7.000 | 7.000 | 7.000 |
| Lanolin | 2.000 | 2.000 | 2.000 | 2.000 | NA | 2.000 | 2.000 | 2.000 |
| Macrogol (6) Cetostearyl Ether | 2.000 | 2.000 | 2.000 | 2.000 | NA | 2.000 | 2.000 | 2.000 |
| Macrogol (25) Cetostearyl Ether | 2.000 | 2.000 | 2.000 | 2.000 | NA | 2.000 | 2.000 | 2.000 |
| Anhydrous Citric Acid | 0.200 | 0.200 | 0.200 | 0.200 | NA | 0.200 | 0.200 | 0.200 |
| Sodium Citrate Dihydrate | 0.300 | 0.300 | 0.300 | 0.300 | NA | 0.300 | 0.300 | 0.300 |
| Hydroxyethyl Cellulose | 0.000 | 0.000 | 0.000 | 0.000 | NA | 0.000 | 0.000 | 0.000 |
| Lipoid S-75 | 0.000 | 0.000 | 0.000 | 0.000 | NA | 0.000 | 0.000 | 0.000 |
| Trizma | 0.000 | 0.000 | 0.000 | 0.000 | NA | 0.000 | 0.000 | 0.000 |
| Purified Water | 49.390 | 49.390 | 51.380 | 51.240 | NA | 51.390 | 50.890 | 51.140 |

TABLE 10

PREPARATION OF OXYMETAZOLINE CREAM: TRIALS 48-51 (% W/W)

|  | Trial 48 | Trial 49 | Trial 50 | Trial 51 |
|---|---|---|---|---|
| Oxymetazoline HCl | 0.100 | 0.050 | 0.000 | 0.150 |
| Phenoxyethanol | 0.800 | 0.800 | 0.800 | 0.800 |
| Methylparaben | 0.200 | 0.200 | 0.200 | 0.200 |
| Propylparaben | 0.050 | 0.050 | 0.050 | 0.050 |
| Disodium Edetate | 0.010 | 0.010 | 0.010 | 0.010 |
| Butylated Hydroxytoluene | 0.050 | 0.050 | 0.050 | 0.050 |
| Polyethylene Glycol 300 | 4.000 | 4.000 | 4.000 | 4.000 |

TABLE 10-continued

PREPARATION OF OXYMETAZOLINE CREAM: TRIALS 48-51 (% W/W)

|  | Trial 48 | Trial 49 | Trial 50 | Trial 51 |
|---|---|---|---|---|
| Tefose 63 | 8.000 | 8.000 | 8.000 | 8.000 |
| Cetostearyl alcohol | 8.000 | 8.000 | 8.000 | 8.000 |
| Triglycerides medium chain | 7.000 | 7.000 | 7.000 | 7.000 |
| Diisopropyl adipate | 7.000 | 7.000 | 7.000 | 7.000 |
| Oleyl Alcohol | 7.000 | 7.000 | 7.000 | 7.000 |
| Lanolin | 2.000 | 2.000 | 2.000 | 2.000 |
| Macrogol (6) Cetostearyl Ether | 2.000 | 2.000 | 2.000 | 2.000 |
| Macrogol (25) Cetostearyl Ether | 2.000 | 2.000 | 2.000 | 2.000 |
| Anhydrous Citric Acid | 0.200 | 0.200 | 0.200 | 0.000 |
| Sodium Citrate Dihydrate | 0.300 | 0.300 | 0.300 | 0.000 |
| Hydroxyethyl Cellulose | 0.000 | 0.000 | 0.000 | 0.000 |
| Lipoid S-75 | 0.000 | 0.000 | 0.000 | 0.000 |
| Trizma | 0.000 | 0.000 | 0.000 | 0.000 |
| Purified Water | 51.290 | 51.340 | 51.390 | 51.740 |

The purpose of this protocol was to perform a stability study on Oxymetazoline Topical Creams, 0.05%, 0.10% and 0.15%. The creams were packaged into two packaging configurations; 30-g polyethylene tubes and 30-g glaminate tubes. Approximately 120 tubes of each cream concentration were prepared. The creams were placed on stability for up to 36 months at the nominal storage condition of 25° C./60% RH and for 6 months at accelerated conditions of 40° C./75% RH. Some samples were also stored at the intermediate condition, 30° C./75% RH. The results of this stability study can be found in Tables 11-13. The pH of the product exhibited a tendency to decrease over time. This tendency appeared to be more pronounced in the samples stored at 40° C./75% RH. The observed appearance of the product at 40° C./75% RH indicated that there was a portion of the cream that melted to the point of becoming a liquid. Both of these issues represented a concern for the long term stability of the cream formulation. It is noted from the stand point of chemical stability of the drug, there was no appreciable drop in potency and there was a very low presence of impurities on the samples tested.

TABLE 11

STABILITY STUDY RESULTS - PRODUCT STORED IN POLYETHYLENE TUBES

| Parameters | Initial@Room Temperature | 40°°C./75% RH,. 2 Weeks | 40°°C./75% RH,. 1 Month | 25°°C./60% RH,. 1 Month | 30°°C./65% RH,. 1 Month |
|---|---|---|---|---|---|
| Oxymetazoline HCl Creams 0.01% | | | | | |
| Assay (% LC) | 101.0 | 102.0 | 96.0 | 101.5 | N/R |
| pH | 4.45 | 4.23 | 4.03 | 4.05 | 4.22 |
| Oxymetazoline HCl Creams 0.05% | | | | | |
| Assay (% LC) | 104.3 | 101.3 | 101.3 | 101.8 | 100.6 |
| CP (% Area) | 0.5 | 0.6 | 0.3 | 0.4 | N/R |
| pH | 4.29 | 4.16 | 3.98 | 4.09 | 4.14 |
| Oxymetazoline HCl Creams 0.10%. | | | | | |
| Assay (% LC) | 104.1 | 104.5 | 106.8 | 101.6 | 101.8 |
| CP (% Area) | 0.3 | 0.4 | 0.1 | 0.2 | N/R |
| pH | 4.39 | 4.22 | 3.98 | 4.05 | 4.11 |
| Oxymetazoline HCl Creams 0.15% | | | | | |
| Assay (% LC) | 100.9 | 99.2 | 102.1 | 99.8 | 100.1 |
| CP (% Area) | 0.2 | 0.3 | 0.1 | 0.2 | N/R |
| pH | 4.42 | 4.22 | 3.87 | 4.04 | 4.08 |

N/R = not reported

TABLE 12

STABILITY STUDY RESULTS - PRODUCT STORED IN GLAMINATE TUBES

| Parameters | Initial@Room Temperature | 40°°C./75% RH,. 2 Weeks | Avg | % RSD |
|---|---|---|---|---|
| Oxymetazoline HCl Creams 0.01% | | | | |
| Assay (% LC) | 101.5 | 101.0 | 101.3 | 0.3 |
| pH | 4.38 | 4.11 | 4.2 | 4.5 |
| Oxymetazoline HCl Creams 0.05% | | | | |
| Assay (% LC) | 102.8 | 105.0 | 103.9 | 1.5 |
| CP (% Area) | 0.7 | 0.8 | NA | NA |
| pH | 4.12 | 4.01 | 4.1 | 1.9 |
| Oxymetazoline HCl Creams 0.10%. | | | | |
| Assay (% LC) | 102.1 | 104.0 | 103.1 | 1.3 |
| CP (% Area) | 0.5 | 0.5 | NA | NA |
| pH | 4.13 | 4.01 | 4.1 | 2.1 |
| Oxymetazoline HCl Creams 0.15% | | | | |
| Assay (% LC) | 100.2 | 101.4 | 100.8 | 0.8 |
| CP(% Area) | 0.4 | 0.3 | NA | NA |
| pH | 4.10 | 3.98 | 4.0 | 2.1 |

The appearance of the samples stored for 1 month at 30° C. is within specification (White viscous cream); the homogeneous creams are similar to the samples stored at 25° C.

TABLE 13

STABILITY STUDY RESULTS - APPEARANCE OF PRODUCT IN POLYETHYLENE TUBES AND GLAMINATE TUBES

| Sample Description | Condition | Appearance |
|---|---|---|
| Polyethylene Tubes | | |
| Oxymetazoline HCl Creams 0.01% | 25° C./60% RH, 1 Month | White viscous cream |
| Oxymetazoline HCl Creams 0.05% | 25° C./60% RH, 1 Month | White viscous cream |
| Oxymetazoline HCl Creams 0.10% | 25° C./60% RH, 1 Month | White viscous cream |
| Oxymetazoline HCl Creams 0.15% | 25° C./60% RH, 1 Month | White viscous cream |
| Glaminate tubes | | |
| Oxymetazoline HCl Creams 0.01% | 40° C./75% RH, 1 Month | White viscous cream (not homogeneous) (A portion of the cream was transferred from the tube to a glass culture tube, a different consistency was observed) |
| Oxymetazoline HCl Creams 0.05% | 40° C./75% RH, 1 Month | White viscous cream (not homogeneous) (A portion of the cream was transferred from the tube to a glass culture tube, a different consistency was observed) |
| Oxymetazoline HCl Creams 0.10% | 40° C./75% RH, 1 Month | White viscous cream (not homogeneous) (A portion of the cream was transferred from the tube to a glass culture tube, a different consistency was observed) |
| Oxymetazoline HCl Creams 0.15% | 40° C./75% RH, 1 Month | White viscous cream (not homogeneous) (A portion of the cream was transferred from the tube to a glass culture tube, a different consistency was observed) |

Creams from Trials 20-34 were packaged into 30-g glaminate tubes. The creams were placed on stability for up to 4 weeks at storage condition of 25° C./60% RH at accelerated conditions of 60° C. and 40° C./75% RH and at the intermediate condition 30° C./75% RH. Trials 20-34 were tested initially and after 1 week. Viscosity was measure using a Brookfield RVT, C/P, Spindle CPE-52, 25 rpm, RT. The results are outlined in Table 14.

TABLE 14

STUDY RESULTS

| Sample ID | Viscosity cPs | pH (Initial) | pH (1 week)[2] | Appearance (Initial) | Appearance (1 week)[2] |
|---|---|---|---|---|---|
| Trial # 20 | 1836 | 4.45 | 4.58 | White Viscous Cream (Homogeneous) | White Viscous Cream (Homogeneous) |
| | | | 4.32 | | White Viscous Cream (Homogeneous) |
| | | | 4.16 | | White Viscous Cream (Homogeneous) |
| Trial #21 | 2367 | 3.92 | 3.89 | White Viscous Cream (Homogeneous) | White Viscous Cream (Homogeneous) |
| | | | 3.74 | | White Viscous Cream (Homogeneous) |
| | | | 3.58 | | White Viscous Cream (Homogeneous) |
| Trial #22 | 3450 | 4.57 | 4.55 | White Viscous Cream (Homogeneous) | White Viscous Cream (Homogeneous) |
| | | | 4.57 | | White Viscous Cream (Homogeneous) |
| | | | 4.54 | | White Viscous Cream (Homogeneous) |
| Trial #23 | 6895 | 4.24 | 4.15 | White Viscous Cream (Homogeneous) | White Viscous Cream (Homogeneous) |
| | | | 4.05 | | White Viscous Cream (Homogeneous) |
| | | | 3.93 | | White Viscous Cream with oily spots |
| Trial # 24 | 1608 | 5.58 | 5.51 | White Viscous Cream (Homogeneous) | White Viscous Cream (Homogeneous) |
| | | | 5.51 | | White Cream-Lotion |
| | | | 5.48 | | White Viscous Cream (Homogeneous) |

TABLE 14-continued

STUDY RESULTS

| Sample ID | Viscosity cPs | pH (Initial) | pH (1 week)[2] | Appearance (Initial) | Appearance (1 week)[2] |
|---|---|---|---|---|---|
| Trial #25 | 19183[1] | 4.66 | 4.58 | White Viscous Cream (Homogeneous) | White Viscous Cream (Homogeneous) |
| | | | 4.58 | | White Viscous Cream (Homogeneous) |
| | | | 4.58 | | White Viscous Cream (Homogeneous) |
| Trial #26 | 8458[1] | 3.94 | 3.69 | White Viscous Cream (Homogeneous) | White Viscous Cream (Homogeneous) |
| | | | 3.72 | | White Viscous Cream (Homogeneous) |
| | | | 3.64 | | White Viscous Cream (Homogeneous) |
| Trial #27 | 21067 | 4.44 | 4.17 | White Viscous Cream (Homogeneous) | White Viscous Cream (Homogeneous) |
| | | | 4.04 | | White Viscous Cream (Homogeneous) |
| | | | 3.87 | | White Viscous Cream (Homogeneous) |
| Trial #28 | 4695 | 4.61 | 4.54 | White Viscous Cream (Homogeneous) | White Viscous Cream (Homogeneous) |
| | | | 4.38 | | White Viscous Cream (Homogeneous) |
| | | | 4.18 | | White Viscous Cream (Homogeneous) |
| Trial #29 | 4686 | 4.53 | 4.41 | White Viscous Cream (Homogeneous) | White Viscous Cream (Homogeneous) |
| | | | 4.26 | | White Viscous Cream (Homogeneous) |
| | | | 4.23 | | White Cream-Lotion |
| Trial #30 | 6931 | 3.64 | 3.65 | Off-White Viscous Cream (Homogeneous) | Off-White Viscous Cream (Homogeneous) |
| | | | 3.56 | | Off-White Viscous Cream (Homogeneous) |
| | | | 3.55 | | Off-White Viscous Cream (Homogeneous) |
| Trial #31 | 1700 | 5.65 | 5.50 | White Viscous Cream (Homogeneous) | White Viscous Cream (Homogeneous) |
| | | | 5.36 | | White Viscous Cream (Homogeneous) |
| | | | 5.04 | | White Cream-Lotion |
| Trial #32 | 7269 | 3.75 | 3.69 | White Viscous Cream (Homogeneous) | White Viscous Cream (Homogeneous) |
| | | | 3.56 | | White soft Cream |
| | | | 3.62 | | White Lotion |
| Trial #33 | 2580 | 4.25 | 4.23 | White Viscous Cream (Homogeneous) | White Viscous Cream (Homogeneous) |
| | | | 4.07 | | White Cream-Lotion |
| | | | 3.87 | | White Viscous Cream (Homogeneous) |
| Trial #34 | 5639 | 4.09 | 4.03 | White Viscous Cream (Homogeneous) | White Viscous Cream (Homogeneous) |
| | | | 3.95 | | White Cream-Lotion |
| | | | 3.84 | | White Cream-Lotion |

[1]Modified Method used Speed @10 RPM
[2]Order: 25° C./60% RH 40° C./75%/RH 60° C.

Based on the stability studies of Trials 20-34, it appears that buffer systems stabilize the pH of the formulation. Formulations with high content of Cetostearyl Alcohol and Tefose™ 63 show a higher viscosity and a stable physical consistency when exposed to 60° C. temperature for 1 week. While not wishing to be bound by theory, this may be explained due to the two excipients' wax-like consistency and as such they impart a more rigid structure to the cream. Further evaluation of the stability data pointed to formulations which were optimized by buffers and higher wax-like material content. A buffer that could maintain a pH of about 4.5 was selected for Trials 35-37.

Example 3

Oxymetazoline creams formulated as Trials 35-37 were filled into 30 gram tubes and stored at 25° C., 30° C., 40° C., and 60° C. Each cream was initially tested for appearance (Ap), melting point (mDSC), zeta potential (ZP), pH, and viscosity (V), and each sample was reevaluated once per week for 4 weeks to evaluate stability as follows:

Initial: Ap; mDSC; ZP; pH; and V
Week-1 (25; 40; 60): Ap; mDSC; ZP; pH; and V (if Ap passes)
Week-2 (25; 40): Ap; mDSC; ZP; pH; and V (if Ap passes)
Week-4 (25; 40): Ap; mDSC; pH; and V (if Ap passes)

A sensorial evaluation was conducted by a blinded panel. The panel's evaluation of cosmetic acceptability was based on the criteria provided in Table 15:

TABLE 15

CRITERIA FOR COSMETIC ACCEPTABILITY EVALUATION

| Test Category | Scale |
|---|---|
| General Appearance | 7 = Pleasant↔1 = Unpleasant |
| Color | 7 = Pleasant↔1 = Unpleasant |
| Smell | 7 = Pleasant↔1 = Unpleasant |
| Tackiness | 7 = Not Sticky↔1 = Very Sticky |
| Oiliness | 7 = Not Oily↔1 = Very Oily |
| Cosmetic Elegance | 7 = Very elegant↔1 = Not Elegant |
| Ease of Application | 7 = Spreads Easily↔1 = Not Well |
| Speed of Absorption | 7 = Very Quickly↔1 = Very Slowly |
| Overall Application | 7 = Very Pleasant↔1 = Very Unpleasant |
| Irritation/Stinging | 7 = Not Irritating↔1 = Very Irritating |
| Dry Skin | 7 = Not Drying↔1 = Very Drying |
| Moisturizing | 7 = Moisturizing↔1 = Not Moisturizing |
| Can I put Make-up Over Cream | 7 = Strongly Agree↔1 = Strongly Disagree |
| Overall Impression | 7 = Excellent Product↔1 = Terrible Product |

Figure 2:
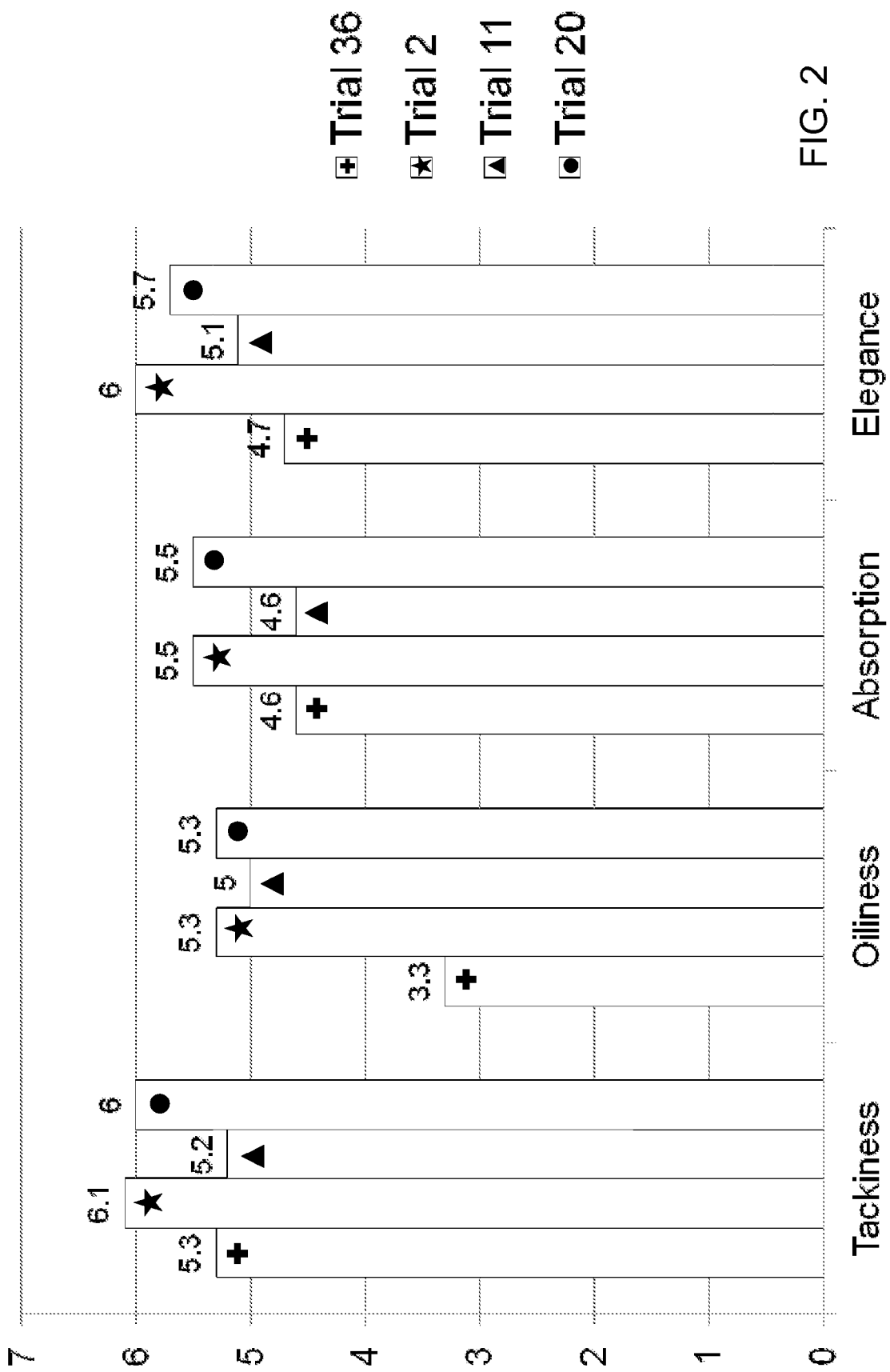
FIG. 2 is a bar graph showing the mean cosmetic acceptability scores including appearance and sensorial evaluation scores for creams of Trial 36, Trial 2, Trial 11 and Trial 20 in key categories.
Figure 3:
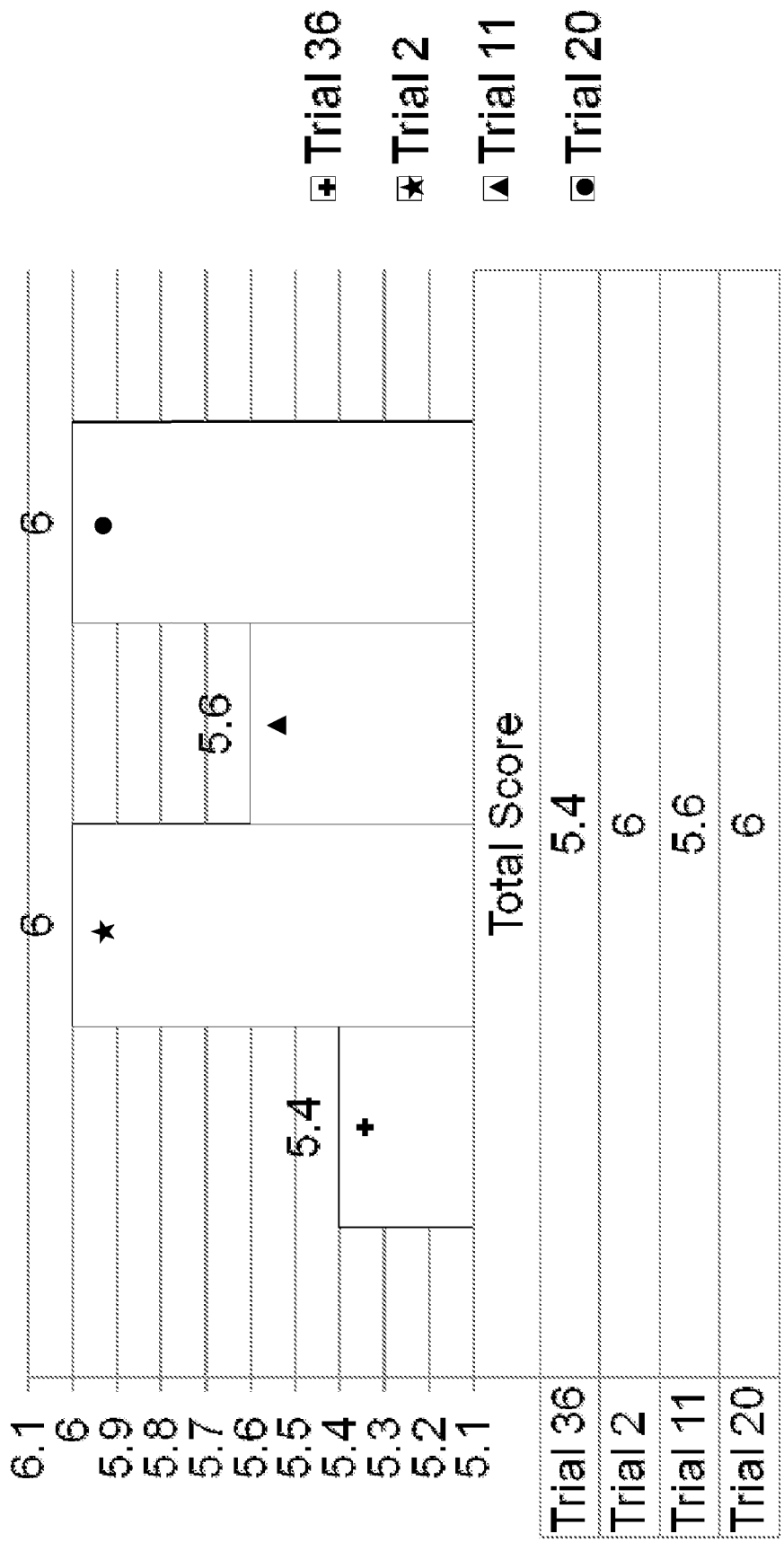
FIG. 3 is a bar graph showing the total mean cosmetic acceptability scores including appearance and sensorial evaluation scores for each of the creams of Trial 36, Trial 2, Trial 11 and Trial 20.

Mean scores by category are provided in FIG. 1, and the mean results for key evaluation categories are provided in FIG. 2. The total mean score is provided in FIG. 3. As indicated in FIG. 1-3, each formulation exhibited acceptable appearance. Overall, the panel selected the formulation of Trial 36 as containing the best sensorial attributes according to the criteria under Table 15.

Modulated Differential Scanning calorimetry (mDSC) and Zeta Potential (ZP) determinations were performed on samples of the Trials 20 through 34 and for the three high wax content formulations Trials 36, 37 and 38. Samples of the creams were subjected to mDSC cycles of heating and cooling from about 7° C. to 60° C. and back. It was found that an optimal formulation combines a buffer system at pH 4.5, such as Trial 22, with a high content of wax-like material (Cetostearyl alcohol and Tefose 63) which demonstrated a physically stable formulation.

Confirmatory studies of mDSC and Zeta Potential were conducted on the formulation of Trial 36. The formulation of Trial 36 was compared with the formulation of Trial 27. Results: Trial 36 formulation showed that no major changes are taking place with respect to the compound structure until 42.5° C. except changes in physical properties of the material after 39° C. in first heat and after 33° C. in second heat. Trial 27 formulation showed that the initial mDSC at 25° C. and after 1 week were less stabile than the formulations of Trial 36. The physical changes are present from about 26° C. and the structural changes show an increased activity after about 40° C. At the same time, the plot of Trial 36 formulation is very similar with the Trial 27 formulation plotted after 1 week at 60° C. stability. The improvement in mDSC of Trial 36 appears to be related to the combined result of adjusting the ratio of cetostearyl alcohol to Tefose™ 63 to 1:1, optimization of the concentrations of Tefose and cetostearyl alcohol, and optimization of the overall total concentrations and ratio of emulsifier to emollient.

The pH of Trial 36 was adjusted to 4.5 using anhydrous citric acid (0.2% by weight) and sodium citrate dihydrate (0.3% by weight), and the zeta potential of this formula was −5.

Example 4

The formulation of Trial 36 was selected for a formal accelerated stability study. For this study Trials 42 at 0.01% API and Trial 43 at 0.15% API were prepared. The purpose of this protocol was to perform a stability study on Oxymetazoline Topical Creams, 0.01% and 0.15% based on Trial 36. The creams were packaged into 30-g glaminate tubes. Approximately 60 tubes of each cream concentration was prepared. The creams were placed on stability at the nominal storage condition of 25° C./60% RH and at accelerated conditions of 40° C./75% RH. Samples were also stored at the intermediate condition, 30° C./75% RH. Viscosity was measured using a Brookfield RVT, C/P, Spindle CPE-52, 25 rpm, RT.

RESULTS: The appearance, viscosity, pH & assay results of the samples were consistent for the sub-samples from top, middle and bottom of the tube as well as the composite sample. This shows that the manufacturing procedure was carried out efficiently. The results indicate the preparation to be a stable formulation.

Example 5

An in vitro permeation procedure for oxymetazoline cream was developed using the 0.01 and 0.10% w/w oxymetazoline cream. The in vitro experiments were conducted using Hanson Microette Franz Cell apparatus and 0.01N PBS (pH 7.4) as the receiving medium. Other critical parameters were evaluated such as the type of semi-synthetic membrane, sample timing (time dependent release-permeability profile), method sensitivity, specificity and linearity.

Permeation characterization of oxymetazoline cream of different strengths (0.01% w/w, 0.05% w/w, 0.10% w/w and 0.15% w/w) was based on flux study across two different artificial membranes (cellulose acetate and polysulfone). The concentration of oxymetazoline which permeated through the membranes was measured using an HPLC assay.

RESULTS: The oxymetazoline permeation rate over the concentration range studied exhibited a dump and die profile, reaching a peak after 0.5 hours of the cream application. After this period, the drug release gradually declined for the next 24 hours. Oxymetazoline permeability ($AUC_{0-24\,h}$) linearly increased in the concentration range 0.01-0.10% w/w. Further increase of drug concentration (0.10-0.15% w/w), did not lead to a proportional increase in the amount of drug delivered across the membrane. The in vitro membrane transport reached saturation above the 0.1% w/w level irrespective the membrane type used.

Permeability efficiency across the cellulose acetate and polysulfone membranes (expressed as a percent of total drug permeated as a function of time) was similar for all four strengths (30-40%) after the 24 hours application period. Lower oxymetazoline release was observed in the case of polysulfone at the lowest 0.01% w/w level. Without wishing to be bound by theory, this effect may be caused by drug binding to this membrane at this low concentration level.

Example 6

Additional formulations were made using Trial 38 as the base formulation and varying the amount of oxymetazoline. Such formulations included oxymetazoline at 0.01%, 0.05%, 0.06%, 0.1%, 0.15%, 0.25%, 0.5%, 1% and 2.5%, and were found to be stable.

Example 7

Stability studies were done on oxymetazoline creams: 0.01% cream, 0.10% cream, and 0.15% cream, after 9 months at 25° C./60% RH, and after 6 months at 40° C./75% RH.

RESULTS: The appearance for all samples at normal and accelerated conditions is in conformance with the initial appearance indicating no change of the appearance from initial. The assay results (potency of API) of the samples at 25° C./60% RH and 40° C./75% RH are all above 100% indicating chemical stability of the drug in the formulation. The pH values at both storage conditions are within the narrow range of 4.30 and 4.70 indicating that the buffer system is maintaining the pH of the formulation. No microbial issues are reported showing that the preservative is efficacious. The viscosity samples at both storage conditions seem to go up and in some cases down. This is not unusual for emulsion systems containing a waxy matrix. In such systems melting and re-crystallization of lipids produce a mixture of wax materials of different crystalline forms that have an impact on the rheological behavior of the cream. Ref: Theory and Practice of Industrial Pharmacy. Lachman, Lieberman and Kanig).

Example 8

Stability studies were done on oxymetazoline creams: 0.25% and 0.50% creams, after 3 months at 25° C./60% RH and after 3 months at 40° C./75% RH.

RESULTS: The appearance of all samples at normal and accelerated conditions is in conformance with the initial appearance indicating no change in appearance from initial. The assay results (potency of API) of the samples at 25° C./60% RH and 40° C./75% RH are all above 100% indicating chemical stability of the drug in the formulation. The pH values at both storage conditions are within the narrow range of 4.10 and 4.60 indicating that the buffer system is maintaining the pH of the formulation. No microbial issues are reported showing that the preservative is efficacious. The viscosity samples at both storage conditions seem to go up and in some cases down. This is not unusual for emulsion systems containing a waxy matrix. In such systems melting and re-crystallization of lipids produce a mixture of wax materials of different crystalline forms that have an impact on the rheological behavior of the cream (Ref: Theory and Practice of Industrial Pharmacy. Lachman, Lieberman and Kanig).

Example 9

The following formulations were made and were found to be stable.

TABLE 16

Oxymetazoline Formulations

| COMPONENT | % W/W | | |
|---|---|---|---|
| Oxymetazoline | 0.5 | 1.0 | 1.5 |
| Phenoxy ethanol | 0.8 | 0.8 | 0.8 |
| Methyl paraben | 0.2 | 0.2 | 0.2 |
| Propyl paraben | 0.05 | 0.05 | 0.05 |
| EDTA | 0.01 | 0.01 | 0.01 |
| BHT | 0.05 | 0.05 | 0.05 |
| PEG 300 | 4.0 | 4.0 | 4.0 |
| Tefose-63 (PEG & Glycol & PEG-32 stearate) | 8.0 | 8.0 | 8.0 |
| Cetostearyl alcohol | 8.0 | 8.0 | 8.0 |
| Med chain triglycerides (caprylic capric triglycerides) | 7.0 | 7.0 | 7.0 |
| Diisopropyl adipate | 7.0 | 7.0 | 7.0 |
| Oleyl alcohol | 7.0 | 7.0 | 7.0 |
| Lanolin | 2.0 | 2.0 | 2.0 |
| Cremophor A-25 | 2.0 | 2.0 | 2.0 |

TABLE 16-continued

Oxymetazoline Formulations

| COMPONENT | % W/W | | |
|---|---|---|---|
| Cremophor A-6 | 2.0 | 2.0 | 2.0 |
| Anhydrous Citric acid | 0.2 | 0.2 | 0.2 |
| Sodium citrate dihydrate | 0.3 | 0.3 | 0.3 |
| Purified Water, USP | QS 100% | QS 100% | QS 100% |

Example 10

A single-center, two-way crossover relative bioavailability study of V-101 (oxymetazoline) cream 0.50% administered topically, and oxymetazoline HCl solution (Afrin®) 0.05% administered intranasally to subjects with moderate to severe erythematous rosacea, was conducted.

Objectives: To assess the relative bioavailability of V-101 cream 0.50% and oxymetazoline nasal spray 0.05% under conditions of maximum use and to evaluate the safety of V-101 cream 0.50% administered topically to the face in male and female subjects with moderate to severe erythematous rosacea under maximum use conditions.

Methodology: This was a double-blind, randomized, 2-way crossover study of V-101 cream 0.50% and oxymetazoline nasal spray 0.05% administered in adult subjects with moderate to severe erythematous rosacea. Subjects were seen for screening up to 28 days before Treatment Visit 1. Subjects who were eligible for randomization had 2 treatment visits separated by a washout period of 6 to 21 days. At Treatment Visit 1 subjects were treated with one 0.5 g facial application of V 101 cream 0.50% plus 3 sprays of control (normal saline) nasal spray in each nostril (Treatment A) or one 0.5 g facial application of vehicle cream plus 3 sprays of oxymetazoline nasal spray 0.05% in each nostril (Treatment B). The treatment sequence (A then B or B then A) was randomized. Subjects received the opposite treatment at Treatment Visit 2. Evaluations and blood sampling for determination of plasma concentrations of oxymetazoline took place through 12 hours after dosing at each treatment visit.

Number of Subjects (Planned and Analyzed): Approximately 28 subjects (14 per treatment sequence) were planned to ensure that at least 20 subjects completed 2 treatment visits; 28 subjects were randomized and included in the analyses.

Diagnosis and Main Criteria for Inclusion: Diagnosis: Moderate to severe erythematous rosacea. Main Inclusion Criteria: Males and females age≥18 years in good general health with a clinical diagnosis of erythematous rosacea, Subject's Self Assessment (SSA) and Clinician's Erythema Assessment (CEA) scores of ≥3, ≤3 inflammatory lesions (papules and/or pustules) within the treatment area, intraocular pressure (TOP)≥10 mm Hg and ≤21 mm Hg, and females with negative pregnancy test who were non lactating, and using an active method of birth control.

Test Product, Dose and Mode of Administration, Batch Number: V-101 (oxymetazoline) cream 0.50% (lot B10013) was applied topically to the face by a site staff member at a dose of 0.5 g after the subject administered the assigned nasal spray.

Duration of Treatment: The study included 2 treatments separated by a washout period of 6 to 21 days. Treatment A was V-101 cream 0.50% and control saline nasal spray. Treatment B was vehicle cream and oxymetazoline nasal spray 0.05%.

Criteria for Evaluation: Efficacy was evaluated as the overall severity of erythema on the treatment area at the study visits by the subject, using the 5-point SSA scale and by the investigator, using the 5-point CEA scale at 0 (just prior to the study medication dose), 2, 3, 4, 6, 9, and 12 hours post dose. Pharmacokinetics and relative bioavailability were to be evaluated based on quantitation of oxymetazoline levels from blood samples collected at each treatment visit at 0 (just prior to the study medication dose), 1, 2, 3, 4, 6, 9, and 12 hours post-dose. Safety was evaluated by treatment-emergent adverse events (AEs), laboratory evaluations, vital signs, electrocardiograms (ECGs), and intraocular pressure (TOP).

Analysis of Efficacy: Clinician's Erythema Assessment (CEA): The primary efficacy variable, the mean change from pre-dose in AUC for CEA, was −9.107 following treatment with V-101 cream 0.50% and control nasal spray compared to −0.411 following treatment with vehicle cream and oxymetazoline nasal spray 0.05%. The difference between the treatments was statistically significant, p<0.001. Across both treatment sequences combined, the CEA pre-dose and change from pre-dose values are summarized in Table 17. Statistically significantly greater improvement was seen following treatment with V-101 cream 0.50% and control nasal spray compared to vehicle cream and oxymetazoline nasal spray 0.05% at all time points from 2 through 12 hours post dose (p≤0.003).

TABLE 17

Clinician's Erythema Assessment: Mean Pre-Dose and Mean Change from Pre-Dose for Subjects Completing the Study (Treatment Sequences Combined)

| | Mean (Standard Deviation) | | |
|---|---|---|---|
| Time | V-101 Cream + Control Spray (N = 28) | Vehicle Cream + Oxy 0.05% Spray (N = 28) | P-value[1] |
| Pre-dose | 3.214 (0.418) | 3.214 (0.418) | NA |
| 2 Hours Change | −1.214 (0.833) | −0.143 (0.448) | <0.001 |
| 3 Hours Change | −1.571 (0.920) | −0.036 (0.331) | <0.001 |
| 4 Hours Change | −1.036 (0.793) | −0.036 (0.189) | <0.001 |
| 6 Hours Change | −0.893 (0.832) | 0.000 (0.272) | <0.001 |
| 9 Hours Change | −0.500 (0.694) | −0.036 (0.189) | <0.001 |
| 12 Hours Change | −0.286 (0.460) | 0.000 (0.272) | 0.003 |
| Avg Hrs 3-6 Change | −1.107 (0.832) | −0.036 (0.189) | <0.001 |

Avg = average,
NA = not applicable,
Oxy = oxymetazoline
[1]P-values were calculated using analysis of covariance based on change from pre dose and variables were analyzed as continuous variables.

An analysis was performed in which treatment success was defined as a score of 0 or 1 or a reduction from baseline of at least 2 grades on the CEA. The success rate was statistically significantly greater for treatment with V-101 cream 0.50% and control nasal spray than for treatment with vehicle cream and oxymetazoline nasal spray 0.05% from 2 through 6 hours (p≤0.010 by the chi-square test. For the averaged Hours 3-6 score, where success rate was defined as a score of 0 or 1 or a reduction from baseline of at least 1.5 grades on the CEA, 9 of 28 (32%) subjects following treatment with V-101 cream 0.50% and control nasal spray and none of 28 subjects (0%) following treatment with vehicle cream and oxymetazoline nasal spray 0.05% achieved treatment success (p=0.010 by the chi square test).

Subject's Self-Assessment (SSA): The mean change from pre-dose in AUC for SSA was 6.661 following treatment with V 101 cream 0.50% and control nasal spray compared to 0.339 following treatment with vehicle cream and oxymetazoline nasal spray 0.05%. The difference between the treatments was statistically significant, p<0.001.

Across both treatment sequences combined, the SSA pre-dose and change from pre-dose values are summarized in Table 18. Statistically significantly greater improvement was seen following treatment with V-101 cream 0.50% and control nasal spray compared to vehicle cream and oxymetazoline nasal spray 0.05% at all time points from 2 through 12 hours post dose (p<0.001).

TABLE 18

Subject's Self-Assessment: Mean Pre-Dose and Mean Change from Pre-Dose for Subjects Completing the Study (Treatment Sequences Combined)

| | Mean (Standard Deviation) | | |
|---|---|---|---|
| Time | V-101 Cream + Control Spray (N = 28) | Vehicle Cream + Oxy 0.05% Spray (N = 28) | P-value[1] |
| Pre-dose | 3.071 (0.262) | 3.107 (0.315) | NA |
| 2 Hours Change | −0.500 (0.638) | 0.000 (0.000) | <0.001 |
| 3 Hours Change | −0.607 (0.629) | 0.036 (0.189) | <0.001 |
| 4 Hours Change | −0.643 (0.731) | 0.036 (0.189) | <0.001 |
| 6 Hours Change | −0.643 (0.731) | 0.036 (0.189) | <0.001 |
| 9 Hours Change | −0.607 (0.737) | 0.036 (0.189) | <0.001 |
| 12 Hours Change | −0.607 (0.786) | 0.036 (0.189) | <0.001 |
| Avg Hrs 3-6 Change | −0.643 (0.731) | 0.036 (0.189) | <0.001 |

Avg = average,
NA = not applicable,
Oxy = oxymetazoline
[1]P-values were calculated using analysis of covariance based on change from pre dose and variables were analyzed as continuous variables.

An analysis was performed in which treatment success was defined as a score of 0 or 1 or a reduction from baseline of at least 2 grades on the SSA. The success rate was higher for treatment with V-101 cream 0.50% and control nasal spray than for treatment with vehicle cream and oxymetazoline nasal spray 0.05% from 2 through 12 hours but the between-treatment differences were not statistically significant. For the averaged Hours 3-6 score, where success rate was defined as a score of 0 or 1 or a reduction from baseline of at least 1.5 grades on the SSA, 2 of 28 (7%) subjects following treatment with V-101 cream 0.50% and control nasal spray and none of 28 subjects (0%) following treatment with vehicle cream and oxymetazoline nasal spray 0.05% achieved treatment success.

In an analysis defining treatment success as a score of 0 or 1 or a reduction from baseline of at least 2 grades on both the CEA and the SSA, the success rate was higher for treatment with V-101 cream 0.50% and control nasal spray than for treatment with vehicle cream and oxymetazoline nasal spray 0.05% from 2 through 12 hours but the between-treatment differences were not statistically significant. For the averaged Hours 3-6 score, where success rate was defined as a score of 0 or 1 or a reduction from baseline of at least 1.5 grades on both the CEA and the SSA, 2 of 28 (7%) subjects following treatment with V 101 cream 0.50% and control nasal spray and none of 28 subjects (0%) following treatment with vehicle cream and oxymetazoline nasal spray 0.05% achieved treatment success.

Pharmacokinetics: In general, minimal systemic exposure of oxymetazoline was observed following topical facial application of V-101 cream 0.50% in subjects with moderate to severe erythematous rosacea. The mean maximum observed plasma concentration ($C_{max}$) and area under the plasma concentration-time curve from 0 hour to the last measurable plasma concentration ($AUC_{0-t}$) following treatment with V-101 cream 0.50% and control nasal spray were 34.7 pg/mL and 295 pg·hr/mL respectively. Following treatment with vehicle cream and oxymetazoline nasal spray 0.05%, the median time to $C_{max}$ ($T_{max}$) was 3.00 hours and mean $C_{max}$, $AUC_{0-t}$, area under the plasma-concentration-time curve extrapolated to infinity ($AUC_{0-\infty}$), apparent terminal phase rate constant ($\lambda_z$), and apparent plasma terminal phase half-life ($t_{1/2}$) were 245 pg/mL, 1741 pg·hr/mL, 1859 pg·hr/mL, 0.143 (1/hr), and 4.99 hours, respectively.

Conclusion: A single topical facial administration of V-101 cream 0.50% under maximum use conditions in subjects with moderate to severe erythematous rosacea resulted in minimal systemic exposure when compared with a single administration of Afrin Nasal Spray 0.05%. Topical facial application of V-101 cream 0.50% was well tolerated and significantly reduced erythema from 2 to 12 hours post-dose.

The invention claimed is:

1. A pharmaceutical composition comprising:
   about 0.0075% to about 2% by weight of oxymetazoline;
   about 1% to about 50% by weight of an emollient comprising medium chain triglycerides, diisopropyl adipate, oleyl alcohol and lanolin;
   about 8% to about 25% by weight of an emulsifier comprising: cetostearyl alcohol, about 7% to about 10% by weight of PEG-6 stearate/PEG-32 stearate/glycol stearate mixture, macrogol (6) cetostearyl ether, and macrogol (25) cetostearyl ether; wherein the composition is a cream.

2. The pharmaceutical composition of claim 1, having an emulsifier to emollient ratio of from about 0.7:1 to about 1.8:1.

3. The pharmaceutical composition of claim 1, further comprising an additive selected from the group consisting of preservatives, emulsion stabilizers, pH adjusters, chelating agents, viscosity modifiers, anti-oxidants, opacifying agents, skin conditioners, buffers, and combinations thereof.

4. The pharmaceutical composition of claim 1, wherein the composition further comprises a topically active pharmaceutical agent selected from the group consisting of an antimycobacterial agent, an anti-rosacea agent, and a mixture thereof.

5. The pharmaceutical composition of claim 1, wherein the composition has a pH from about 2.0 to about 7.0 at room temperature.

6. The pharmaceutical composition of claim 1, wherein the pH is unchanged after about 4 weeks storage at about 25° C./60% RH, about 30° C./75% RH or about 40° C./75% RH.

7. The pharmaceutical composition of claim 1, wherein the pH is unchanged after about 1 week storage at about 60° C.

8. The pharmaceutical composition of claim 1, further comprising a vasoconstrictor.

9. The pharmaceutical composition of claim 1, further comprising one or more components selected from:
   one or more preservatives in an amount of from about 0.01% to about 5% by weight of the pharmaceutical composition;
   one or more chelating agents in an amount of about 0.001% to about 2% by weight of the pharmaceutical composition;
   one or more viscosity modifiers in an amount of from about 0.5% to about 30% by weight of the pharmaceutical composition;
   one or more antioxidants in an amount of from about 0.01% to about 3% by weight of the pharmaceutical composition;
   one or more opacifying agents in an amount of from about 0.01% to about 20% by weight of the pharmaceutical composition;
   one or more skin conditioners in an amount of from about 1% to about 50% by weight of the pharmaceutical composition;
   one or more pH regulators in an amount sufficient to provide a pH of from about 2.5 to about 7.0 for the pharmaceutical composition; and combinations thereof.

10. The pharmaceutical composition of claim 1, which is physically and chemically stable.

11. The pharmaceutical composition of claim 1, wherein the emollient comprises about 7% by weight of medium chain triglycerides, about 7% by weight of diisopropyl adipate, about 7% by weight of oleyl alcohol and about 2% by weight of lanolin.

12. The pharmaceutical composition of claim 1, which comprises about 2% by weight of macrogol (6) cetostearyl ether and about 2% by weight of macrogol (25) cetostearyl ether.

13. The pharmaceutical composition of claim 1, which comprises about 7% to about 8% by weight of PEG-6 stearate/PEG-32 stearate/glycol stearate mixture.

14. The pharmaceutical composition of claim 1, which comprises about 4% to about 8% by weight of cetostearyl alcohol.

15. The pharmaceutical composition of claim 1, further comprising 0.01% to about 5% by weight of a preservative comprising methylparaben, propylparaben, and phenoxyethanol.

* * * * *